(12) United States Patent
Tenjarla et al.

(10) Patent No.: US 9,512,095 B2
(45) Date of Patent: Dec. 6, 2016

US009512095B2

(54) POLYMORPH FORMS OF DESAZADESFERRITHIOCIN ANALOGS

(71) Applicant: Ferrokin Biosciences, Inc., Wayne, PA (US)

(72) Inventors: Srini Tenjarla, Wayne, PA (US); Paul McGee, Basingstoke (GB)

(73) Assignee: FERROKIN BIOSCIENCES, INC., Wayne, PA (US)

( * ) Notice: Subject to any disclaimer, the term of this patent is extended or adjusted under 35 U.S.C. 154(b) by 0 days.

(21) Appl. No.: 14/775,982

(22) PCT Filed: Mar. 13, 2014

(86) PCT No.: PCT/US2014/026365
§ 371 (c)(1),
(2) Date: Sep. 14, 2015

(87) PCT Pub. No.: WO2014/143630
PCT Pub. Date: Sep. 18, 2014

(65) Prior Publication Data
US 2016/0024034 A1    Jan. 28, 2016

Related U.S. Application Data

(60) Provisional application No. 61/789,220, filed on Mar. 15, 2013.

(51) Int. Cl.
*C07D 277/12*    (2006.01)

(52) U.S. Cl.
CPC ......... *C07D 277/12* (2013.01); *C07B 2200/13* (2013.01)

(58) Field of Classification Search
None
See application file for complete search history.

(56) References Cited

U.S. PATENT DOCUMENTS

| | | |
|---|---|---|
| 8,063,227 B2 | 11/2011 | Tapper et al. |
| 8,324,397 B2 | 12/2012 | Bergeron, Jr. |
| 8,710,087 B2 | 4/2014 | Tapper et al. |
| 8,829,197 B2 | 9/2014 | Tapper et al. |
| 8,846,731 B2 | 9/2014 | Tapper et al. |
| 8,993,606 B2 | 3/2015 | Rienhoff, Jr. |
| 9,174,948 B2 | 11/2015 | Bergeron, Jr. |
| 2008/0214630 A1 | 9/2008 | Bergeron |
| 2010/0093812 A1 | 4/2010 | Bergeron, Jr. |
| 2010/0137383 A1 | 6/2010 | Tapper et al. |
| 2011/0053993 A1 | 3/2011 | McCall, Jr. et al. |
| 2011/0160257 A1 | 6/2011 | Tapper et al. |
| 2011/0275636 A1 | 11/2011 | Malecha |
| 2012/0202857 A1 | 8/2012 | Tapper et al. |
| 2012/0270911 A1 | 10/2012 | Tapper et al. |
| 2013/0210870 A1 | 8/2013 | Bergeron, Jr. |
| 2013/0225645 A1 | 8/2013 | Rienhoff, Jr. |
| 2015/0299151 A1 | 10/2015 | Tapper et al. |
| 2016/0022645 A1 | 1/2016 | Bergeron, Jr. |

FOREIGN PATENT DOCUMENTS

| | | | |
|---|---|---|---|
| WO | WO-2006/107626 A1 | 10/2006 | |
| WO | WO-2008/115433 A1 | 9/2008 | |
| WO | WO 2010/009120 A2 * | 1/2010 | ........... C07D 277/22 |
| WO | WO-2011/017054 A2 | 2/2011 | |
| WO | WO-2013/086312 A1 | 6/2013 | |
| WO | WO-2014/089482 A1 | 6/2014 | |
| WO | WO-2014/143630 A1 | 9/2014 | |

OTHER PUBLICATIONS

Bergeron, R.J. et al. Design, Synthesis, and Testing of Non-Nephrotoxic Desazadesferrithiocin Polyether Analogues, J. Med. Chem., 51(13): 3913-3923 (2008).
Bergeron, R.J. et al., Impact of the 3,6,9-Trioxadecyloxy Group on Desazadesferrithiocin Analogue Iron Clearance and Organ Distribution, J. Med. Chem., 50: 3302-3313 (2007).
Durbin, P.W. et al., Chelating Agents for Uranium(Vi): 2. Efficacy and Toxicity of Tetradentate Catecholate and Hydroxypyridinonate Ligands in Mice, Health Phys., 78(5): 511-521, (2000).
International Search Report for PCT/US2013/073662, 3 pages (Mar. 28, 2014).
International Search Report for PCT/US2014/026365, 3 pages (May 27, 2014).
Janka, G.E. et al. Intravenous and Subcutaneous Desferrioxamine Therapy in Children with Severe Iron Overload, Eur. J. Pediatr., 137(3): 285-290 (1981).
*Rienhoff* v. *Bergeron*, Declaration of Interference, Patent Interference No. 106,055, 88 pages (Entered Apr. 28, 2016).
Written Opinion for PCT/US2013/073662, 13 pages (Mar. 28, 2014).
Written Opinion for PCT/US2014/026365, 4 pages (May 27, 2014).

* cited by examiner

*Primary Examiner* — Brian J Davis
(74) *Attorney, Agent, or Firm* — Choate, Hall & Stewart LLP; John P. Rearick; Nicholas J. Pace

(57) ABSTRACT

The present invention provides a solid form and compositions thereof, which are useful as metal chelators and which exhibit desirable characteristics for the same.

13 Claims, 16 Drawing Sheets

Four forms of Compound 1 identified by DSC. In ascending order: Form A, Form B, Form C, and Form D.

Relationships between Form A, Form B, Form C, and Form D by water content [water content % w/w by KF]

Change of forms after exposure to humid conditions.

Change of forms after stirring in original isolation solvents.

Figure 6   In ascending order, overlay of Form D, Form D, Form A containing Form D, and Form A.

Figure 8 XRPD diffractograms of Form D (lower line) and Form D (upper line)

Figure 9  XRPD diffractograms of the conversion of A (upper line) to Form D (lower line)

Figure 10 XRPD diffractograms of the conversion of Form D (lower line) and Form A (upper line)

Figure 11 Computation estimate of XRPD diffractograms of the conversion from Form A (bottom line), to Form D (top line).

Form A: Thermal ellipsoids drawn at the 35% probability level, selected hydrogens and Na-O bonds omitted for clarity.

Form B: Thermal ellipsoids drawn at the 35% probability level, selected hydrogens omitted for clarity.

POLYMORPH FORMS OF DESAZADESFERRITHIOCIN ANALOGS

CROSS REFERENCE TO RELATED APPLICATIONS

This application claims priority to U.S. provisional patent application No. 61/789,220, filed Mar. 15, 2013, the entire contents of which are hereby incorporated herein.

BACKGROUND OF THE INVENTION

Metal ions are critical to the proper functioning of living systems. Ions such as $Fe^{2+}$, $Zn^{2+}$, $Cu^{2-}$, $Ca^{2+}$, and $Co^{3+}$, to name but a few, can be found in the active sites of over a third of known enzymes and other functional proteins such as RNA polymerase, DNA transcription factors, cytochromes $P_{450}s$, hemoglobin, myoglobin, and coenzymes such as vitamin $B_{12}$. There, these metals serve to regulate oxidation and reduction reactions, stabilize or shield charge distributions, and orient substrates for reactions.

However, the body has a limited ability to absorb and excrete metals, and an excess can lead to toxicity. As one example, an excess of iron, whether derived from red blood cells chronically transfused, necessary in such conditions such as beta thalassemia major, or from increased absorption of dietary iron such as hereditary hemochromatosis can be toxic through the generation by iron of reactive oxygen species from $H_2O_2$. In the presence of $Fe^{2+}$, $H_2O_2$ is reduced to the hydroxyl radical (HO), a highly reactive species, a process known as the Fenton reaction. The hydroxyl radical reacts very quickly with a variety of cellular constituents and can initiate free radicals and radical-mediated chain processes that damage DNA and membranes, as well as produce carcinogens. Without effective treatment, iron levels progressively increases with deposition in the liver, heart, pancreas, and other endocrine organs. Iron accumulation can result in produce (i) liver disease that may progress to cirrhosis and hepatocellular carcinoma, (ii) diabetes related both to iron-induced decreases in pancreatic β-cell secretion and increases in hepatic insulin resistance and (iii) heart disease, the leading cause of death in β-thalassemia major and other anemia associated with transfusional iron overload.

Other metals, especially those ions with little or no endogenous function, may find their way into the body and effect damage. Heavy metal ions such as $Hg^{2+}$ can replace ions such as $Zn^{2+}$ in metalloproteins and render them inactive, resulting in serious acute or chronic toxicity that can end in death or cause birth defects. Even more significantly, radioactive isotopes of the lanthanide and actinide series can visit grave illness on an individual exposed to them by mouth, air, or skin contact. Such exposure could result not only from the detonation of a nuclear bomb or a "dirty bomb" composed of nuclear waste, but also from the destruction of a nuclear power facility.

Traditional standard therapies for metal overload include the use of metal chelators such as deferoxamine (DFO, N'-[5-(acetyl-hydroxy-amino)pentyl]-N-[5-[3-(5-aminopentyl-hydroxy-carbamoyl)propanoylamino]pentyl]-N-hydroxy-butane diamide). DFO is an effective metal chelator; unfortunately, it is not orally bioavailable and has a very short half-life in serum. More recently, other metal chelators have been developed for clinical use, but have serious side effects including life-threatening agranulocytosis (deferiprone, Ferriprox), renal and liver toxicity (deferesirox, Exjade). Others are not as effective and require repeated daily doses.

Therefore, there is still a great need for a safe, effective and orally active metal chelator for the treatment of metal overload.

SUMMARY OF THE INVENTION

It has now been found that certain novel polymorphs of the present invention, and compositions thereof, are useful as metal chelators and exhibit desirable characteristics for the same. In general, these polymorphs, and pharmaceutically acceptable compositions thereof, are useful for treating or lessening the severity of a variety of diseases or disorders as described in detail herein.

In certain aspects, the invention provides for polymorph form A, polymorph form B, polymorph form C, polymorph form D, and amorphous forms of Compound 1:

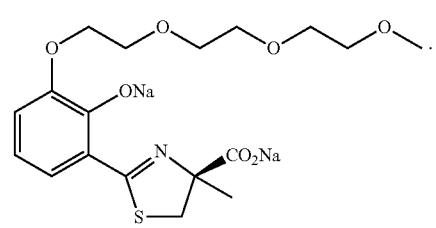

and solvates and hydrates thereof.

In certain aspects, the invention provides for a crystalline form of Compound 1 having a water content in the range of about 1-9 wt %.

In certain embodiments, the water content is approximately 6-8 wt %.

In various embodiments, the water content is approximately 5-7.5 wt %.

In various embodiments, the water content is approximately 4-6 wt %.

In various embodiments, the water content is approximately 1-4 wt %.

In certain aspects, the invention provides Form A of Compound 1:

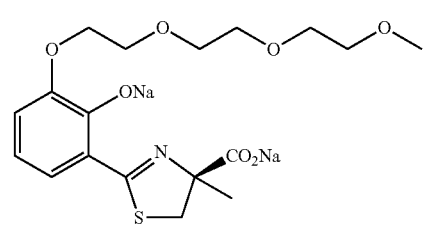

having one or more peaks in its powder X-ray diffraction pattern selected from those at about 5.8°, about 7.3°, about 7.6°, about 10.7°, about 11.3°, about 11.6°, about 14.6°, about 16.4°, about 16.8°, about 17.3°, about 18.4°, about 18.9°, about 20.4°, about 20.9°, about 21.4°, about 21.8°, about 23.8°, about 25.8°, about 26.4°, about 27.5°, about 29.1°, about 30.3°, about 31.4°, and about 32.4° 2-theta. In certain embodiments, "about" refers to +/−0.5°. In certain embodiments, "about" refers to +/−0.4°. In certain embodiments, "about" refers to +/−0.3°. In certain embodiments, "about" refers to +/−0.2°. In certain embodiments, "about" refers to +/−0.1°.

In certain embodiments, two or more peaks in its powder X-ray diffraction pattern are selected from those at about 5.8°, about 7.3°, about 7.6°, about 10.7°, about 11.3°, about 11.6°, about 14.6°, about 16.4°, about 16.8°, about 17.3°, about 18.4°, about 18.9°, about 20.4°, about 20.9°, about 21.4°, about 21.8°, about 23.8°, about 25.8°, about 26.4°, about 27.5°, about 29.1°, about 30.3°, about 31.4°, and about 32.4° 2-theta.

In certain embodiments, three or more peaks in its powder X-ray diffraction pattern are selected from those at about 5.8°, about 7.3°, about 7.6°, about 10.7°, about 11.3°, about 11.6°, about 14.6°, about 16.4°, about 16.8°, about 17.3°, about 18.4°, about 18.9°, about 20.4°, about 20.9°, about 21.4°, about 21.8°, about 23.8°, about 25.8°, about 26.4°, about 27.5°, about 29.1°, about 30.3°, about 31.4°, and about 32.4° 2-theta.

In certain embodiments, substantially all of the peaks in its powder X-ray diffraction pattern are selected from those at about 5.8°, about 7.3°, about 7.6°, about 10.7°, about 11.3°, about 11.6°, about 14.6°, about 16.4°, about 16.8°, about 17.3°, about 18.4°, about 18.9°, about 20.4°, about 20.9°, about 21.4°, about 21.8°, about 23.8°, about 25.8°, about 26.4°, about 27.5°, about 29.1°, about 30.3°, about 31.4°, and about 32.4° 2-theta.

In certain embodiments, substantially all of the peaks in its powder X-ray diffraction pattern are selected from those at about: 5.8°, 7.3°, 7.6°, 10.7°, 11.3°, 11.6°, 14.6°, 16.4°, 16.8°, 17.3°, 18.4°, 18.9°, 20.4°, 20.9°, 21.4°, 21.8°, 23.8°, 25.8°, 26.4°, 27.5°, 29.1°, 30.3°, 31.4°, 32.4° (2θ, ld.p).

In certain embodiments, Form A has a powder X-ray diffraction pattern substantially similar to that depicted in FIG. 1.

In various embodiments, Form A has a water content of about 5-10% w/w. In various embodiments, Form A has a water content of about 6-8% w/w. In various embodiments, Form A has a water content of about 7.5% w/w.

In certain embodiments, the invention provides Form A, wherein Form A is a hydrate comprising 1, 1.5, 2, 2.5 or 3 equivalents of water. In certain embodiments, Form A comprises 1 equivalent of water. In certain embodiments, Form A comprises 1.5 equivalents of water. In certain embodiments, Form A comprises 2 equivalents of water. In certain embodiments, Form A comprises 2.5 equivalents of water. In certain embodiments, Form A comprises 3 equivalents of water.

In certain embodiments, the invention provides Form A in crystalline form. In certain embodiments, the Form A crystalline form has a space group of P2$_1$. In certain embodiments, the Form A crystalline form has a unit cell dimension of a=16.073(4) Å, b=5.7900(13) Å, and c=25.467(6) Å. In certain embodiments, the Form A crystalline form has a crystal size of about 0.240×0.030×0.010 mm³. In certain embodiments, the Form A crystalline form has a crystal density of about 1.414 Mg/m³.

In certain aspects, the invention provides Form B of Compound 1:

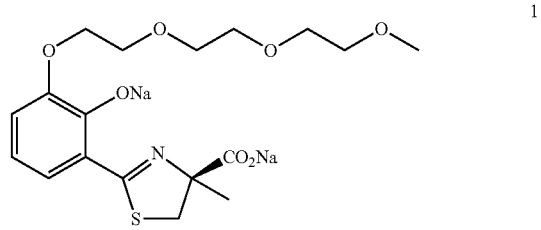

having one or more peaks in its powder X-ray diffraction pattern selected from those at about 6.6°, about 9.5°, about 10.3°, about 13.1°, about 15.8°, about 16.0°, about 17.4°, about 18.2°, about 18.9°, about 19.8°, about 20.3°, about 20.7°, about 21.1°, about 21.7°, about 22.2°, about 23.0°, about 23.3°, about 24.6°, about 25.2°, about 26.2°, about 26.8°, about 27.2°, about 28.7°, and about 30.0° 2-theta. In certain embodiments, "about" refers to +/−0.5°. In certain embodiments, "about" refers to +/−0.4°. In certain embodiments, "about" refers to +/−0.3°. In certain embodiments, "about" refers to +/−0.2°. In certain embodiments, "about" refers to +/−0.1°.

In various embodiments, two or more peaks in its powder X-ray diffraction pattern are selected from those at about 6.6°, about 9.5°, about 10.3°, about 13.1°, about 15.8°, about 16.0°, about 17.4°, about 18.2°, about 18.9°, about 19.8°, about 20.3°, about 20.7°, about 21.1°, about 21.7°, about 22.2°, about 23.0°, about 23.3°, about 24.6°, about 25.2°, about 26.2°, about 26.8°, about 27.2°, about 28.7°, and about 30.0° 2-theta.

In various embodiments, three or more peaks in its powder X-ray diffraction pattern are selected from those at about 6.6°, about 9.5°, about 10.3°, about 13.1°, about 15.8°, about 16.0°, about 17.4°, about 18.2°, about 18.9°, about 19.8°, about 20.3°, about 20.7°, about 21.1°, about 21.7°, about 22.2°, about 23.0°, about 23.3°, about 24.6°, about 25.2°, about 26.2°, about 26.8°, about 27.2°, about 28.7°, and about 30.0° 2-theta.

In various embodiments, substantially all of the peaks in its powder X-ray diffraction pattern are selected from those at about 6.6°, about 9.5°, about 10.3°, about 13.1°, about 15.8°, about 16.0°, about 17.4°, about 18.2°, about 18.9°, about 19.8°, about 20.3°, about 20.7°, about 21.1°, about 21.7°, about 22.2°, about 23.0°, about 23.3°, about 24.6°, about 25.2°, about 26.2°, about 26.8°, about 27.2°, about 28.7°, and about 30.0° 2-theta.

In various embodiments, substantially all of the peaks in its powder X-ray diffraction pattern are selected from those at about: 6.6°, 9.5°, 10.3°, 13.1°, 15.8°, 16.0°, 17.4°, 18.2°, 18.9°, 19.8°, 20.3°, 20.7°, 21.1°, 21.7°, 22.2°, 23.0°, 23.3°, 24.6°, 25.2°, 26.2°, 26.8°, 27.2°, 28.7°, 30.0° (2θ, ld.p).

In various embodiments, Form B has a powder X-ray diffraction pattern substantially similar to that depicted in FIG. 1.

In certain embodiments, Form B has a water content of about 5-7.5% w/w. In certain embodiments, Form B has a water content of about 7.0% w/w.

In certain embodiments, the invention provides Form B, wherein Form A is a hydrate comprising 1, 1.5, 2, 2.5 or 3 equivalents of water. In certain embodiments, Form B comprises 1 equivalent of water. In certain embodiments, Form B comprises 1.5 equivalents of water. In certain embodiments, Form B comprises 2 equivalents of water. In certain embodiments, Form B comprises 2.5 equivalents of water. In certain embodiments, Form B comprises 3 equivalents of water.

In certain embodiments, the invention provides for Form B in crystalline form. In various embodiments, the crystalline Form B has a space group of P2$_1$. In various embodiments, the crystalline Form B has a unit cell dimension of a=5.795(3) Å, b=17.155(10) Å, and c=43.89(3) Å. In various embodiments, the crystalline Form B has a crystal size of about 0.120×0.080×0.050 mm$^3$. In certain embodiments, the Form B crystalline form has a crystal density of about 1.434 Mg/m$^3$.

In various aspects, the invention provides Form C of Compound 1:

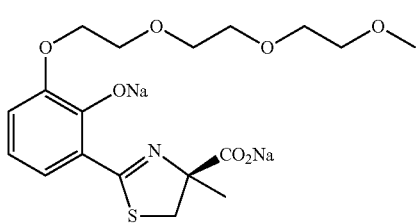

having one or more peaks in its powder X-ray diffraction pattern selected from those at about 6.6°, about 6.8°, about 9.5°, about 9.8°, about 10.3°, about 10.7°, about 13.4°, about 16.3°, about 18.2°, about 19.5°, about 19.9°, about 22.0°, about 23.0°, about 23.4°, about 24.9°, about 25.8°, about 26.5°, about 27.4°, and about 29.5° 2-theta. In certain embodiments, "about" refers to +/−0.5°. In certain embodiments, "about" refers to +/−0.4°. In certain embodiments, "about" refers to +/−0.3°. In certain embodiments, "about" refers to +/−0.2°. In certain embodiments, "about" refers to +/−0.1°.

In various embodiments, two or more peaks in its powder X-ray diffraction pattern are selected from those at about 6.6°, about 6.8°, about 9.5°, about 9.8°, about 10.3°, about 10.7°, about 13.4°, about 16.3°, about 18.2°, about 19.5°, about 19.9°, about 22.0°, about 23.0°, about 23.4°, about 24.9°, about 25.8°, about 26.5°, about 27.4°, and about 29.5° 2-theta.

In various embodiments, three or more peaks in its powder X-ray diffraction pattern selected from those at about 6.6°, about 6.8°, about 9.5°, about 9.8°, about 10.3°, about 10.7°, about 13.4°, about 16.3°, about 18.2°, about 19.5°, about 19.9°, about 22.0°, about 23.0°, about 23.4°, about 24.9°, about 25.8°, about 26.5°, about 27.4°, and about 29.5° 2-theta.

In various embodiments, substantially all of the peaks in its powder X-ray diffraction pattern are selected from those at about 6.6°, about 6.8°, about 9.5°, about 9.8°, about 10.3°, about 10.7°, about 13.4°, about 16.3°, about 18.2°, about 19.5°, about 19.9°, about 22.0°, about 23.0°, about 23.4°, about 24.9°, about 25.8°, about 26.5°, about 27.4°, and about 29.5° 2-theta.

In various embodiments, substantially all of the peaks in its powder X-ray diffraction pattern are selected from those at about: 6.6°, 6.8°, 9.5°, 9.8°, 10.3°, 10.7°, 13.4°, 16.3°, 18.2°, 19.5°, 19.9°, 22.0°, 23.0°, 23.4°, 24.9°, 25.8°, 26.5°, 27.4°, 29.5° (2θ, ld.p).

In certain embodiments, Form C has a powder X-ray diffraction pattern substantially similar to that depicted in FIG. 1.

In certain embodiments, Form C has a water content of about 4-6% w/w. In certain embodiments, Form C has a water content of about 5.7% w/w.

In certain embodiments, Form C is a hydrate comprising 0.1, 0.2, 0.3, 0.4, 0.5, 0.6, 0.7, 0.8, 0.9, or 1 equivalents of water. In various embodiments, Form C is a hydrate comprising 0.1 equivalents of water. In various embodiments, Form C is a hydrate comprising 0.2 equivalents of water. In various embodiments, Form C is a hydrate comprising 0.3 equivalents of water. In various embodiments, Form C is a hydrate comprising 0.4 equivalents of water. In various embodiments, Form C is a hydrate comprising 0.5 equivalents of water. In various embodiments, Form C is a hydrate comprising 0.6 equivalents of water. In various embodiments, Form C is a hydrate comprising 0.7 equivalents of water. In various embodiments, Form C is a hydrate comprising 0.8 equivalents of water. In various embodiments, Form C is a hydrate comprising 0.9 equivalents of water.

In various aspects, the invention provides Form D of Compound 1:

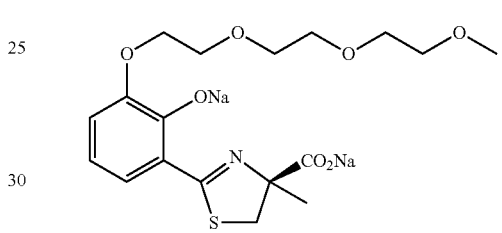

having one or more peaks in its powder X-ray diffraction pattern selected from those at about 6.8°, about 9.4°, about 11.5°, about 13.6°, about 15.3°, about 17.0°, about 19.3°, about 20.2°, about 21.5°, about 22.3°, about 23.0°, about 25.2°, and about 29.4° 2-theta. In certain embodiments, "about" refers to +/−0.5°. In certain embodiments, "about" refers to +/−0.4°. In certain embodiments, "about" refers to +/−0.3°. In certain embodiments, "about" refers to +/−0.2°. In certain embodiments, "about" refers to +/−0.1°.

In certain embodiments, two or more peaks in its powder X-ray diffraction pattern are selected from those at at about 6.8°, about 9.4°, about 11.5°, about 13.6°, about 15.3°, about 17.0°, about 19.3°, about 20.2°, about 21.5°, about 22.3°, about 23.0°, about 25.2°, and about 29.4° 2-theta.

In certain embodiments, three or more peaks in its powder X-ray diffraction pattern are selected from those at at about 6.8°, about 9.4°, about 11.5°, about 13.6°, about 15.3°, about 17.0°, about 19.3°, about 20.2°, about 21.5°, about 22.3°, about 23.0°, about 25.2°, and about 29.4° 2-theta.

In certain embodiments, substantially all of the peaks in its powder X-ray diffraction pattern are selected from those at at about 6.8°, about 9.4°, about 11.5°, about 13.6°, about 15.3°, about 17.0°, about 19.3°, about 20.2°, about 21.5°, about 22.3°, about 23.0°, about 25.2°, and about 29.4° 2-theta.

In certain embodiments, substantially all of the peaks in its powder X-ray diffraction pattern are selected from those at about: 6.8°, 9.4°, 11.5°, 13.6°, 15.3°, 17.0°, 19.3°, 20.2°, 21.5°, 22.3°, 23.0°, 25.2°, 29.4° (2θ, ld.p).

In various embodiments, Form D has a powder X-ray diffraction pattern substantially similar to that depicted in FIG. 1.

In various embodiments, Form D has a water content of about 2-4% w/w. In various embodiments, Form D has a water content of about 1-3% w/w. In various embodiments, Form D has a water content of about 1%, 2.1%, or 2.5% w/w.

In certain embodiments, Form D is a hydrate comprising 0.1, 0.2, 0.3, 0.4, 0.5, 0.6, 0.7, 0.8, 0.9, or 1 equivalents of water. In various embodiments, Form D is a hydrate comprising 0.1 equivalents of water. In various embodiments, Form D is a hydrate comprising 0.2 equivalents of water. In various embodiments, Form D is a hydrate comprising 0.3 equivalents of water. In various embodiments, Form D is a hydrate comprising 0.4 equivalents of water. In various embodiments, Form D is a hydrate comprising 0.5 equivalents of water. In various embodiments, Form D is a hydrate comprising 0.6 equivalents of water. In various embodiments, Form D is a hydrate comprising 0.7 equivalents of water. In various embodiments, Form D is a hydrate comprising 0.8 equivalents of water. In various embodiments, Form D is a hydrate comprising 0.9 equivalents of water.

In certain aspects, the invention provides a composition comprising a crystalline form of Compound 1 selected from the group consisting of Form A of Compound 1 as described above, Form B of Compound 1 as described above, Form C of Compound 1 as described above, Form D of Compound 1 as described above, and combinations thereof.

In certain embodiments, the composition comprises Form A of Compound 1 as described above, wherein Form A constitutes greater than 95% by weight of the composition. In certain embodiments, the Form A constitutes greater than 99% by weight of the composition.

In certain embodiments, the composition further comprises any one or more of Form B, Form C, Form D, or amorphous Compound 1.

In certain embodiments, the composition further comprises a pharmaceutically acceptable carrier.

In certain aspects, the invention provides an oral formulation comprising the composition of the invention.

In certain aspects, the invention provides an isolated composition of Form A of Compound 1. In certain aspects, the invention provides an isolated composition of Form B of Compound 1. In certain aspects, the invention provides an isolated composition of Form C of Compound 1. In certain aspects, the invention provides an isolated composition of Form D of Compound 1.

In various aspects, the invention provides a method of producing polymorph Form A of Compound 1, comprising the steps of:
(a) reacting Compound 2

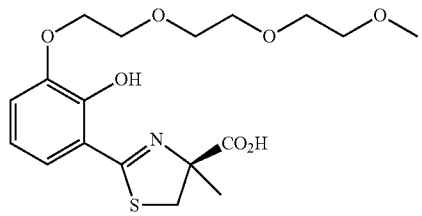

with NaOH in the presence of one or more solvents; and
(b) inducing crystallization;
wherein crystallization provides Form A of Compound 1.

In certain embodiments, the NaOH is an aqueous solution. In certain embodiments, the NaOH solution has a concentration of about 1-10 molar.

In various embodiments, the one or more solvents are selected from water, methanol, ethanol, i-PrOH (IPA), butanol, isoamyl alcohol, t-butanol, n-butanol, ethyl acetate, isopropyl acetate, acetone, methylethylketone, diethyl ether, TBME, 1,4-dioxane, THF, DMF, DMSO, acetonitrile, glyme, diglyme, toluene, benzene, dichloromethane, heptane, and hexane, and combinations thereof.

In certain embodiments, the solvents are water, ethanol or TBME or combinations thereof.

In certain embodiments, the solvents are water, ethanol and TBME in a volume ratio of 1:5:20.

In certain embodiments, the invention provides Polymorph Form A of Compound 1 produced by a method as described above.

In certain aspects, the invention provides a method of producing polymorph Form B of Compound 1, comprising the steps of:
(a) mixing Form A of Compound 1 with one or more solvents;
(b) heating up the mixture to about 30-50° C.; and
(c) inducing crystallization;
wherein crystallization provides polymorph Form B of Compound 1.

In certain embodiments, the one or more solvents are selected from water, methanol, ethanol, i-PrOH (IPA), butanol, isoamyl alcohol, t-butanol, n-butanol, ethyl acetate, isopropyl acetate, acetone, methylethylketone, diethyl ether, TBME, 1,4-dioxane, THF, DMF, DMSO, acetonitrile, glyme, diglyme, toluene, benzene, dichloromethane, heptane, and hexane.

In certain embodiments, the solvents are selected from ethyl acetate, isopropyl acetate, and IPA.

In certain embodiments, the solvents are IPA and water.

In certain embodiments, the solvents are IPA and water in a volume ratio of 50:1.

In various embodiments, in step (b) the mixture is heated to about 40-45° C.

In certain embodiments, the invention provides Polymorph Form B of Compound 1 produced by a method as described above.

In various aspects, the invention provides a method of producing polymorph Form C of Compound 1, comprising the steps of:
(a) dissolving Form A of Compound 1 in a first solvent;
(b) adding a second solvent; and
(c) inducing crystallization;
wherein crystallization provides polymorph Form C of Compound 1.

In certain embodiments, the first solvent is water, methanol, ethanol, i-PrOH (IPA), butanol, isoamyl alcohol, t-butanol, n-butanol, ethyl acetate, isopropyl acetate, acetone, methylethylketone, diethyl ether, TBME, 1,4-dioxane, THF, DMF, DMSO, acetonitrile, glyme, diglyme, toluene, benzene, dichloromethane, heptane, and hexane, and combinations thereof.

In various embodiments, the second solvent is water, methanol, ethanol, i-PrOH (IPA), butanol, isoamyl alcohol, t-butanol, n-butanol, ethyl acetate, isopropyl acetate, acetone, methylethylketone, diethyl ether, TBME, 1,4-dioxane, THF, DMF, DMSO, acetonitrile, glyme, diglyme, toluene, benzene, dichloromethane, heptane, and hexane.

In various embodiments, the invention provides Polymorph Form C of Compound 1 produced by a method as described above.

In certain aspects, the invention provides a method of producing polymorph Form D of Compound 1, comprising the step of drying Form A of Compound 1 under reduced pressure at elevated temperature, to provide polymorph Form D of Compound 1.

In certain embodiments, the reduced pressure is about 0.1 to about 0.4 atm.

In various embodiments, the elevated temperature ranges from about 40-80° C. In certain embodiments, the elevated temperature is about 60° C.

In various embodiments, the invention provides Polymorph Form D of Compound 1 produced by a method as described above.

In certain aspects, the invention provides a method for treating metal overload, comprising a step of administering to a subject in need of treatment a therapeutically effective amount of a crystalline form of Compound 1.

In various embodiments, the invention provides a method as described above wherein the crystalline form is Form A of Compound 1.

In various embodiments, the invention provides a method as described above wherein the crystalline form of Compound 1 is administered orally.

In various embodiments, the invention provides a method as described above wherein the metal overload is uranium overload.

In various embodiments, the invention provides a method as described above wherein the metal overload is iron overload. In certain embodiments, the iron overload is transfusional iron overload. In certain embodiments, the iron overload is caused by increased iron absorption.

In various embodiments, the invention provides a method as described above wherein the subject is suffering from β-thalassemia-intermediate, β-thalassemia-major, non-transfusion dependent Thalassaemia (NTDT), Blackfan-Diamond anemia, Sideroblastic anemia, sickle cell disease, aplastic anemia, red cell aplasia, Myelodysplasia (MDS), chronic myelofibrosis, paroxysmal nocturnal hemoglobinuria, off-therapy leukemia, hereditary hemochromatosis, or porphyria cutanea tarda. In certain embodiments, the subject is suffering from β-thalassemia-intermediate. In certain embodiments, the subject is suffering from β-thalassemia-major. In certain embodiments, the subject is suffering from sickle cell disease. In certain embodiments, the subject is suffering from Myelodysplasia (MDS).

In various embodiments, the invention provides a method as described above wherein the subject is an adult.

In various embodiments, the invention provides a method as described above wherein the subject is a pediatric patient.

DETAILED DESCRIPTION OF THE INVENTION

Figure 1:
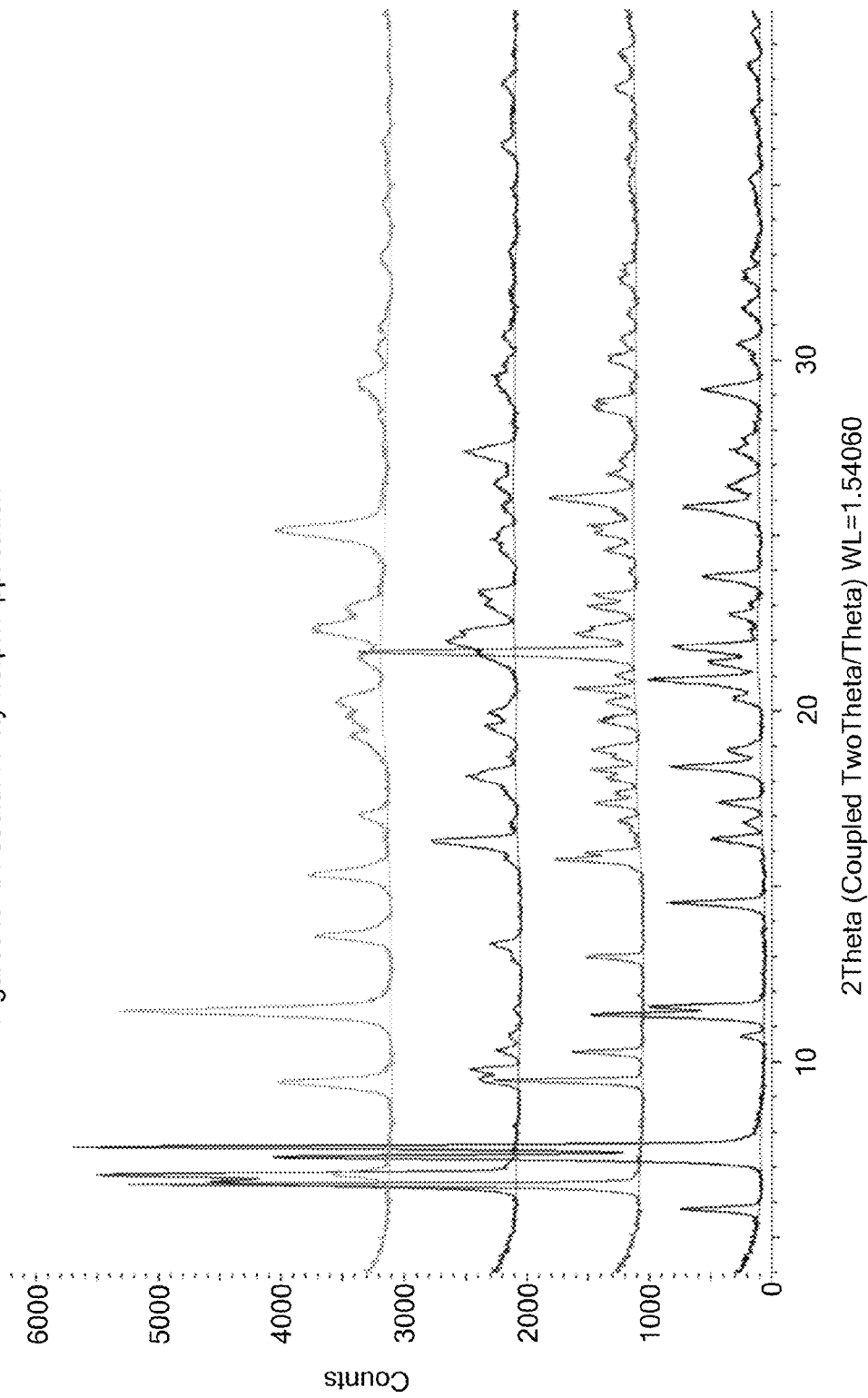
FIG. 1. Four forms of 1 identified by XRPD: Form A, Form B, Form C, and Form D.

General Description of Certain Aspects of the Invention:

In certain aspects, the invention provides for salts, polymorphs, solvates, and hydrates, of compounds of Formula I:

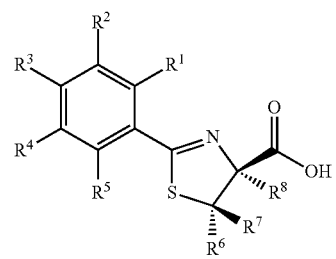

wherein:

$R^1$, $R^2$, $R^3$, $R^4$, and $R^5$ are independently chosen from hydrogen, hydroxy, alkyl, arylalkyl, alkoxy, and $CH_3O$ $((CH_2)_n—O)_m—$, any of which may be optionally substituted;

$R^6$, $R^7$, and $R^8$ are independently chosen from hydrogen, halogen, hydroxy, lower alkyl, and lower alkoxy;

m is an integer from 0 to 8; and n is an integer from 0 to 8.

In some embodiments, $R^1$ is OH, or a salt thereof.

In some embodiments, $R^2$ is $CH_3O((CH_2)_n—O)_m—$. In some embodiments, $R^2$ is $CH_3O((CH_2)_n—O)_m—$, n is 2 and m is 3.

In some embodiments, $R^3$ is $CH_3O((CH_2)_n—O)_m—$. In some embodiments, $R^3$ is $CH_3O((CH_2)_n—O)_m—$, n is 2 and m is 3.

In some embodiments, $R^2$ or $R^3$ is $CH_3O((CH_2)_n—O)_m—$. In some embodiments, $R^2$ or $R^3$ is $CH_3O((CH_2)_n—O)_m—$, n is 2 and m is 3.

In some embodiments, the invention provides a salt, polymorph, solvate, or hydrate of a compound of Formula I: 3'-desazadesferrithiocin polyether.

In certain embodiments, salts of Formula I are solid.

In further embodiments, salts of Formula I are crystalline.

In further embodiments, salts of Formula I are amorphous.

It will be appreciated that where the present disclosure refers to a compound of Formula I, salts and polymorphs of a compound of Formula I are also included.

In some embodiments, compounds disclosed herein are salts, polymorphs, solvates, and hydrates thereof having structural Formula II:

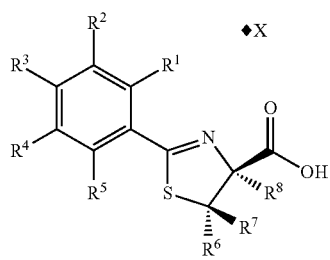

II wherein:

X is a counterion; and each of $R^1$, $R^2$, $R^3$, $R^4$, $R^5$, $R^6$, $R^7$, and $R^8$ are as defined above and described in classes and subclasses herein, both singly and in combination.

As used herein, the phrase "X is a counterion" may be inferred and a corresponding charges on each moiety be assumed to be present or absent. For example, if X is one or more monovalent cation such as $Na^{2+}$, it may be inferred that the coupled compound has lost a two protons to form an ionic bond with X, despite the formulae being drawn to explicitly show all protons in place. Similarly, when X is an anion, the coupled compound takes on cationic character. As used herein, the term counterion encompasses all possible placement where on a compound a counterion has bound and ratios of charges. Additionally, counterions and compounds may combine in uneven molar ratios to form solid salts. As those of skill in the art will recognize, different ratios of counterions may form stable arrangements and solid forms, including 1:1, 2:1, and 3:1 based on preferred oxidation states of each ion, salt formation conditions (including solvent), etc. All such forms are contemplated here.

In certain embodiments, $R^8$ is chosen from hydrogen and methyl.

In further embodiments, $R^6$ and $R^7$ are independently chosen from hydrogen and methoxy.

In further embodiments, $R^1$ is hydroxyl, or a salt thereof.

In further embodiments, $R^2$, $R^3$, $R^4$, and $R^5$ are independently chosen from hydrogen and $CH_3O((CH_2)_n-O)_m-$.

In certain embodiments, salts of Formula II are solid.

In further embodiments, salts of Formula II are crystalline.

In certain embodiments, the counterion X of Formula II are one or more monovalent cations selected from lithium, dilithium, sodium, disodium, potassium and dipotassium. In certain embodiments, the counterion X of Formula II is chosen from lysine, N-methyl-D-glucamine (NMG), tromethamine, calcium, zinc, and piperazine. In some embodiments, X includes one or more metal cations and optionally, as required by charge, an anion such as halide, carbonate, bicarbonate, hydroxide, carboxylate, sulfate, bisulfate, phosphate, nitrate, alkoxy having from 1 to 6 carbon atoms, sulfonate, and aryl sulfonate (e.g., $MgOH^+$).

In further embodiments, salts, polymorphs, solvates, and hydrates thereof have structural formula III:

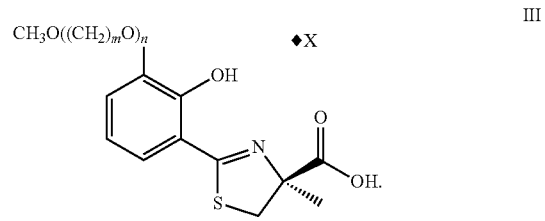

III

In further embodiments, salts, polymorphs, solvates, and hydrates thereof have structural formula IIIa:

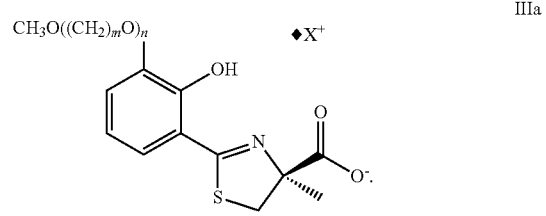

IIIa

In certain embodiments, the salts, polymorphs, solvates, and hydrates thereof have structural formula IIIb:

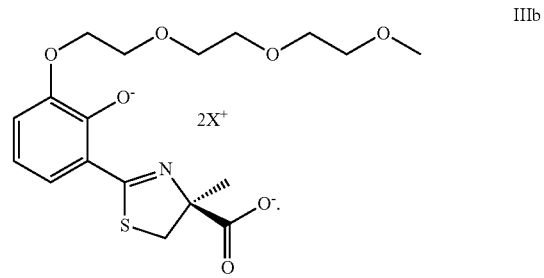

IIIb

In certain embodiments, salts of Formula III, IIIa, and IIIb are solid.

In further embodiments, salts of Formula III, IIIa, and IIIb are crystalline.

In further embodiments, salts of Formula III, IIIa, and IIIb are amorphous.

In further embodiments, each counterion X is independently chosen from calcium, magnesium, potassium, dipotassium, sodium, di-sodium, zinc, and piperazine, and optionally as required by charge, includes an anion (e.g., $MgOH^+$). Exemplary such anions include, without limitation, halide, carbonate, bicarbonate, hydroxide, carboxylate, sulfate, bisulfate, phosphate, nitrate, alkoxy having from 1 to 6 carbon atoms, sulfonate, and aryl sulfonate.

In further embodiments, m is 2 and n is 3.

In further embodiments, the salt is the disodium salt, or a polymorph, solvate, or hydrate thereof.

In further embodiments, the salt is (S)-2-(2-hydroxy-3-(2-(2-(2-methoxyethoxy)ethoxy)ethoxy)phenyl)-4-methyl-4,5-dihydrothiazole-4-carboxylate disodium or a polymorph, solvate, or hydrate thereof.

In certain embodiments, salts and polymorphs thereof have structural formula IV:

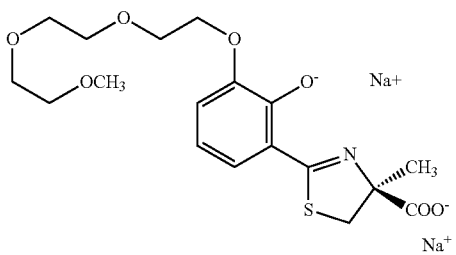

IV or, equivalently, (S)-2-(2-hydroxy-3-(2-(2-(2-methoxyethoxy)ethoxy)ethoxy)phenyl)-4-methyl-4,5-dihydrothiazole-4-carboxylate disodium.

In certain embodiments, salts of any Formulae herein IV are solid.

In further embodiments, salts of any Formula herein IV are crystalline.

In other embodiments, a suitable salt according to the present invention is (S)-2-(2-hydroxy-3-(2-(2-(2-methoxyethoxy)ethoxy)ethoxy)phenyl)-4-methyl-4,5-dihydrothiazole-4-carboxylate disodium Form A polymorph.

In other embodiments, a suitable salt according to the present invention is (S)-2-(2-hydroxy-3-(2-(2-(2-methoxyethoxy)ethoxy)ethoxy)phenyl)-4-methyl-4,5-dihydrothiazole-4-carboxylate disodium Form B polymorph.

In other embodiments, a suitable salt according to the present invention is (S)-2-(2-hydroxy-3-(2-(2-(2-methoxyethoxy)ethoxy)ethoxy)phenyl)-4-methyl-4,5-dihydrothiazole-4-carboxylate disodium Form C polymorph.

In other embodiments, a suitable salt according to the present invention is (S)-2-(2-hydroxy-3-(2-(2-(2-methoxyethoxy)ethoxy)ethoxy)phenyl)-4-methyl-4,5-dihydrothiazole-4-carboxylate disodium Form D polymorph.

In certain embodiments, the above polymorphs include solvates and hydrates thereof.

In certain embodiments, the invention provides a solid form of Compound 1:

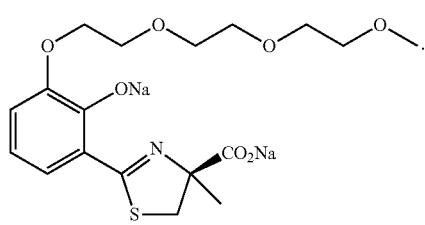

1

In certain embodiments, the solid form is crystalline.

In various embodiments, the solid form is Form A. In various embodiments, the solid form is Form B. In various embodiments, the solid form is Form C. In various embodiments, the solid form is Form D. In various embodiments, the solid form is amorphous. In certain embodiments, the solid form is a solvate. In certain embodiments, the solid form is a hydrate.

In various embodiments, the solid form is an isolated Form A. In various embodiments, the solid form is an isolated Form B. In various embodiments, the solid form is an isolated Form C. In various embodiments, the solid form is an isolated Form D.

It would be desirable to provide a solid form of Compound 1 that, as compared to Compound 1, imparts characteristics such as improved aqueous solubility, stability and ease of formulation. Accordingly, the present invention provides several solid forms and polymer forms of Compound 1.

Exemplary solid forms are described in more detail below.

In other embodiments, the present invention provides Compound 1 substantially free of impurities. As used herein, the term "substantially free of impurities" means that the compound contains no significant amount of extraneous matter. Such extraneous matter may include starting materials, residual solvents, or any other impurities that may result from the preparation of, and/or isolation of, Compound 1. In certain embodiments, at least about 80% by weight of Compound 1 is present. In certain embodiments, at least about 85% by weight of Compound 1 is present. In certain embodiments, at least about 90% by weight of Compound 1 is present. In certain embodiments, at least about 95% by weight of Compound 1 is present. In certain embodiments, at least about 93% by weight of Compound 1 is present. In still other embodiments of the invention, at least about 99% by weight of Compound 1 is present. In certain embodiments, the extraneous matter is water.

According to one embodiment, Compound 1 is present in an amount of at least about 80, 85, 90, 92, 93, 94, 95, 96, 97, 97.5, 98.0, 98.5, 99, 99.5, or 99.8 weight percent where the percentages are based on the total weight of the composition. According to another embodiment, Compound 1 contains no more than about 3.0 area percent HPLC of total organic impurities and, in certain embodiments, no more than about 1.5 area percent HPLC total organic impurities relative to the total area of the HPLC chromatogram. In other embodiments, Compound 1 contains no more than about 8.0 area percent HPLC of any single impurity; no more than about 7.0 area percent HPLC of any single impurity, no more than about 5.0 area percent HPLC of any single impurity, no more than about 2.0 area percent HPLC of any single impurity, no more than about 1.0 area percent HPLC of any single impurity, no more than about 0.6 area percent HPLC of any single impurity, and, in certain embodiments, no more than about 0.5 area percent HPLC of any single impurity, relative to the total area of the HPLC chromatogram.

The structure depicted for Compound 1 is also meant to include all tautomeric forms of Compound 1. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

Solid Forms of Compound 1:

It has been found that Compound 1 can exist in a variety of solid forms. Such forms include polymorphs and amorphous forms. The solid forms can be solvates, hydrates and unsolvated forms of Compound 1. All such forms are contemplated by the present invention. In certain embodiments, the present invention provides Compound 1 as a mixture of one or more solid forms of Compound 1.

As used herein, the term "polymorph" refers to the different crystal structures (of solvated or unsolvated forms) in which a compound can crystallize.

As used herein, the term "solvate" refers to a solid form with either a stoichiometric or non-stoichiometric amount of solvent (e.g., a channel solvate). For polymorphs, the solvent is incorporated into the crystal structure. Similarly, the term "hydrate" refers to a solid form with either a stoichiometric or non-stoichiometric amount of water. For polymorphs, the water is incorporated into the crystal structure.

As used herein, the term "about", when used in reference to a degree 2-theta value refers to the stated value ±0.3 degree 2-theta. In certain embodiments, "about" refers to ±0.2 degree 2-theta or ±0.1 degree 2-theta.

In certain embodiments, Compound 1 is a crystalline solid. In other embodiments, Compound 1 is a crystalline solid substantially free of amorphous Compound 1. As used herein, the term "substantially free of amorphous Compound 1" means that the compound contains no significant amount of amorphous Compound 1. In certain embodiments, at least about 95% by weight of crystalline Compound 1 is present. In still other embodiments of the invention, at least about 97%, 98% or 99% by weight of crystalline compound 1 is present.

In certain embodiments, Compound 1 is a mesophase (liquid crystal).

In certain embodiments, Compound 1 is an amorphous material.

In certain embodiments, Compound 1 is a solvated crystal.

In certain embodiments, Compound 1 is a solvated crystal form. In certain embodiments, the water is present in an amount ranging from approximately 6-8 wt %, or in certain embodiments approximately 5-7.5 wt %, or in certain embodiments approximately 4-6 wt %, or in certain embodiments, approximately 1-4 wt %.

In some embodiments, the present invention provides a polymorphic form of Compound 1 referred to herein as Form A.

In certain embodiments, the present invention provides Form A of Compound 1. According to one embodiment, Form A of Compound 1 is characterized in that it has one or more peaks in its powder X-ray diffraction pattern selected from those at about 5.8°, about 7.3°, about 7.6°, about 10.7°, about 11.3°, about 11.6°, about 14.6°, about 16.4°, about 16.8°, about 17.3°, about 18.4°, about 18.9°, about 20.4°, about 20.9°, about 21.4°, about 21.8°, about 23.8°, about 25.8°, about 26.4°, about 27.5°, about 29.1°, about 30.3°, about 31.4°, and about 32.4° 2-theta. In some embodiments, Form A of Compound 1 is characterized in that it has two or more peaks in its powder X-ray diffraction pattern selected from those at about 5.8°, about 7.3°, about 7.6°, about 10.7°, about 11.3°, about 11.6°, about 14.6°, about 16.4°, about 16.8°, about 17.3°, about 18.4°, about 18.9°, about 20.4°, about 20.9°, about 21.4°, about 21.8°, about 23.8°, about 25.8°, about 26.4°, about 27.5°, about 29.1°, about 30.3°, about 31.4°, and about 32.4° 2-theta. In certain embodiments, Form A of Compound 1 is characterized in that it has three or more peaks in its powder X-ray diffraction pattern selected from those at about 5.8°, about 7.3°, about 7.6°, about 10.7°, about 11.3°, about 11.6°, about 14.6°, about 16.4°, about 16.8°, about 17.3°, about 18.4°, about 18.9°, about 20.4°, about 20.9°, about 21.4°, about 21.8°, about 23.8°, about 25.8°, about 26.4°, about 27.5°, about 29.1°, about 30.3°, about 31.4°, and about 32.4° 2-theta. In particular embodiments, Form A of Compound 1 is characterized in having substantially all of the peaks in its X-ray powder diffraction pattern selected from those at about 5.8°, about 7.3°, about 7.6°, about 10.7°, about 11.3°, about 11.6°, about 14.6°, about 16.4°, about 16.8°, about 17.3°, about 18.4°, about 18.9°, about 20.4°, about 20.9°, about 21.4°, about 21.8°, about 23.8°, about 25.8°, about 26.4°, about 27.5°, about 29.1°, about 30.3°, about 31.4°, and about 32.4° 2-theta.

According to one aspect, Form A of Compound 1 has a powder X-ray diffraction pattern substantially similar to that depicted in FIG. 1.

In certain embodiments, Form A of Compound 1 is characterized in that it has one or more peaks in its FT-IR spectrum at about 3502.5, about 3243.9, about 2924.2, about 2897.7, about 1652.2, about 1574.1, about 1450.3, about 1396.0, about 1356.3, about 1316.6, about 1245.8, about 1212.9, about 1086.1, about 1032.9, about 945.0, about 910.0, about 831.9, about 789.3, and about 722.8 cm$^{-1}$.

Figure 2:
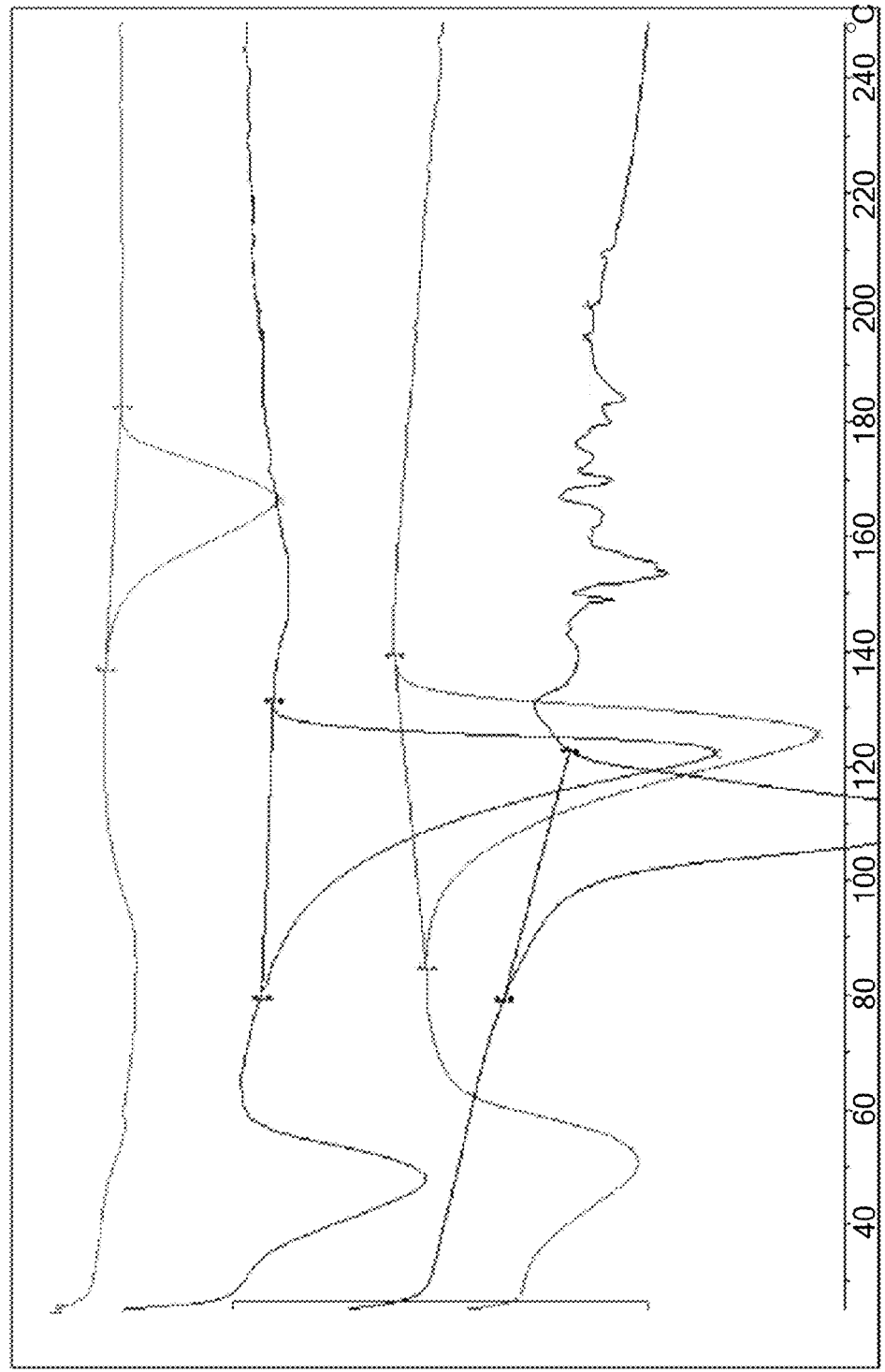
FIG. 2. Four forms of 1 identified by DSC: Form A, Form B, Form C, and Form D.
Figure 3:
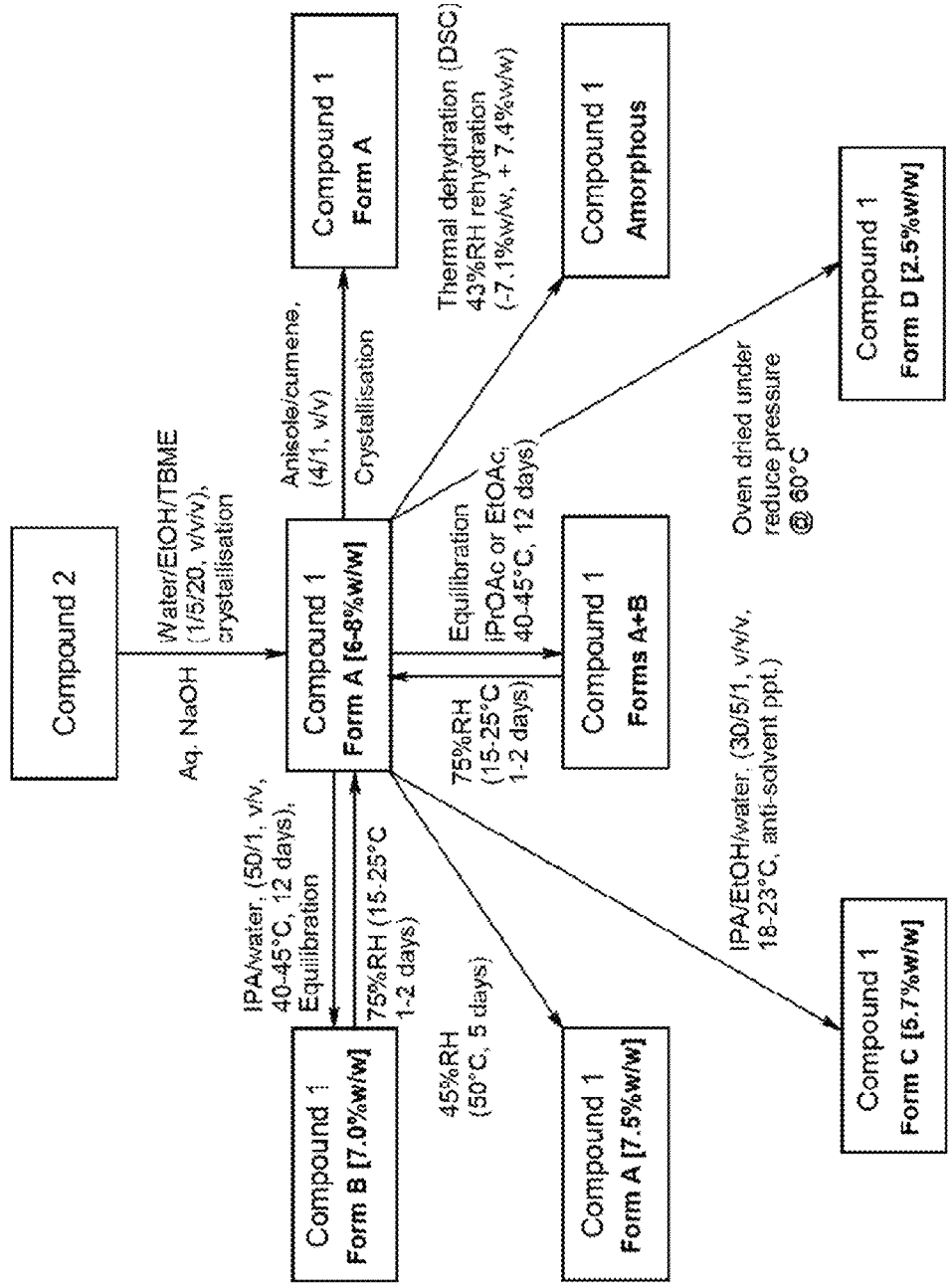
FIG. 3. Relationships between Form A, Form B, Form C, and Form D, by water content.
Figure 4:
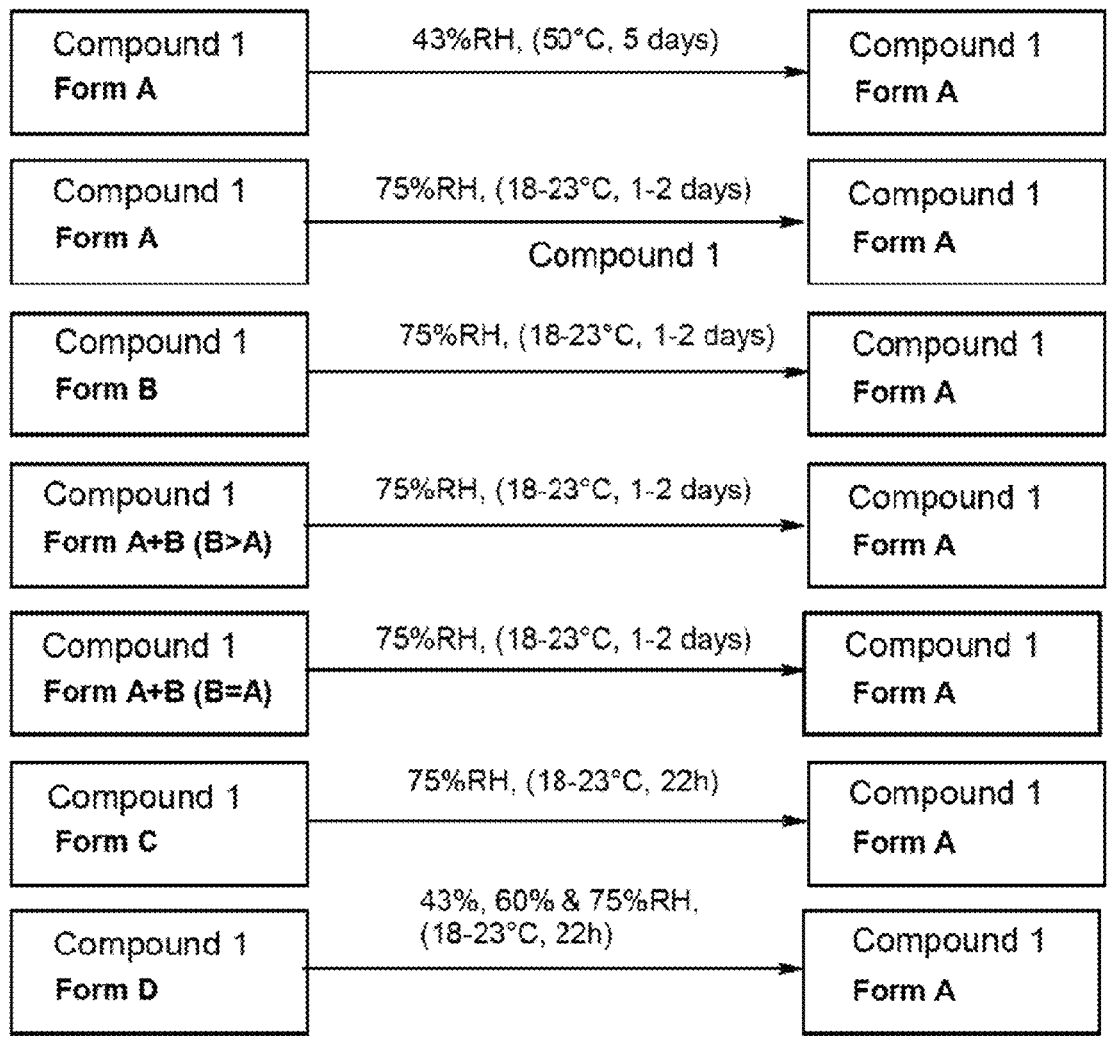
FIG. 4. Change in forms after exposure to humid conditions.
Figure 5:
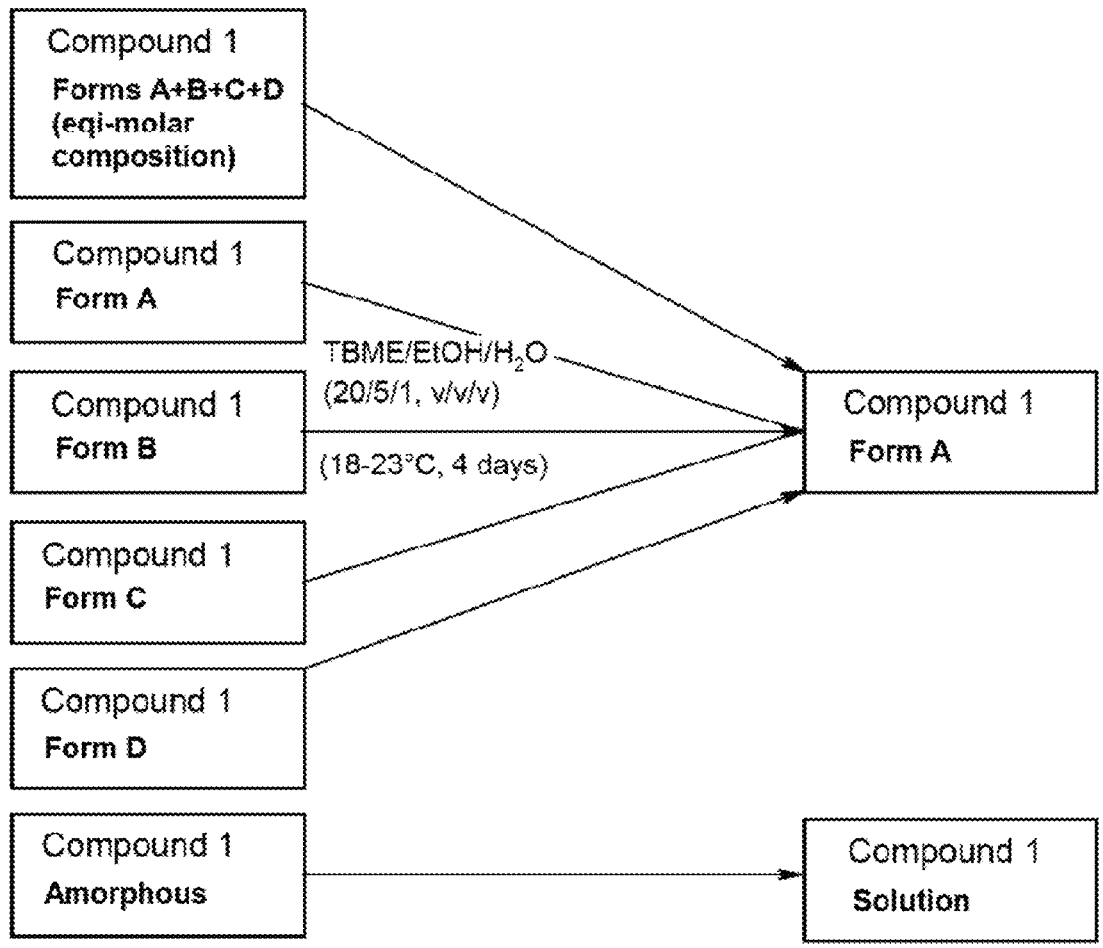
FIG. 5. Change in forms after stirring in original isolation solvents.
Figure 6:
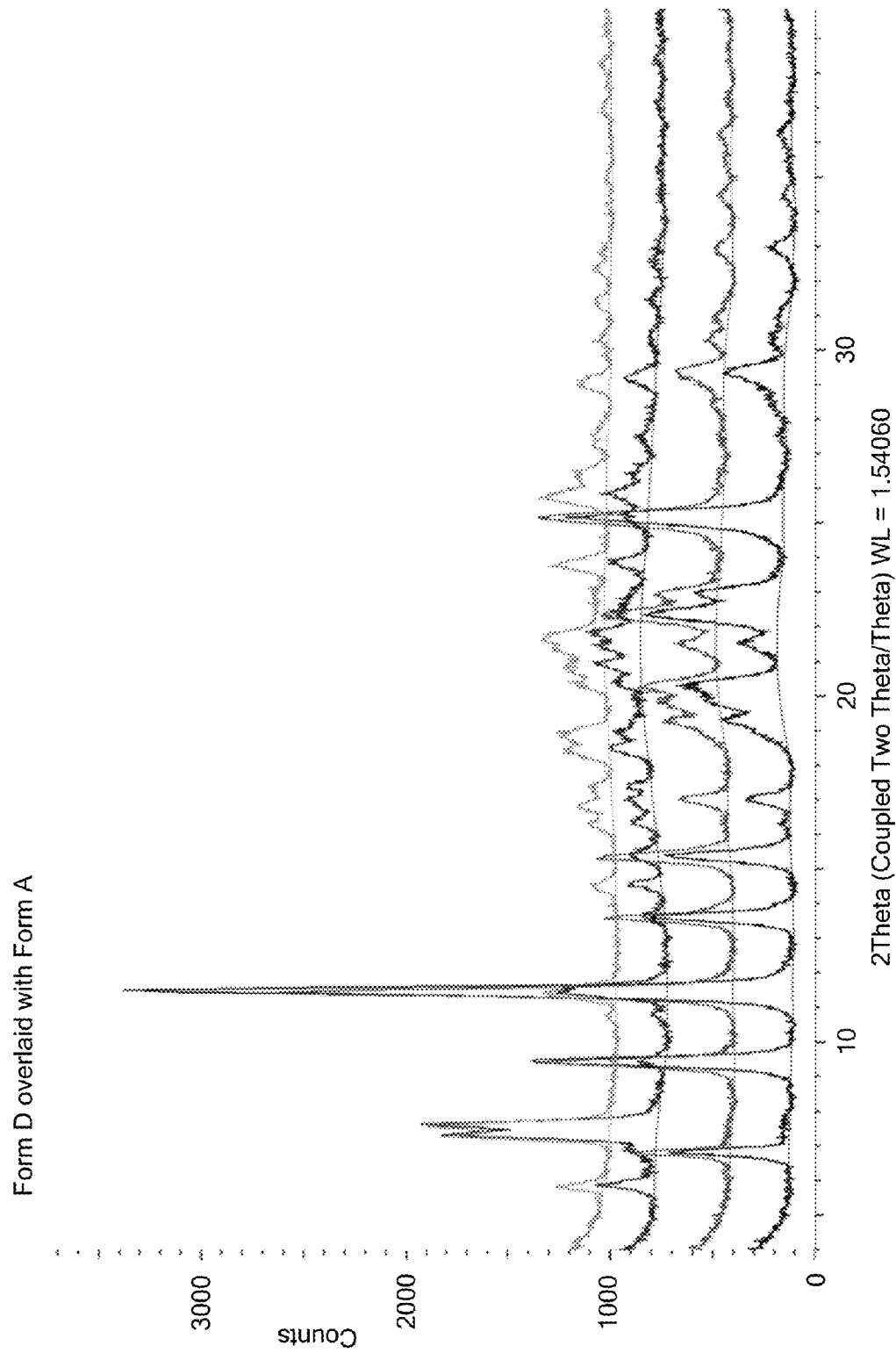
FIG. 6. XRPD diffractograms of Form D overlaid with Form A.
Figure 7:
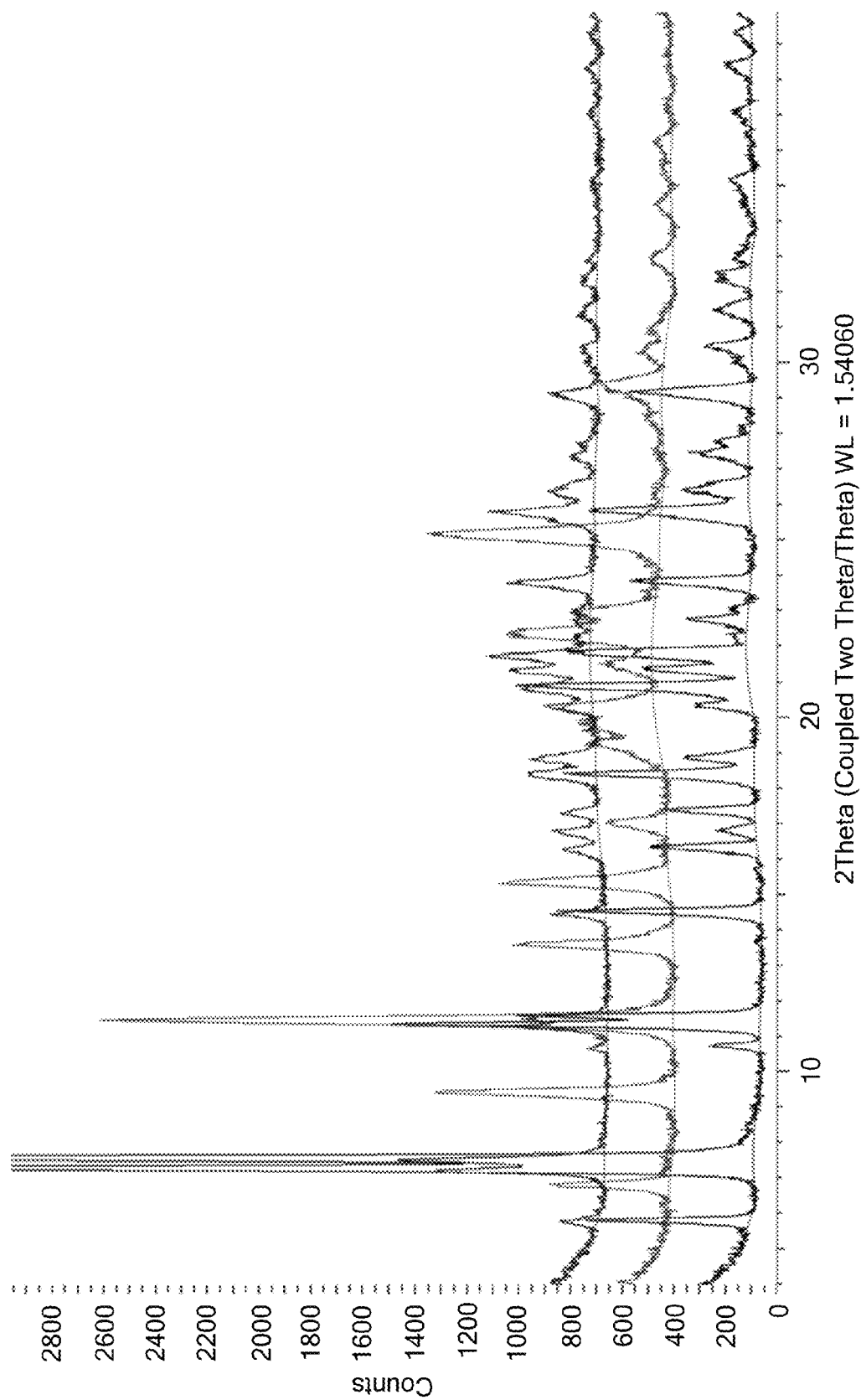
FIG. 7. XRPD diffractograms of the conversion from Form A to Form D to Form A.
Figure 8:
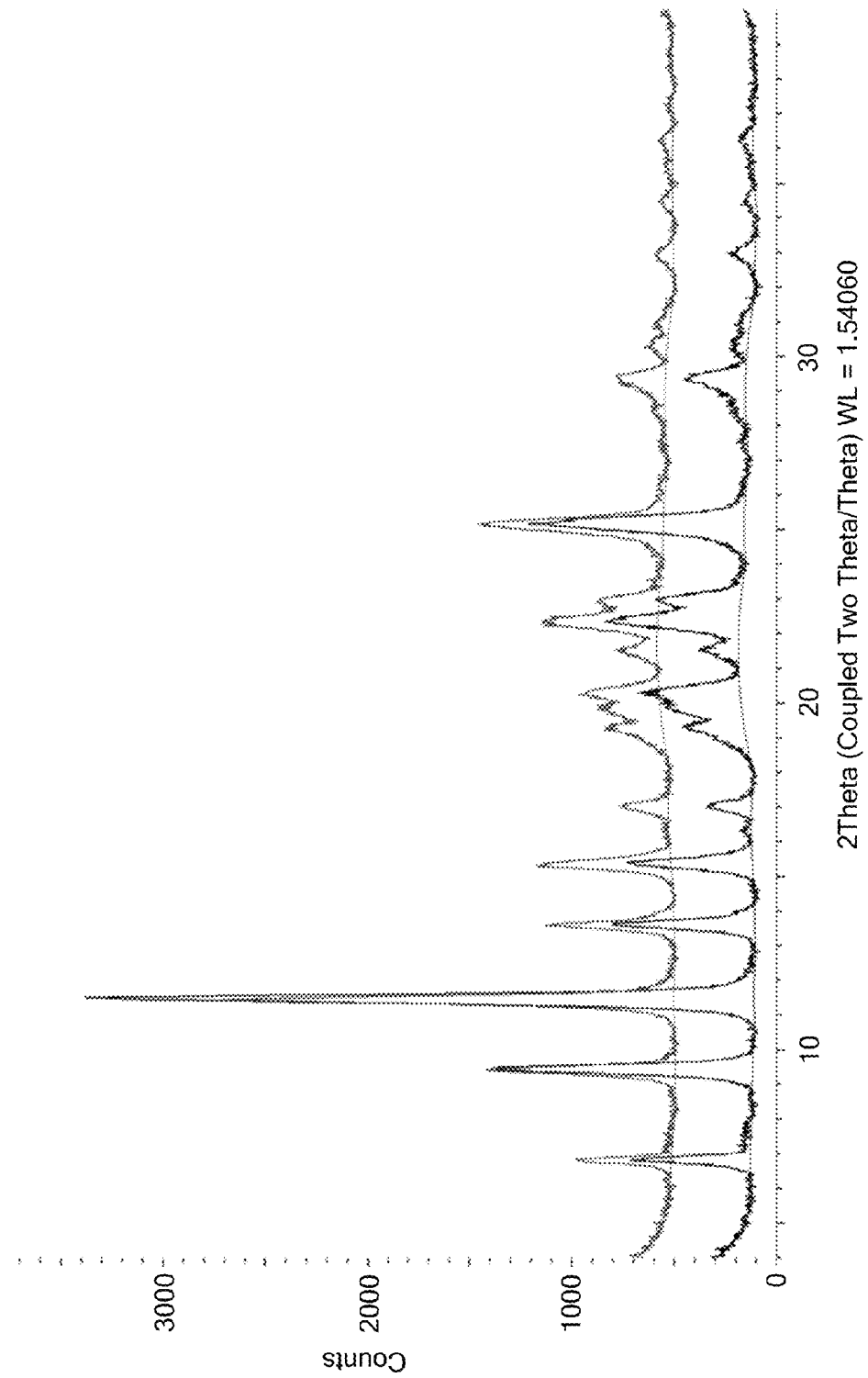
FIG. 8. XRPD diffractograms of Form D.
Figure 9:
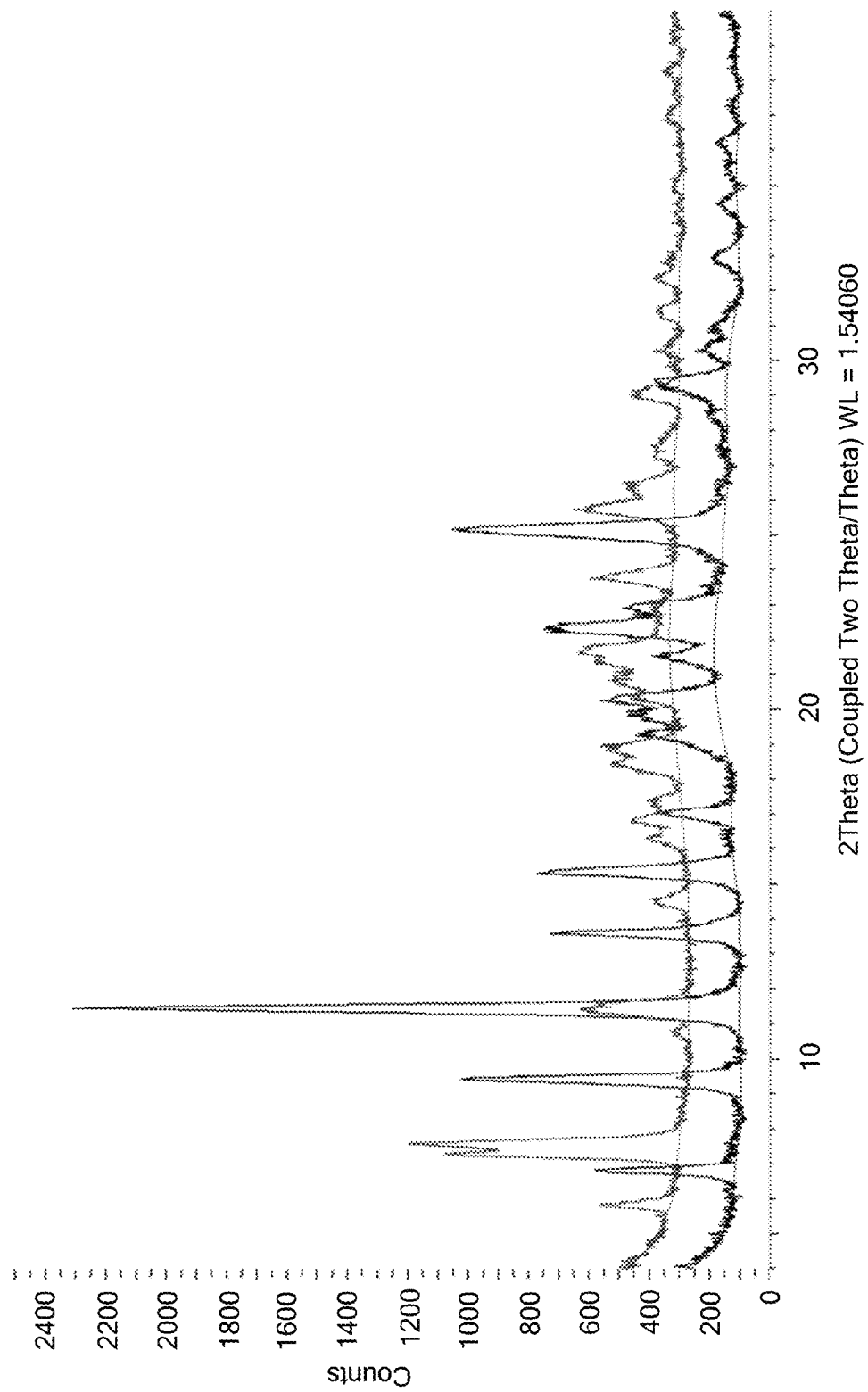
FIG. 9. XRPD diffractograms of the conversion from Form A to Form D.
Figure 10:
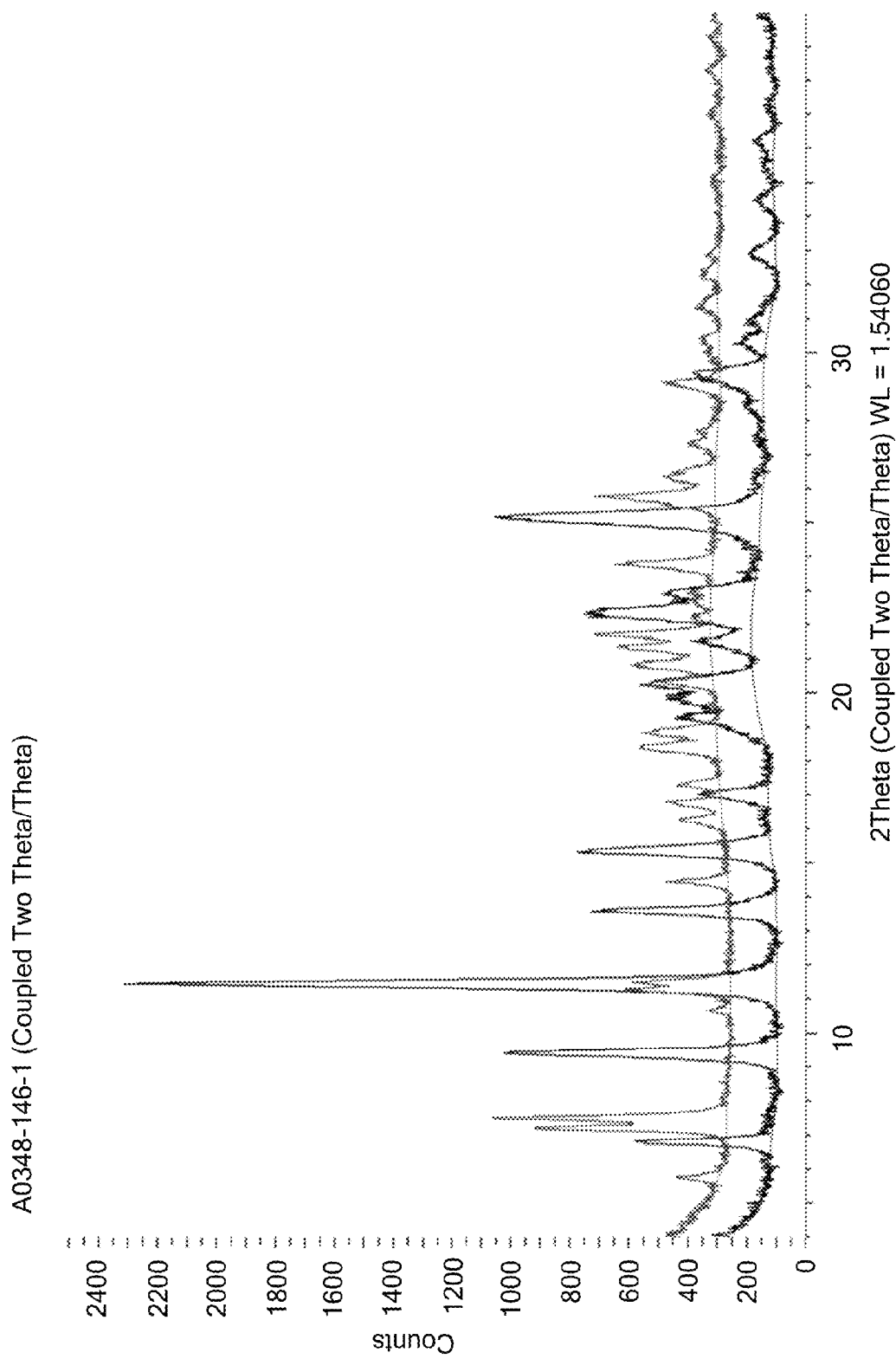
FIG. 10. XRPD diffractograms of the conversion from Form D to Form A.
Figure 11:
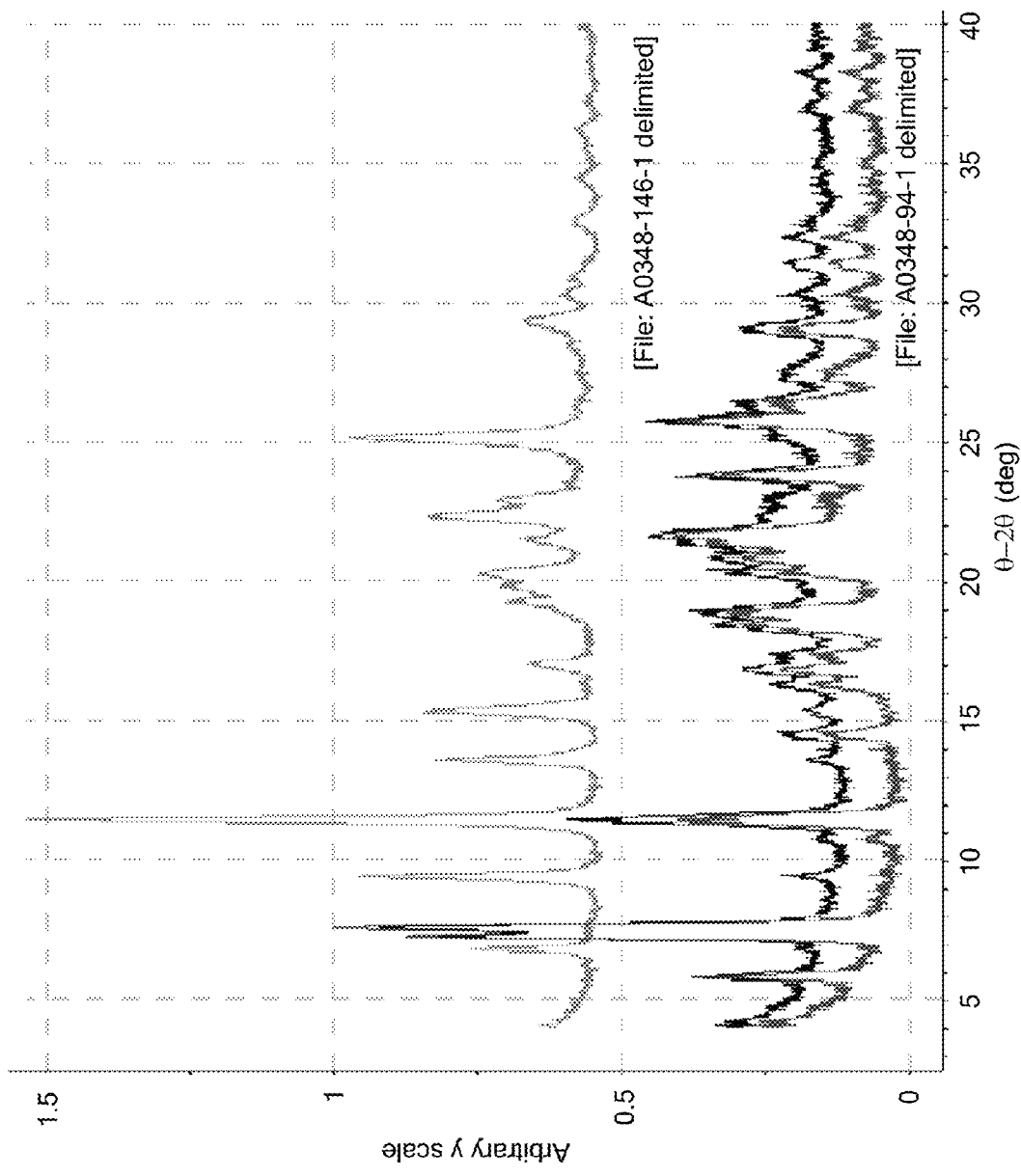
FIG. 11. Computational estimate of XRPD diffractograms of the conversion from Form A to Form D.
Figure 12:
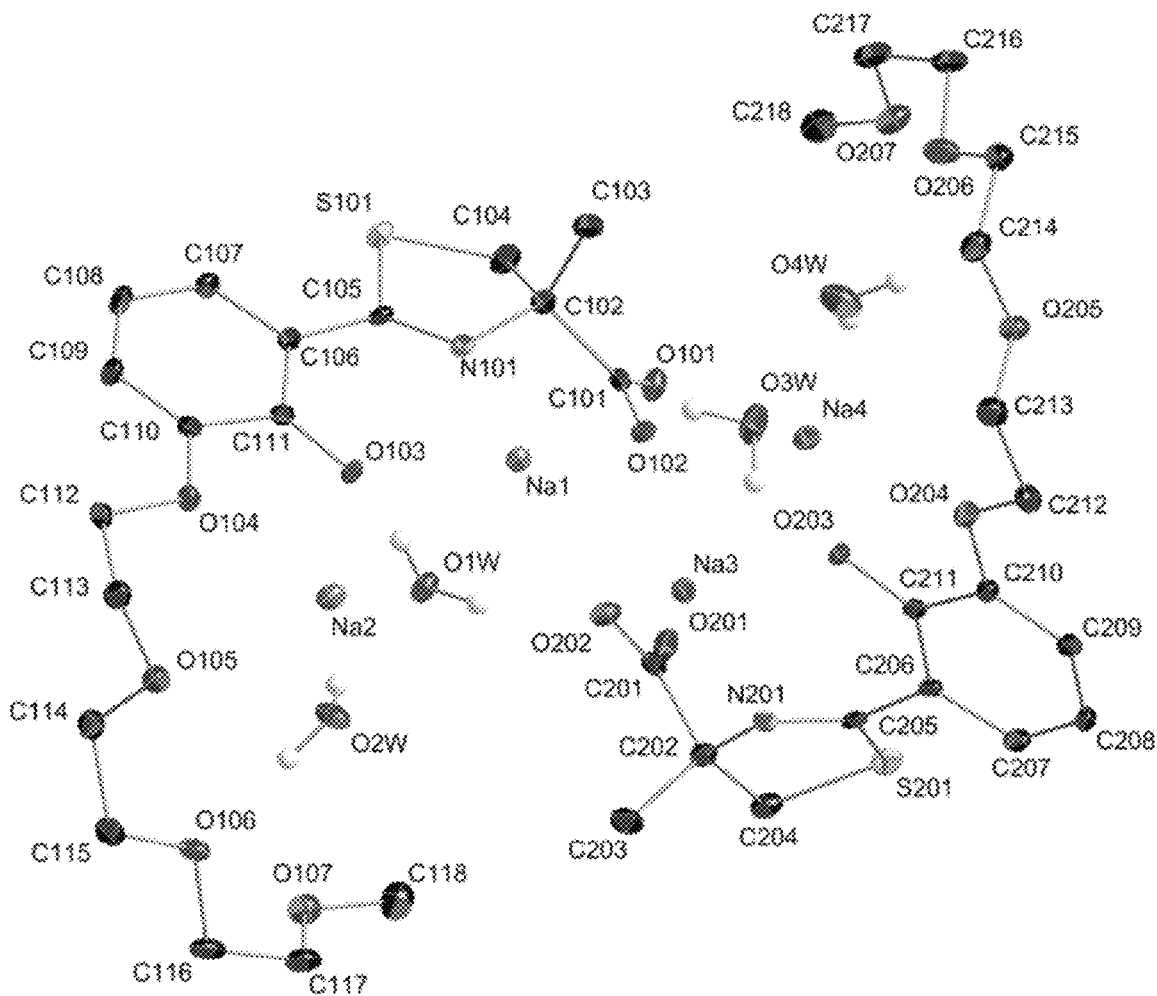
FIG. 12. Form A: Thermal ellipsoids drawn at the 35% probability level, selected hydrogens and Na—O bonds omitted for clarity.
Figure 13:
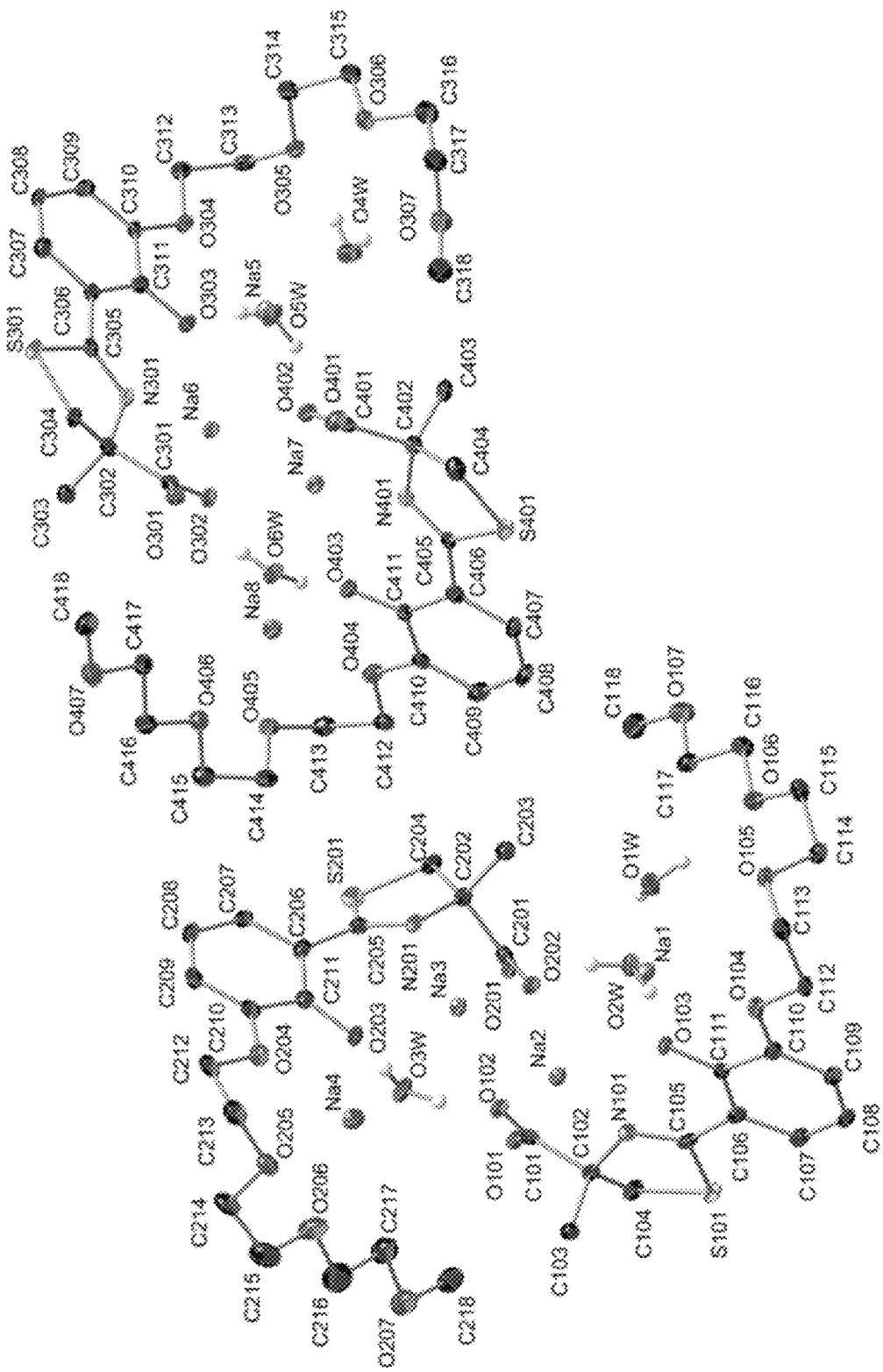
FIG. 13. Form B: Thermal ellipsoids drawn at the 35% probability level, selected hydrogens omitted for clarity.

In certain embodiments, Form A of Compound 1 is characterized in that it has one or more peaks in its DSC diffractogram at about 109.60° C. In certain embodiments, the peak has an onset of about 99.9° C., endset of about 119.1° C., and ∫normalised−84.2 Jg$^{-1}$. According to one aspect, Form A of Compound 1 has a DSC diffractogram pattern substantially similar to that depicted in FIG. 2.

In certain embodiments, Form A of Compound 1 is characterized in that it has a water content (KF) of 7.5% w/w.

In some embodiments, the present invention provides a polymorphic form of Compound 1 referred to herein as Form B.

In certain embodiments, the present invention provides Form B of Compound 1. According to another embodiment, Form B of Compound 1 is characterized in that it has one or more peaks in its powder X-ray diffraction pattern selected from those at about 6.6°, about 9.5°, about 10.3°, about 13.1°, about 15.8°, about 16.0°, about 17.4°, about 18.2°, about 18.9°, about 19.8°, about 20.3°, about 20.7°, about 21.1°, about 21.7°, about 22.2°, about 23.0°, about 23.3°, about 24.6°, about 25.2°, about 26.2°, about 26.8°, about 27.2°, about 28.7°, and about 30.0° 2-theta. In some embodiments, Form B of Compound 1 is characterized in that it has two or more peaks in its powder X-ray diffraction pattern selected from those at about 6.6°, about 9.5°, about 10.3°, about 13.1°, about 15.8°, about 16.0°, about 17.4°, about 18.2°, about 18.9°, about 19.8°, about 20.3°, about 20.7°, about 21.1°, about 21.7°, about 22.2°, about 23.0°, about 23.3°, about 24.6°, about 25.2°, about 26.2°, about 26.8°, about 27.2°, about 28.7°, and about 30.0° 2-theta. In certain embodiments, Form B of Compound 1 is characterized in that it has three or more peaks in its powder X-ray diffraction pattern selected from those at ab about 6.6°, about 9.5°, about 10.3°, about 13.1°, about 15.8°, about 16.0°, about 17.4°, about 18.2°, about 18.9°, about 19.8°, about 20.3°, about 20.7°, about 21.1°, about 21.7°, about 22.2°, about 23.0°, about 23.3°, about 24.6°, about 25.2°, about 26.2°, about 26.8°, about 27.2°, about 28.7°, and about 30.0° 2-theta. In particular embodiments, Form B of Compound 1 is characterized in having substantially all of the peaks in its X-ray powder diffraction pattern selected from those at about 6.6°, about 9.5°, about 10.3°, about 13.1°, about 15.8°, about 16.0°, about 17.4°, about 18.2°, about 18.9°, about 19.8°, about 20.3°, about 20.7°, about 21.1°, about 21.7°, about 22.2°, about 23.0°, about 23.3°, about 24.6°, about 25.2°, about 26.2°, about 26.8°, about 27.2°, about 28.7°, and about 30.0° 2-theta.

According to one aspect, Form B of Compound 1 has a powder X-ray diffraction pattern substantially similar to that depicted in FIG. 1.

In certain embodiments, Form B of Compound 1 is characterized in that it has one or more peaks in its FT-IR spectrum at about 3488.4, about 3222.5, about 2922.0, about 2876.4, about 1575.0, about 1450.1, about 1396.3, about 1353.8, about 1316.5, about 1245.6, about 1213.7, about 1086.8, about 1025.3, about 944.9, about 906.8, about 822.0, about 789.4, and about 723.9 cm$^{-1}$.

In certain embodiments, Form B of Compound 1 is characterized in that it has one or more peaks in its DSC diffractogram at about 125.32° C. In certain embodiments, the peak has an onset of about 106.7° C., endset of about 132.7° C., and ƒnormalised–103.6 Jg$^{-1}$. According to one aspect, Form B of Compound 1 has a DSC diffractogram pattern substantially similar to that depicted in FIG. 2.

In certain embodiments, Form B of Compound 1 is characterized in that it has a water content (KF) of 7.0% w/w.

In some embodiments, the present invention provides a polymorphic form of Compound 1 referred to herein as Form C.

In certain embodiments, the present invention provides Form C of Compound 1. According to another embodiment, Form C of Compound 1 is characterized in that it has one or more peaks in its powder X-ray diffraction pattern selected from those at about 6.6°, about 6.8°, about 9.5°, about 9.8°, about 10.3°, about 10.7°, about 13.4°, about 16.3°, about 18.2°, about 19.5°, about 19.9°, about 22.0°, about 23.0°, about 23.4°, about 24.9°, about 25.8°, about 26.5°, about 27.4°, and about 29.5° 2-theta. In some embodiments, Form C of Compound 1 is characterized in that it has two or more peaks in its powder X-ray diffraction pattern selected from those at about 6.6°, about 6.8°, about 9.5°, about 9.8°, about 10.3°, about 10.7°, about 13.4°, about 16.3°, about 18.2°, about 19.5°, about 19.9°, about 22.0°, about 23.0°, about 23.4°, about 24.9°, about 25.8°, about 26.5°, about 27.4°, and about 29.5° 2-theta. In certain embodiments, Form C of Compound 1 is characterized in that it has three or more peaks in its powder X-ray diffraction pattern selected from those at about 6.6°, about 6.8°, about 9.5°, about 9.8°, about 10.3°, about 10.7°, about 13.4°, about 16.3°, about 18.2°, about 19.5°, about 19.9°, about 22.0°, about 23.0°, about 23.4°, about 24.9°, about 25.8°, about 26.5°, about 27.4°, and about 29.5° 2-theta. In particular embodiments, Form C of Compound 1 is characterized in having substantially all of the peaks in its X-ray powder diffraction pattern selected from those at about 6.6°, about 6.8°, about 9.5°, about 9.8°, about 10.3°, about 10.7°, about 13.4°, about 16.3°, about 18.2°, about 19.5°, about 19.9°, about 22.0°, about 23.0°, about 23.4°, about 24.9°, about 25.8°, about 26.5°, about 27.4°, and about 29.5° 2-theta.

According to one aspect, Form C of Compound 1 has a powder X-ray diffraction pattern substantially similar to that depicted in FIG. 1.

In certain embodiments, Form C of Compound 1 is characterized in that it has one or more peaks in its FT-IR spectrum at about 3269.3, about 3124.6, about 2920.9, about 2875.5, about 1566.9, about 1450.3, about 1398.6, about 1352.4, about 1316.3, about 1216.2, about 1129.3, about 1088.8, about 1024.9, about 944.0, about 906.0, about 821.3, about 790.6, and about 728.3 cm$^{-1}$.

In certain embodiments, Form C of Compound 1 is characterized in that it has one or more peaks in its DSC diffractogram at about 122.06° C. In certain embodiments, the peak has an onset of about 104.7° C., endset of about 126.6° C., and ƒnormalised–105.9 Jg$^{-1}$. According to one aspect, Form C of Compound 1 has a DSC diffractogram pattern substantially similar to that depicted in FIG. 2.

In certain embodiments, Form C of Compound 1 is characterized in that it has a water content (KF) of 5.7% w/w.

In some embodiments, the present invention provides a polymorphic form of Compound 1 referred to herein as Form D.

In certain embodiments, the present invention provides Form D of Compound 1. According to another embodiment, Form D of Compound 1 is characterized in that it has one or more peaks in its powder X-ray diffraction pattern selected from those at at about 6.8°, about 9.4°, about 11.5°, about 13.6°, about 15.3°, about 17.0°, about 19.3°, about 20.2°, about 21.5°, about 22.3°, about 23.0°, about 25.2°, and about 29.4° 2-theta. In some embodiments, Form D of Compound 1 is characterized in that it has two or more peaks in its powder X-ray diffraction pattern selected from those at at about 6.8°, about 9.4°, about 11.5°, about 13.6°, about 15.3°, about 17.0°, about 19.3°, about 20.2°, about 21.5°, about 22.3°, about 23.0°, about 25.2°, and about 29.4° 2-theta. In certain embodiments, Form D of Compound 1 is characterized in that it has three or more peaks in its powder X-ray diffraction pattern selected from those at at about 6.8°, about 9.4°, about 11.5°, about 13.6°, about 15.3°, about 17.0°, about 19.3°, about 20.2°, about 21.5°, about 22.3°, about 23.0°, about 25.2°, and about 29.4° 2-theta. In particular embodiments, Form D of Compound 1 is characterized in having substantially all of the peaks in its X-ray powder diffraction pattern selected from those at at about 6.8°, about 9.4°, about 11.5°, about 13.6°, about 15.3°, about 17.0°, about 19.3°, about 20.2°, about 21.5°, about 22.3°, about 23.0°, about 25.2°, and about 29.4° 2-theta.

According to one aspect, Form D of Compound 1 has a powder X-ray diffraction pattern substantially similar to that depicted in FIG. 1.

In certain embodiments, Form D of Compound 1 is characterized in that it has one or more peaks in its FT-IR spectrum at about 2922.4, about 2903.6, about 2865.6, about 1594.1, about 1486.6, about 1450.5, about 1397.8, about 1354.1, about 1322.6, about 1245.9, about 1209.7, about 1130.3, about 1088.0, about 1022.0, about 906.5, about 827.3, about 790.7, and about 736.2 cm$^{-1}$.

In certain embodiments, Form D of Compound 1 is characterized in that it has one or more peaks in its DSC diffractogram at about 166.05° C. In certain embodiments, the peak has an onset of about 151.1° C., endset of about 177.3° C., and ƒnormalised–35.7 Jg$^{-1}$. According to one aspect, Form D of Compound 1 has a DSC diffractogram pattern substantially similar to that depicted in FIG. 2.

In certain embodiments, Form D of Compound 1 is characterized in that it has a water content (KF) of 2.5% w/w.

In certain embodiments, Form A is substantially free of Forms B, C, D, and the amorphous form. In certain embodiments, Form B is substantially free of Forms A, C, D, and the amorphous form. In certain embodiments, Form C is substantially free of Forms A, B, D, and the amorphous form. In certain embodiments, Form D is substantially free of Forms A, B, C, and the amorphous form.

In certain embodiments, Form A is has a melting point of 109° C.

In certain embodiments, Form A is converted to Form D, by heating at 60° C. under vacuum for 24 hours. Re-analysis of material dried for 48 h at 40° C. under vacuum showed a few small additional peaks which, by comparison with the diffractogram from pure Form D, shows that drying at 40° C. under vacuum for 48 h causes a partial transformation of Form A to Form D with a concomitant decrease in the water content from 7.25% w/w to 2.54% w/w.

Form D reverts to Form A when exposed to ≥43% relative humidity. This was the case both for Form A containing a small amount of Form D and for material exclusively of Form D (see FIGS. 6-9).

According to another embodiment, the present invention provides compound 1 as an amorphous solid. Amorphous solids are typically prepared by such methods as lyophilization, melting, and precipitation from supercritical fluid, among others, and such procedures are well known to one of ordinary skill in the art.

General Methods of Providing Compound 1:

Compound 1 was prepared according to the methods described below and as shown in Scheme 1.

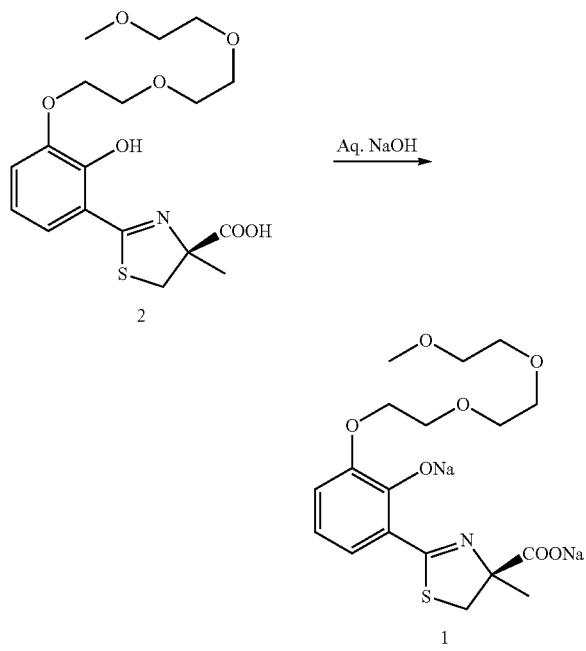

Solid form A of Compound 1 was prepared by dissolving compound 2 in various suitable solvents and salt-forming reagents, which resulted in the formation of Compound 1. In certain embodiments, Compound 1 was isolated in the solid phase. In certain embodiments, Compound 1 was recrystallized to form the solid phase. Specific combinations of solvents, sodium reagents, and conditions under which Compound 1 became a solid phase are discussed in greater detail in the Examples.

Suitable salt-forming reagents include NaOH, KOH, LiOH, MgOH$_2$, CaOH$_2$, NaCl, KCl LiCl, MgCl$_2$, CaCl$_2$, and aqueous solutions thereof. Other bases include pyridine, alkyl amine, dialklyl amine, trialkyl amine, imidazole, benzimidazole, or alkyl lithium.

A suitable solvent may solubilize Compound 2, either partially or completely. Examples of suitable solvents useful in the present invention are a protic solvent, a polar aprotic solvent, or mixtures thereof. In certain embodiments, suitable solvents include an ether, an ester, an alcohol, a ketone, or a mixture thereof. In certain embodiments, the solvent is acetone, tetrahydrofuran, dimethylsulfoxide, dimethylformamide, acetonitrile, or an alcoholic solvent such as methanol, ethanol, propanol, isopropyl alcohol, butanol, isoamyl alcohol. In certain embodiments, the suitable solvent is methanol, ethanol, isopropanol, or acetone wherein said solvent is anhydrous or in combination with water, methyl tert-butyl ether (MTBE) or heptane. In other embodiments, suitable solvents include tetrahydrofuran, 1,4-dioxane, dimethylformamide, dimethylsulfoxide, glyme, diglyme, methyl ethyl ketone, N-methyl-2-pyrrolidone, methyl t-butyl ether, t-butanol, n-butanol, and acetonitrile. In another embodiment, the suitable solvent is anhydrous ethanol. In some embodiments, the suitable solvent is MTBE. In certain embodiments, the solvent is a combination of any two or more solvents.

According to another embodiment, the present invention provides a method for preparing a solid form of Compound 1, comprising the steps of dissolving Compound 2 with a suitable solvent and sodium reagent, and optionally heating to form a solution thereof; and isolating Compound 1.

In certain embodiments Compound 2 is dissolved at about 30 to about 90° C. In certain embodiments Compound 2 is dissolved at about 30 to about 60° C. In certain embodiments Compound 2 is dissolved at about 40 to about 70° C. In certain embodiments Compound 2 is dissolved at about 50 to about 80° C. In certain embodiments Compound 2 is dissolved at about 60 to about 90° C. In certain embodiments Compound 2 is dissolved at about 50 to about 60° C. In other embodiments, Compound 2 is dissolved at about 50 to about 55° C. In still other embodiments, Compound 2 is dissolved at the boiling temperature of the solvent. In other embodiments, Compound 2 is dissolved without heating (e.g., at ambient temperature, approximately 20-25° C.).

In certain embodiments, Compound 1 precipitates from the mixture. In another embodiment, Compound 1 crystallizes from the mixture. In other embodiments, Compound 1 crystallizes from solution following seeding of the solution (i.e., adding crystals of Compound 1 to the solution).

Crystalline Compound 1 can precipitate out of the reaction mixture, or be generated by removal of part or all of the solvent through methods such as evaporation, distillation, filtration (e.g., nanofiltration, ultrafiltration), reverse osmosis, absorption and reaction, by adding an anti-solvent (e.g., water, MTBE and/or heptane), by cooling (e.g., crash cooling) or by different combinations of these methods.

As described generally above, Compound 1 is optionally isolated. It will be appreciated that Compound 1 may be isolated by any suitable physical means known to one of ordinary skill in the art. In certain embodiments, precipitated solid Compound 1 is separated from the supernatant by filtration. In other embodiments, precipitated solid Compound 1 is separated from the supernatant by decanting the supernatant.

In certain embodiments, precipitated solid Compound 1 is separated from the supernatant by filtration.

In certain embodiments, isolated Compound 1 is dried in air. In other embodiments isolated Compound 1 is dried under reduced pressure, optionally at elevated temperature.

DEFINITIONS

As used herein, when ranges of values are disclosed, and the notation "from n$_1$ . . . to n$_2$" is used, where n$_1$ and n$_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units.

The term "alkyl," as used herein, alone or in combination, refers to a straight-chain or branched-chain alkyl group containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl groups include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene ($-CH_2-$). Unless otherwise specified, the term "alkyl" may include "alkylene" groups.

The term "alkoxy," as used herein, alone or in combination, refers to an alkyl ether group, wherein the term alkyl is as defined below. Examples of suitable alkyl ether groups include methoxy, ethoxy, n-propoxy, isopropoxy, n-butoxy, iso-butoxy, sec-butoxy, tert-butoxy, and the like.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The terms "benzo" and "benz," as used herein, alone or in combination, refer to the divalent group $C_6H_4=$ derived from benzene. Examples include benzothiophene and benzimidazole.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl group having the meaning as defined above wherein one or more hydrogens are replaced with a halogen. Specifically embraced are monohaloalkyl, dihaloalkyl and polyhaloalkyl groups. A monohaloalkyl group, for one example, may have an iodo, bromo, chloro or fluoro atom within the group. Dihalo and polyhaloalkyl groups may have two or more of the same halo atoms or a combination of different halo groups. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene ($-CFH-$), difluoromethylene ($-CF_2-$), chloromethylene ($-CHCl-$) and the like.

The term "hydroxy," as used herein, alone or in combination, refers to $-OH$.

The term "lower," as used herein, alone or in a combination, where not otherwise specifically defined, means containing from 1 to and including 6 carbon atoms.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridine, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., $-CH_2CH_3$), fully substituted (e.g., $-CF_2CF_3$), monosubstituted (e.g., $-CH_2CH_2F$) or substituted at a level anywhere in-between fully substituted and monosubstituted (e.g., $-CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as $-C(O)N(R)-$ may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The compounds disclosed herein can exist as therapeutically acceptable salts. Such salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid.

In addition to specific exemplary salts described above, representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, zinc, and calcium salts of the compounds disclosed herein, and the like.

Basic addition salts can be prepared during the final isolation and purification of the compounds, often by reacting a carboxy group with a suitable base such as the hydroxide, carbonate, or bicarbonate of a metal cation or with ammonia or an organic primary, secondary, or tertiary amine. The cations of therapeutically acceptable salts include, without limitation, lithium, sodium (e.g., NaOH), potassium (e.g., KOH), calcium (including $Ca(OH)_2$), magnesium (including $Mg(OH)_2$ and magnesium acetate), zinc, (including $Zn(OH)_2$ and zinc acetate) and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, piperazine, choline hydroxide, hydroxyethyl morpholine, hydroxyethyl pyrrolidone, imidazole, n-methyl-d-glucamine, N, N'-dibenzylethylenediamine, N, N'-diethylethanolamine, N, N'-dimethylethanolamine, triethanolamine, and tromethamine. Basic amino acids such as 1-glycine and 1-arginine, and amino acids which may be zwitterionic at neutral pH, such as betaine (N,N,N-trimethylglycine) are also contemplated. See, for example, Berge et al. (1977) "Pharmaceutical Salts", *J. Pharm. Sci.* 66:1-19; incorporated herein by reference.

In certain embodiments, the salts may include lysine, N-methyl glutarate (NMG), tromethamine, calcium, magnesium, potassium, di-potassium, sodium, di-sodium, zinc, and piperazine salts of compounds disclosed herein. In some embodiments, the salts include one or more metal cations and, as required by charge, an anion such as halide, carbonate, bicarbonate, hydroxide, carboxylate, sulfate, bisulfate, phosphate, nitrate, alkoxy having from 1 to 6 carbon atoms, sulfonate, and aryl sulfonate.

Salts disclosed herein may combine in 1:1 molar ratios, and in fact this is often how they are initially synthesized. However, it will be recognized by one of skill in the art that the stoichiometry of one ion in a salt to the other may be otherwise. Salts shown herein may be, for the sake of convenience in notation, shown in a 1:1 ratio; all possible stoichiometric arrangements are encompassed by the scope of the present invention.

The terms, "polymorphs" and "polymorphic forms" and related terms herein refer to crystal forms of the same molecule, and different polymorphs may have different physical properties such as, for example, melting temperatures, heats of fusion, solubilities, dissolution rates and/or vibrational spectra as a result of the arrangement or conformation of the molecules in the crystal lattice. Polymorphs of a molecule can be obtained by a number of methods, as known in the art. Such methods include, but are not limited to, melt recrystallization, melt cooling, solvent recrystallization, desolvation, rapid evaporation, rapid cooling, slow cooling, vapor diffusion and sublimation.

Techniques for characterizing polymorphs include, but are not limited to, differential scanning calorimetry (DSC), X-ray powder diffractometry (XRPD), thermal gravimetric analysis (TGA), dynamic vapor sorption/desorption (DVS), single crystal X-ray diffractometry, vibrational spectroscopy, e.g. IR and Raman spectroscopy, solid state NMR, hot stage optical microscopy, scanning electron microscopy (SEM), electron crystallography and quantitative analysis, particle size analysis (PSA), surface area analysis, solubility studies and dissolution studies.

Certain compounds, salts, and polymorphs from which pharmaceutical compositions as disclosed herein may be formed can be synthesized as described in US 20100137383 and Bergeron, R J et al., "Design, Synthesis, and Testing of Non-Nephrotoxic Desazadesferrithiocin Polyether Analogues," *J Med Chem.* 2008, 51(13), 3913-23, which are hereby incorporated by reference in their entireties. Additional synthetic protocols for compounds disclosed herein may be found in US20080214630A1 published Sep. 4, 2008; US20100093812A1, published Apr. 15, 2010, and WO2011017054A2, published Feb. 10, 2011.

As used herein, the term "amorphous form" refers to a noncrystalline form of a substance.

As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a hamster, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). When referring to XRPD data, "about" refers to +/−0.5°, +/−0.4°, +/−0.3°, +/−0.2°, or +/−0.1°.

As used herein, the term "bioavailability" generally refers to the percentage of the administered dose that reaches the blood stream of a subject.

As used herein, the terms "carrier" and "diluent" refers to a pharmaceutically acceptable (e.g., safe and non-toxic for administration to a human) carrier or diluting substance useful for the preparation of a pharmaceutical formulation. Exemplary diluents include sterile water, bacteriostatic water for injection (BWFI), a pH buffered solution (e.g. phosphate-buffered saline), sterile saline solution, Ringer's solution or dextrose solution.

As used herein, the term "chelation" means to coordinate (as in a metal ion) with and inactivate. Chelation also includes decorporation, a term which itself encompasses chelation and excretion.

As used herein, the term "compound" is meant to be interchangeable with the term "active compound" or "drug," and refers to a compound having beneficial prophylactic and/or therapeutic properties when administered to a patient and/or activity against a biological target which is associated with a disease.

When the term "counterion" or the phrase "X is a counterion" is used in any formulae herein, and neither the compound nor the counterion is drawn showing explicit ionic character, such ionic character may be inferred and a corresponding charges on each moiety be assumed to be present or absent. For example, if X is a monovalent cation such as $Na^+$, it may be inferred that the coupled compound has lost a proton to form an ionic bond with X, despite the formulae being drawn to explicitly show all protons in place. Similarly, when X is an anion, the coupled compound takes on cationic character. As used herein, the term counterion encompasses all possible placement where on a compound a counterion has bound and ratios of charges. Additionally, counterions and compounds may combine in uneven molar ratios to form solid salts. As those of skill in the art will recognize, different ratios of counterions may form stable arrangements and solid forms, including 1:1, 2:1, and 3:1 based on preferred oxidation states of each ion, salt formation conditions (including solvent), etc. All such forms are contemplated here.

The term, "desolvated solvate," as used herein, refers to a crystal form of a substance which can only be made by removing the solvent from a solvate.

As used herein, the terms "dosage form" and "unit dosage form" refer to a physically discrete unit of a therapeutic agent for the patient to be treated. Each unit contains a predetermined quantity of active material calculated to produce the desired therapeutic effect. It will be understood, however, that the total dosage of the composition will be decided by the attending physician within the scope of sound medical judgment. The "dosage strength" refers to the total drug content of the dosage form.

As used herein, the term "excipient" refers to any inert substance added to a drug and/or formulation for the purposes of improving its physical qualities (i.e. consistency), pharmacokinetic properties (i.e. bioavailability), pharmacodynamic properties and combinations thereof.

As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of disease as the individual being treated, who is about the same age as the individual being treated (to ensure that the stages of the disease in the treated individual and the control individual(s) are comparable).

As used herein, the term "in vitro" refers to events that occur in an artificial environment, e.g., in a test tube or reaction vessel, in cell culture, etc., rather than within a multi-cellular organism.

As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

As used herein, the term "pharmaceutically-acceptable" refers to any entity or composition that does not produce an undesirable allergic or antigenic response when administered to a subject.

As used herein, the term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

As used herein, "solid" when referring to a salt form means relatively solid, at room temperature, and/or containing a substantial amount of solids. A solid may be amorphous in form and/or be a solvated solid with some quantity of residual or coordinated of solvent molecules. A crystalline salt is an example of a solid. By way of example, a wax could be considered a solid, whereas an oil would not be. A "solid composition" as used herein includes a salt of a compound, or a polymorph or amorphous solid form thereof.

As used herein, the term "solvate" refers to a crystal form of a substance which contains solvent. The term "hydrate" refers to a solvate wherein the solvent is water.

As used herein, the term "stable" refers to the ability of the therapeutic agent to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 3, 6, 12, 18, 24, 30, 36 months or more). In certain embodiments, pharmaceutical compositions described herein have been formulated such that they are capable of stabilizing, or alternatively slowing or preventing the degradation, of one or more therapeutic agents formulated therewith.

As used herein, the term "subject" refers to a human or any non-human animal (e.g., mouse, rat, rabbit, dog, cat, cattle, swine, sheep, horse or primate). A human includes pre and post natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Uses of Compounds

Inventive polymorphs described herein may be used to effectively treat metal overload. As used herein, the term "metal overload" refers to a condition in which the body has reached its limit to absorb and excrete a particular metal, resulting in an excess amount of the metal accumulated in various tissues inside the body that lead to toxicity or other pathological conditions. Inventive polymorphs described herein may be used to chelate, sequester, reduce, or eliminate such accumulated metals including, but not limited to, iron, heavy metals (e.g., $Hg^{2+}$), uranium, and other radioactive isotopes such as lanthanide and actinide series. As used herein, the term "treat," "treatment," or "treating" refers to any method used to reduce metal levels (e.g., iron levels) as compared to a baseline control level and/or partially or completely alleviate, ameliorate, relieve, inhibit, prevent, delay onset of, reduce severity of and/or reduce incidence of one or more symptoms or features of a disease, disorder, and/or condition associated with metal overload.

In some embodiments, the metal overload that can be treated using a method of the invention is uranium overload caused by, for example, radiation poisoning.

In some embodiments, the metal overload that can be treated using a method of the invention is iron overload. In various embodiments, a method of the invention can be used to treat iron overload due to repeated blood transfusion (i.e., transfusional iron overload) or increased iron absorption.

In some embodiments, the present invention is used to treat iron overload. As used herein, the term "iron overload" refers to a condition in which an excess amount of iron accumulate inside a body that leads to toxic or other pathological conditions. Without wishing to be bound by theory, iron overload can be toxic in part through the generation by iron of reactive oxygen species such as $H_2O_2$. In the presence of $Fe^{2+}$, $H_2O_2$ is reduced to the hydroxyl radical (HO), a highly reactive species, a process known as the Fenton reaction. The hydroxyl radical reacts very quickly with a variety of cellular constituents and can initiate free radicals and radical-mediated chain processes that damage DNA and membranes, as well as produce carcinogens.

In various embodiments, a use of the invention can be used to treat a subject suffering from anaemia that results in increased accumulation of iron in the body either due to need for repeated blood transfusions or increased iron absorption. Exemplary causes of anaemia include, but are not limited to, Beta thalassemia major or intermedia, and other anemias including but not limited to non-transfusion dependent Thalassaemia (NTDT—i.e. patients with clinically milder forms of thalassemia, such as β-thalassemia intermedia, α-thalassemia (HbH disease), and HbE/β-thalassemia, who require occasional or no blood transfusions), Blackfan-Diamond anemia, Fanconi's anemia and other inherited bone marrow failure syndromes, Sideroblastic anemia, congenital dyserythropoietic anemias, sickle cell disease, pyruvate kinase deficiency (and other red cell enzyme deficiency causing hemolytic anemia), aplastic anemia, refractory anemias, red cell aplasia, Myelodysplasia (MDS), chronic myelofibrosis, paroxysmal nocturnal hemoglobinuria); from increased absorption of dietary iron (in conditions such as hereditary hemochromatosis and porphyria cutanea tarda); from maldistribution or redistribution of iron in the body (e.g., resulted from conditions such as atransferrinemia, aceruloplasminemia, and Friedreich's ataxia); from transfusional iron overload from off-therapy leukemias, before and after bone marrow transplant and myelodysplastic syndrome; from diabetes or obesity; and/or from liver diseases (e.g., hepatitis).

In some embodiments, a use of the invention can be used to treat a subject suffering from β-thalassemia-intermedia. In some embodiments, a use of the invention can be used to treat a subject suffering from β-thalassemia-major.

In some embodiments, a use of the invention can be used to treat a subject suffering from iron overload due to repeated blood transfusions as a consequence of the subject suffering from sickle cell disease. In some embodiments, a use of the invention can be used to treat a subject suffering from Myelodysplastic Syndrome (MDS).

Typically, under normal conditions, iron absorption and loss are balanced at about 1 mg/day. Iron overload can be caused by repeated blood transfusion (i.e., transfusional iron overload) or increased iron absorption required in patients suffering from various congenital and acquired anemias. Exemplary causes of anaemia include, but are not limited to, β-thalassemia-major, non-transfusion dependent Thalassaemia (NTDT) such as β-thalassemia-intermedia, Blackfan-Diamond anemia, Sideroblastic anemia, sickle cell disease, aplastic anemia, red cell aplasia, Myelodysplasia (MDS), chronic myelofibrosis, paroxysmal nocturnal hemoglobinuria.

Without effective treatment, iron overload may cause iron levels progressively increases with deposition in various tissues including, but not limited to, the liver, heart, pancreas, and other endocrine organs. Iron accumulation may also produce (i) liver disease that may progress to cirrhosis and hepatocellular carcinoma, (ii) diabetes related both to iron-induced decreases in pancreatic β-cell secretion and increases in hepatic insulin resistance and (iii) heart disease.

Polymorphs according to the present invention may be used to treat various iron overload conditions including, but not limited to, iron overload resulted from red blood cells chronic transfusion (necessary in conditions such as beta thalassemia major or intermedia, and other anemias including but not limited to non-transfusion dependent Thalassaemia (NTDT—i.e. patients with clinically milder forms of thalassemia, such as β-thalassemia intermedia, α-thalassemia (HbH disease), and HbE/β-thalassemia, who require occasional or no blood transfusions), Blackfan-Diamond anemia, Fanconi's anemia and other inherited bone marrow failure syndromes, Sideroblastic anemia, congenital dyserythropoietic anemias, sickle cell disease, pyruvate kinase deficiency (and other red cell enzyme deficiency causing hemolytic anemia), aplastic anemia, refractory anemias, red cell aplasia, Myelodysplasia (MDS), chronic myelofibrosis, paroxysmal nocturnal hemoglobinuria); from increased absorption of dietary iron (in conditions such as hereditary hemochromatosis and porphyria cutanea tarda); from maldistribution or redistribution of iron in the body (e.g., resulted from conditions such as atransferrinemia, aceruloplasminemia, and Fredreich's ataxia); from transfusional iron overload from off-therapy leukemias, before and after bone marrow transplant and myelodysplastic syndrome; from diabetes or obesity; and/or from liver diseases (e.g., hepatitis).

In various embodiments, polymorphs of the present invention may be used to treat acute iron toxicity from ingestion or infusion of iron; to reduce total body iron secondary to transfusion or excess iron dietary absorption; and/or for maintenance of iron balance after total body iron has been satisfactorily reduced and only excess daily transfusional or dietary iron needs to be excreted. Thus, in some embodiments, administration of a polymorph described herein results in excretion between 0.2 and 0.5 mg Fe/kg body weight of the patient per day (e.g., about 0.2, 0.3, 0.4, or 0.5 mg Fe/kg body weight of the patient per day). In some embodiments, this amount of excretion is recommended for chronic iron overload secondary to transfusion. In some embodiments, administration of a polymorph described herein results in excretion between 0.25-0.5 mg Fe/kg/d of patient body weight (e.g., about 0.25, 0.30, 0.35, 0.40, 0.45, 0.50 mg Fe/kg body weight of the patient per day). In some embodiments, this amount of excretion is recommended to achieve iron balance neutrality and/or for maintenance treatment.

In some embodiments, the efficacy of treatment according to the present invention may be measured by iron-clearing efficiency. As used herein, the term "iron-clearing efficiency (ICE)" refers to the molar efficiency or efficaciousness of a given dose or concentration of chelator in clearing iron from the body or one of its tissues, organs or parts. Efficaciousness in turn concerns quantity of iron removed from a target system (which may be a whole body, an organ, a tissue or other) in a unit of time. Iron clearing efficiency (ICE) is calculated by subtracting total iron excretion before treatment from total iron excreted after treatment and dividing that value by the theoretical amount of iron that could have been bound by the dose of chelator administered times 100.

In some embodiments, measurement of certain markers will be used as a proxy to assess therapeutic efficacy. In iron overload diseases, for example, the free iron species, non-transferrin-bound iron (NTBI), and labile plasma iron (LPI, also called redox-active iron) in the circulation, and the labile and chelatable iron pool within the cells, are responsible for iron toxicity through the generation of reactive oxygen species. The characteristic features of advanced iron overload are dysfunction and failure of vital organs such as liver and heart in addition to endocrine dysfunctions. For the estimation of body iron, there are direct and indirect methods available. See, e.g, Kohgo Y "Body iron metabolism and pathophysiology of iron overload," *Int J Hematol.*, 2008 88(1): 7-15 (epub 2008 Jul. 2); Angelucci E et al. "Hepatic Iron Concentration and Total Body Iron Stores in Thalassemia Major," *NEJM,* 2000 343(5): 327-331.

In some embodiments, measurement of serum ferritin can be used for monitoring efficacy. Ferritin is a globular cytoplasmic protein consisting of 25 heterodimeric subunits of H and L that stores iron as ferric hydroxide phosphate in a controlled manner, which may be found in the plasma in low concentration. By quantitative phlebotomy, it has been demonstrated that serum ferritin (SF) correlates with total body iron stores. However, the level of SF may be affected by acute and chronic inflammation and infections. There is also a difference between the standard values of SF concentration in males and females (normal range 10-220 µg/L in males; 10-85 µg/L in females). Therefore, data should be interpreted carefully when using SF as a biological marker for evaluation of body iron stores. Clinically, in order to detect organ dysfunctions, serum ferritin determinations should be conducted once every 1-3 months. According to the guidelines of the International MDS Symposium, 1,000 µg/L represents the threshold of the target SF value at which iron chelation therapy should be initiated in patients with transfusion iron overload. When serum ferritin levels exceed 1,500 μg/L, patients should be examined for the symptoms of cardiac failure or arrhythmias, and periodical cardiac echograms may also be useful in diagnosis. The concentration of heart iron is increased when SF levels become greater than 1,800 μg/L, and the prevalence of cardiac events is significantly increased when SF levels are more than 2,500 μg/L.

The present disclosure recognizes that even serum ferritin levels greater than 500 μg/L can be cause for iron chelation therapy. Thus, in some embodiments, the present invention may be used to treat a subject that has a serum ferritin level greater than about 500 μg/L (e.g., greater than about 600 μg/L, 700 μg/L, 800 μg/L, 900 μg/L). In some embodiments, the present invention may be used to treat a subject that has a serum ferritin level greater than about 800 μg/L. In some embodiments, the present invention may be used to treat a subject that has a serum ferritin level greater than about 1,000 μg/L (e.g., greater than about 1,200 μg/L, 1,500 μg/L, 1,800 μg/L, 2,000 μg/L, 2,200 μg/L, or 2,500 μg/L). In various embodiments, administration of a polymorph according to the present invention results in reduction of serum ferritin level in the subject as compared to a baseline control. In some embodiments, administration of a polymorph according to the present invention results in the serum ferritin level in the subject being treated below 1,000 μg/L.

An alternate method of assessing iron level in the body is via the measurement of labile plasma iron, a redox active form of non-transferrin bound iron that is chelatable, making it potentially available for transport into extrahepatic tissues. LPI can be accurately and reproducibly assayed by fluorescent method; see, e.g., Esposito B P et al., "Labile plasma iron in iron overload: redox activity and susceptibility to chelation," *Blood,* 2003, 102(7):2670-7 (Epub 2003 Jun. 12) and Wood, J C et al., "Relationship between labile plasma iron, liver iron concentration and cardiac response in a deferasirox monotherapy trial," *Haematologica,* 2011 96(7): 1055-1058 (epub 2011 Mar. 10). LPI measurements may be influenced by antioxidant and iron-binding activities of sera. Since LPI measurements are performed on intact serum or plasma, they should represent the sum of the pro-oxidant potential of the chelatable iron and the antioxidant activity of the sample. The total antioxidant activity of human plasma/serum has been estimated in the range of 1 mM and can be influenced by a variety of factors including diet and clinical conditions. Therefore, it is possible that sera containing similar concentrations of NTBI might have different levels of LPI, due to masking by antioxidants. It has also been suggested that chronic control of circulating LPI may be an important goal for iron chelation therapy in order to prevent oxidative damage, and to lower the risk of extrahepatic organ dysfunction.

Alternatively, iron concentration in a target organ or tissue may be measured directly. The measurement of liver iron concentration (LIC) by liver biopsy has traditionally been viewed as the most reliable means to assess body iron storage. The LIC level may also be determined by magnetic resonance imaging (MRI). The liver is the most important organ for iron storage with the largest capacity to sequester excess iron. In patients with β-thalassemia, the risk of organ dysfunction is increased when LIC values are greater than 7 mg/g (liver, dry weight), and LIC levels of over 15 mg/g (liver, dry weight) increase the risk of early cardiac death due to iron deposition in the myocardium. Studies in the deferasirox clinical development program in β-thalassemia also demonstrated a correlation between the reduction in LIC and SF values (R=0.63). In some embodiments, the present invention may be used to treat a subject that has an LIC level greater than about 7 mg/g (liver, dry weight) (e.g., greater than about 8, 9, 10, 11, 12, 13, 14, or 15 mg/g (liver, dry weight)). In some embodiments, administration of a polymorph according to the present invention results in reduction of the LIC level in the subject as compared to a baseline control. In some embodiments, administration of a polymorph according to the present invention results in the LIC level in the subject being treated below 7 mg/g (liver, dry weight).

The determination of cardiac iron concentration is clinically important because one of the major causes of death in iron overload is sudden cardiac arrest. Additionally, pancreatic beta cells are another important target of iron toxicity, which cause glucose intolerance and diabetes mellitus.

Recently, physical detection methods using magnetic resonance imaging (MRI) and superconducting quantum interference devices (SQUID) have become available to indirectly estimate iron concentration in liver, pancreas, and myocardium. In some embodiments, the cardiac iron level may be measured by MRI R2* or T2* MRI. It has been reported that a shortening of myocardial T2* to less than 20 ms (implying increased myocardial iron above normal) is associated with an increased likelihood of decreased left ventricular ejection fraction (LVEF), whereas patients with T2* values greater than 20 ms have a very low likelihood of decreased LVEF. In some embodiments, the present invention may be used to treat a subject that has a myocardial T2* value less than about 20 ms (e.g., less than about 18, 16, 14, 10, 8, 6, 4, 2 ms). In some embodiments, administration of a polymorph according to the present invention results in the reduction of cardiac iron level in the subject as compared to a baseline control. In some embodiments, the administration of a polymorph according to the present invention results in myocardial T2* value great than 20 ms.

Appropriate baseline controls described herein (e.g., for serum ferritin, LIC, and/or cardiac iron level) are indicative of the pre-treatment levels in the corresponding tissues.

The subject (also referred to as "patient" or "individual") being treated can be a child, adolescent, or adult human. Besides being useful for human treatment, certain compounds and polymorphs disclosed herein may also be useful for veterinary treatment of companion animals, exotic animals and farm animals, including mammals, rodents, and the like. More preferred animals include horses, dogs, and cats.

Combination Therapy

In some embodiments, polymorphs provided herein for treating diseases, disorders or conditions relating to metal toxicity or overload in a human or animal subject in need of such treatment can be used in combination with one or more additional agents that are beneficial for the treatment of such diseases, disorders or conditions and/or can reduce side effects.

In certain instances, it may be appropriate to administer a polymorph described herein in combination with supplements of essential trace minerals required by the body for proper functioning, for example zinc and magnesium, to replace those which will inadvertently be lost to chelation therapy. Or, by way of example only, the therapeutic effectiveness of a polymorph described herein may be enhanced by co-administration of an adjuvant (i.e., by itself the adjuvant may only have minimal therapeutic benefit, but in combination with another therapeutic agent, the overall therapeutic benefit to the patient is enhanced). Or, by way of example only, the benefit of a polymorph described herein may be enhanced with another therapeutic agent (which also includes a therapeutic regimen) that also has therapeutic benefit for treating metal overload. By way of example only, in a treatment for thalassemia involving administration of a polymorph described herein, increased therapeutic benefit may result by also providing the patient with another therapeutic agent for thalassemia, for example deferoxamine. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of certain polymorphs as disclosed herein with: deferasirox, deferiprone, deferoxamine, DTPA (diethylene triamine pentaacetic acid), EGTA (ethylene glycol tetraacetic acid), EDTA (ethylenediamine tetraacetic acid), DMSA (dimercaptosuccinic acid), DMPS (dimercapto-propane sulfonate), BAL (dimercaprol), BAPTA (aminophenoxyethane-tetraacetic acid), D-penicillamine, and alpha lipoic acid.

In various embodiments, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to weeks.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

General Procedures

A. Materials

Compound 2 (free acid) was made according to known methods and was used to prepare Form A of Compound 1. Form A of Compound 1 was used to prepare Form B of Compound 1, Form C of Compound 1, Form D of Compound 1, and the amorphous form. Solvents and other reagents were purchased from commercial suppliers and were either HPLC or ACS grade and used as received.

B. Experimental Methods

Polymorph Screen

Both thermodynamic and kinetic crystallization techniques were employed. These techniques are described in more detail below. Once solid samples were harvested from crystallization attempts, they were either examined under a microscope for morphology or observed with the naked eye. Any crystalline shape was noted, but sometimes the solid exhibited unknown morphology, due to small particle size. Solid samples were then analyzed by XRPD.

a. Ambient Solution (AS)

Solutions were prepared as close to saturation as possible in various solvents at ambient. This was accomplished by adding an anti-solvent to the solution until turbidity was observed. The sample was left at ambient. Solids that formed were isolated by either filtration or decantation and allowed to dry prior to analysis.

b. Fast Evaporation (FE)

Solutions were prepared in various solvents and sonicated between aliquot additions to assist in dissolution. Once a mixture reached complete dissolution, as judged by visual observation, the solution was filtered through a 0.2-μm nylon or PVDF filter. The filtered solution was allowed to evaporate at ambient. The solids that formed were isolated and analyzed.

c. Slow Cool (SC)

Saturated solutions were prepared in various solvents at elevated temperatures and filtered through a 0.2-μm nylon filter into a vial. Vials were then left on top of the hot plate and allowed to cool to ambient temperature slowly. The resulting solids were isolated by filtration and dried prior to analysis.

d. Slow Evaporation (SE)

Solutions were prepared in various solvents. The solution was then filtered through a 0.2-μm nylon or PVDF filter. The filtered solution was allowed to evaporate at ambient in a vial covered with aluminum foil perforated with pinholes. The solids that formed were isolated and analyzed.

e. Slurry Experiments

Solutions were prepared by adding enough solids to a given solvent so that excess solids were present. The mixture was then agitated in a sealed vial on a slurry wheel at ambient temperature. Solids were isolated by vacuum filtration.

Instrumental Techniques

1. HPLC Analysis (MET/CR/0171)

An Agilent HP1100 instrument equipped with diode array was used to acquire data Column: Luna C18, 150×4.6 mm, 5 μm Injection volume: 10 microliter Detection: UV @222 nm Mobile Phase A: 49:51 Potassium phosphate buffer, pH 6.5:Methanol Mobile Phase B: Methanol

| Time (mins) | % A | % B |
|---|---|---|
| 0 | 100 | 0 |
| 12 | 100 | 0 |
| 20 | 20 | 80 |
| 25 | 20 | 80 |
| 26 | 100 | 0 |
| 36 | 100 | 0 |

Flow rate: 1.0 milliliter/min

Temperature: 30° C.

Run time: 36 minutes

Integration time: 25 minutes

Wash vial: 50:50 v/v Water:Methanol

2. LC-MS Analysis

The method conditions described below were used routinely for LC-MS analysis under the 2 minute runtime method.

Inlet method: INMS7_METCR1673_IPC
MS Method: 1900 EXPMS7_METCR1673_IPC_CV10
  Column: Waters Atlantis C18, 30×2.1 mm, 3 μm
Inj. volume: 10 μL
Detection: UV @ 215 nm
Mobile phase: Gradient elution
  Mobile Phase A: 0.1% formic acid/water
  Mobile Phase B: 0.1% formic acid/MeCN

| Time (mins) | % A | % B |
|---|---|---|
| 0.0 | 95 | 5 |
| 1.5 | 0 | 100 |
| 1.6 | 0 | 100 |
| 1.61 | 95 | 5 |
| 2.00 | 95 | 5 |

Flow rate: 1.0 mL/min
Temperature: 40° C.
Run time: 2 minutes
Integration time: 1.9 minutes
  Wash vial: Water/acetonitrile (1/1 v/v)
  Ionisation Electrospray +ve ion
  Mass range: 150-1900 Da
The method conditions described below were used routinely for LC-MS analysis under the 6 minute runtime method.
Inlet method: INMS7_METCR1416
MS Method: 6MIN_1900_EXPMS7_METCR1673_IPC_CV10
  Column: Waters Atlantis C18, 30×2.1 mm, 3 μm
Inj. volume: 10 μL
Detection: UV @ 215 nm
Mobile phase: Gradient elution
  Mobile Phase A: 0.1% formic acid/water
  Mobile Phase B: 0.1% formic acid/MeCN

| Time (mins) | % A | % B |
|---|---|---|
| 0.0 | 95 | 5 |
| 5 | 0 | 100 |
| 5.4 | 0 | 100 |
| 5.42 | 95 | 5 |
| 7.00 | 95 | 5 |

Flow rate: 0.6 mL/min
Temperature: 40° C.
Run time: 7 minutes
Integration time: 6 minutes
  Wash vial: Water/acetonitrile (1/1 v/v)
  Ionisation Electrospray +ve ion
  Mass range: 150-1900 Da 3. Differential Scanning Calorimetry (DSC)

A Mettler Toledo DSC 821 instrument was used for the thermal analysis operating with STARe™ software. The analysis was conducted in 40 μL open aluminium pans, under nitrogen and sample sizes ranged from 1-10 mg. Typical analysis method was 20-350 at 10° C./minute.

4. FT-IR Analysis (IR)

FT-IR Spectra were acquired using a PerkinElmer Spectrum One FT-IR spectrometer. Samples were analysed directly using a universal ATR attachment in the frequency range 4000-600 cm-1. Spectrums were processed using Spectrum CFD, vs. 4.0 PerkinElmer Instruments LLC.

5. Polarised Light Microscopy

The instrument used for digital capture was an Olympus BX41 microscope with digital camera attachment. The magnification was ×100 and ×400. Samples were observed under plane polarised and cross polarised light.

6. Thermal Microscopy

The instrument used for digital capture was an Olympus BX41 microscope with digital camera and hot stage attachment. The magnification was ×100 and ×400. Samples were observed under plane polarised and cross polarised light.

7. $^1$H NMR Analysis (NMR)

$^1$H NMR Spectra were acquired using a Bruker 400 MHz spectrometer and data was processed using Topspin. Samples were prepared in DMSO-$d_6$ and calibrated to the solvent residual at 2.50 ppm.

8. Thermogravimetric Analysis (TGA)

A Perkin Elmer Pyris Diamond TG/DTA 6300 was used to measure the weight loss as a function of temperature from 30-600° C. The scan rate was 10° C. per minute and the purge gas was nitrogen.

9. X-Ray Powder Diffraction (XRPD)

X-Ray powder diffraction (XRPD) analysis was carried out using a Bruker D2 Phaser powder diffractometer employing a LynxEye detector. The samples underwent minimum preparation but, if necessary they were milled in a pestle and mortar before acquisition.

The samples were continuously spun during data collection and scanned using a step size of 0.02° two theta (2θ) between the range of 4°-40° two theta and a count time of 10 seconds per step. Data was processed using Bruker Diffrac. Suite.

Example 1

Preparation of Form A of Compound 1

Compound 2 (25.0 g, 1.0 wt.) was charged to the vessel. Ethanol (125.0 mL, 5.0 vol) was added and the mixture stirred under nitrogen until full dissolution was achieved (15 to 20 min). Sodium hydroxide solution (5M, 25.0 mL, 1.0 vol, 2.0 eq.) was added portion-wise over 7 minutes (temperature rose from 18 to 26° C.). The solution darkened in colour during the addition and lightened again to a straw colour at the end of the addition. The reaction mixture was stirred under nitrogen for 1 hour.

TBME was added drop-wise until the mixture just turned cloudy (ca 350 mL, 14 vol) and a few seeds of Compound 1 was charged to the vessel. Ethanol (125.0 mL, 5.0 vol) was added and the mixture were charged. The mixture was stirred at ambient temperature and after 4 minutes a small amount of flocculent solid was present. After stirring for a further 5 minutes the slurry had thickened considerably. The remainder of the TBME (ca 150 mL, 6 vol) was charged and the slurry stirred for a further 30 minutes and a sample taken for XRPD analysis (A0348-134-01).

The solid was stirred overnight at ambient temperature under nitrogen and then collected by filtration under a stream of nitrogen (filter paper, filter dia. 75 mm, filtration time 2 minutes). The flask and filter cake were washed with TBME (125 mL×2, 5 vol×2) and pulled dry on the filter under nitrogen to give a white solid 23.51 g (78.4% th., A0348-134-04), 99.88% (by area at 222 nm), that contained water (7% w/w) and TBME (<0.1% w/w).

Form A of Compound 1 was generated by crystallisation from water/ethanol/TBME (1/5/20, v/v). Scale-up to 5.0 g was carried out twice, and scale-up to 25.0 g was carried out once under the above conditions. Form A was generated each time.

Form A of Compound 1 remained as Form A when exposed to 75% relative humidity (RH) at 15-25° C. for 1-2 days. Form A of Compound 1 remained as Form A when exposed to 43% RH at 50° C. for 5 days.

Example 2

Preparation of Form B of Compound 1

Separate portions of Form A (1.0 g, 1.0 wt.) were charged to each of the three vessels. Ethyl acetate (10 vol), isopropyl acetate (10 vol) and IPA (10 vol) were then added to the vessels and the suspensions were stirred for up to 12 d at 40 to 45° C. The products were isolated by filtration, washed with recycled filtration solvents and dried under a stream of nitrogen. The results are provided below.

| Solvent | Temperature | Target Form* | Time stirred 20 h | Time stirred 4 days | Seeded @ 4 days** | Time stirred (continued) 6 days | Time stirred (continued) 11 days |
|---|---|---|---|---|---|---|---|
| Ethyl acetate | 40-45° C. | B > A | Amorphous | Amorphous | B (0.1% w/w) | B | N/A |
| Isopropyl acetate | 40-45° C. | B + A | Amorphous | Amorphous | B (0.1% w/w) | Amorphous | Amorphous + Form B |
| Isopropanol | 40-45° C. | B | A | A | B (0.1% w/w) | B | N/A |

*Target form based on results obtained from equilibration screens.
**Seeding was performed at a low level (0.1% w/w) to avoid detection in the XRPD of the isolated products.

| Solvent | Isolated yield | Chemical purity (% area @ 222 nm) | Solvent content ($^1$H NMR) | Water content (KF) | XRPD |
|---|---|---|---|---|---|
| Ethyl acetate | 75% | 99.79% | <0.1% w/w [0.05% w/w] | 5.4% w/w | Form B |
| Isopropyl acetate | 80% | Not obtained | Not obtained | Not obtained | Predominantly amorphous |
| Iso-propanol | 83% | 99.78% | <0.1% w/w [0.02% w/w] | 5.7% w/w | Form B |

The scaled-up reactions had not undergone any conversion into their target forms after 4 days stirring @ 40-45° C. (IPC by XRPD). Each reaction was seeded with Form B (0.1% wt) at the 4 day set point. After 2 days further stirring (6 days in total), Form B was generated from ethyl acetate and isopropyl alcohol, while the isopropyl acetate suspension was unchanged (IPC XRPD). After 11 days stirring, the isopropyl acetate suspension consisted of amorphous material that contained a small quantity Form B (IPC, XRPD). Form B was isolated from ethyl acetate (75% th.) and isopropanol (83% th.), while the product isolated from isopropyl acetate was amorphous.

Alternatively, Form B of Compound 1 was obtained by stirring Form A in IPA/water (50/1, v/v), at 40-45° C. for 12 days. Form B contained 7% w/w water. Alternatively, Form B was obtained from stirring Form A in ethyl acetate at 40-45° C., for 12 days. The results showed Form B as the major component. Alternatively, an approximately equal parts mixture of Form A and Form B was produced by stirring Form A in isopropyl acetate at 40-45° C., for 12 days. The mixture was based on the diffraction pattern.

Form B was subjected to 75% RH at 15-25° C. for 1-2 days, which re-generated Form A.

Mixtures of Forms A and B were subjected to 75% RH at 15-25° C. for 1-2 days, which re-generated Form A.

Example 3

Preparation of Form C of Compound 1

Form C of Compound 1 was generated by the addition of anti-solvent (IPA, 30 vol) to a solution of Form A of Compound 1 in aqueous ethanol (1/5, v/v).

Form C was subjected to 75% RH at 15-25° C. for 22 h, which provided a gain of 18.5% w/w, which re-generated Form A.

Example 4

Preparation of Form D of Compound 1

Form A (1.0 g) was dried at 60° C. under reduced pressure for 24 h. During this time the sample decreased in weight by −7.3% w/w. XRPD Analysis of a specimen of this material confirmed that starting material, Form A had converted into Form D. The product was cooled to 18-23° C. under reduced pressure, vented with nitrogen and transferred to a container, also under nitrogen.

XRPD Analysis of the dried product showed it consisted of Form D. Analysis by KF showed the dried product only contained 1.0% w/w water, in contrast to 2% w/w when Form D was prepared on a smaller scale.

Samples of Form D were placed in humidity chambers at 45%, 60% and 75% RH at 18-23° C. and their weight changes were monitored at intervals up to 48 h. The results are provided in the Table below.

| Time | | Relative humidities of the enclosures at 18-23° C. | | |
|---|---|---|---|---|
| | | 43% RH | 60% RH | 75% RH |
| 0 h | XRPD (Initial wt.) | Form D (6.68 mg) | Form D (10.38 mg) | Form D (11.09 mg) |
| 4 h | Δ wt. (cumulative) | +0.60 mg, (+3.6% w/w) | +0.81 mg, (+7.8% w/w) | +0.88 mg, (+7.9% w/w) |
| | Observations | No change in appearance, still mobile | Slightly darker, slightly sticky, not mobile | Slightly darker, slightly sticky, not mobile |
| 24 h | Δ wt. (cumulative) | +0.78 mg, (+4.7% w/w) | +1.03 mg, (+9.9% w/w) | +1.48 mg, (+13.3% w/w) |
| | Observations | Very slightly darker in colour but still mobile | Slightly darker, slightly sticky, not mobile | A little darker, slightly sticky, not mobile |

| Time | Relative humidities of the enclosures at 18-23° C. | | |
|---|---|---|---|
| | 43% RH | 60% RH | 75% RH |
| 48 h Δ wt. (cumulative) | +1.61 mg, (+9.6% w/w) | +1.20 mg, (+11.6% w/w) | +1.73 mg, (+15.6% w/w) |
| Observations | Slightly darker in colour but still mobile | Slightly darker, slightly sticky, not mobile | Mid yellow, slightly sticky, not mobile |
| XRPD (Final wt.) | Form A (8.29 mg) | Form A (11.58 mg) | Form A (12.82 mg) |

Example 5

Preparation of the Amorphous Form of Compound 1

The amorphous form of Compound 1 was prepared by the thermal dehydration of Form A by DSC, followed by re-hydration at 43% RH at 15-25° C., for 1 day, to provide the amorphous form (99.44% by area at 222 nm).

A specimen of Form A (7.72 mg) was heated from 20° C. to 120° C. and cooled back to 20° C. (±10° C./min). The weight lost during this heat/cool cycle was 0.55 mg (~7% w/w) which corresponded to the water content previously determined by KF titre as 7% w/w.

The spent DSC crucible containing the anhydrate was then exposed to 43% RH for 64 h at 18-23° C. and re-weighed. All of the weight lost on heating was regained and the sample then weighed 7.74 mg. The DSC thermogram of the now hydrated sample contained two events, one with onset 84° C. (broad), presumably dehydration and a second, smaller event with onset 132° C. The second small event was attributed to decomposition and not to melting of a new crystalline form. This was later confirmed by XRPD analysis of the rehydrated-anhydrate which was found to be amorphous.

A second specimen of Form A (6.10 mg) underwent the same heat-cool cycle. The weight lost during this heat/cool cycle was 0.37 mg (~6% w/w). The spent DSC crucible containing the anhydrate was exposed to 43% RH for 22 h at 18-23° C. and re-weighed. The majority of the weight lost on heating was regained and the sample then weighed 6.05 mg.

The residue was expressed from the spent DSC crucible and analysed by XRPD and confirmed as amorphous. The chemical identity was confirmed by Rel RT by HPLC and the chemical purity was 99.44% (by area at 222 nm).

Alternatively, the amorphous form of Compound 1 was prepared by dissolving Form A at 18-23° C. under anhydrous conditions in sec-butanol, isobutanol, or isopropanol.

Alternatively, the amorphous form of Compound 1 was prepared by dissolving Form A at 40-45° C. under anhydrous conditions in anisole, isopropanol and toluene.

Alternatively, the amorphous form of Compound 1 was prepared by slow evaporation of Form A in DCM.

Alternatively, the amorphous form of Compound 1 was prepared by slow evaporation of Form A in DCM/water in a 50/1 v/v solution.

Alternatively, the amorphous form of Compound 1 was prepared by crystallization of Form A under anhydrous conditions from anisole/TBME (2/1, v/v), sec-butanol, ethyl acetate, isopropyl acetate, methylisobutyl ketone, isobutanol, isopropanol and toluene/TBME (2/1, v/v).

Alternatively, the amorphous form of Compound 1 was prepared by stirring Form A in isopropyl acetate at 40-45° C. for 11 days under anhydrous conditions (the amorphous product contained low levels of Form B).

Alternatively, the amorphous form of Compound 1 was prepared by precipitation by addition of TBME (30 vol) to a solution of Form A in ethanol (6 vol).

Example 6

Forms A-D after Inter-Conversion

A mixture of Forms A, B, C, and D (present in equal amounts) of Compound 1 was stirred in TBME/ethanol/water (20/5/1, v/v/v) at 18-23° C. for 4 days. The mixture converted into Form A.

Form A of Compound 1 was stirred in TBME/ethanol/water (20/5/1, v/v/v) at 18-23° C. for 4 days. The mixture remained Form A. Form B of Compound 1 was stirred in TBME/ethanol/water (20/5/1, v/v/v) at 18-23° C. for 4 days. The mixture converted into Form A. Form C of Compound 1 was stirred in TBME/ethanol/water (20/5/1, v/v/v) at 18-23° C. for 4 days. The mixture converted into Form A. Form D of Compound 1 was stirred in TBME/ethanol/water (20/5/1, v/v/v) at 18-23° C. for 4 days. The mixture converted into Form A.

The amorphous form of Compound 1 was dissolved and remained in solution even when cooled to 5-8° C. for 20 h after stirring under the same conditions.

Example 7

Forms in TBME/Ethanol/Water (20/5/1, v/v/v)

A reaction vessel was charged with a mixture of Forms A-D of Compound 1 (25 mg, 1.0 wt.). A solution of TBME/EtOH/water (20/5/1, 10 vol) was added, and was stirred at 18-23° C. for 4 days. The solid was isolated by filtration, washed with recycled mother liquors, and dried under vacuum under a $N_2$ atmosphere.

A reaction vessel was charged with Form A of Compound 1 (25 mg, 1.0 wt.). A solution of TBME/EtOH/water (20/5/1, 10 vol) was added, and was stirred at 18-23° C. for 4 days. The solid was isolated by filtration, washed with recycled mother liquors, and dried under vacuum under a $N_2$ atmosphere.

A reaction vessel was charged with Form B of Compound 1 (25 mg, 1.0 wt.). A solution of TBME/EtOH/water (20/5/1, 10 vol) was added, and was stirred at 18-23° C. for 4 days. The solid was isolated by filtration, washed with recycled mother liquors, and dried under vacuum under a $N_2$ atmosphere.

A reaction vessel was charged with Form C of Compound 1 (25 mg, 1.0 wt.). A solution of TBME/EtOH/water (20/5/1, 10 vol) was added, and was stirred at 18-23° C. for 4 days. The solid was isolated by filtration, washed with recycled mother liquors, and dried under vacuum under a $N_2$ atmosphere.

A reaction vessel was charged with Form D of Compound 1 (25 mg, 1.0 wt.). A solution of TBME/EtOH/water (20/5/1, 10 vol) was added, and was stirred at 18-23° C. for 4 days. The solid was isolated by filtration, washed with recycled mother liquors, and dried under vacuum under a $N_2$ atmosphere.

The results are provided in the table below. The mixture of Forms A-D (combined in equal amounts by weight) of Compound 1, and each of Forms A, B, C, and D, converted into Form A. The water contents of Form A (products) corresponded to Form A.2$H_2O$ (dihydrated), and were not solvated.

TABLE

Form inter-conversion and characterisation of isolated solids.

| Input form(s) | Input (mg) | Output (mg) | Yield % th. | Output form | Water content input (KF) | Water content output (KF) | Solvent content ($^1$H NMR) |
|---|---|---|---|---|---|---|---|
| Form A | 25.4 | 71.4 | 71% | Form A | 6.1% w/w | 7.3% w/w | EtOH n.d, TBME <0.1% w/w [0.009% w/w] |
| Form B | 24.6 | | | | 5.7% w/w | | |
| Form C | 24.9 | | | | 5.7% w/w | | |
| Form D | 25.2 | | | | 2.5% w/w | | |
| Form A | 99.8 | 75.1 | 75% | Form A | 6.1% w/w | 7.6% w/w | EtOH n.d, TBME <0.1% w/w [0.01% w/w] |
| Form B | 101.9 | 74 | 73% | Form A | 5.7% w/w | 6.9% w/w | EtOH n.d, TBME <0.1% w/w [0.01% w/w] |
| Form C | 45.4 | 25.8 | 57% | Form A | 5.7% w/w | 8.1% w/w | EtOH <0.1% w/w [0.02% w/w], TBME <0.1% w/w [0.01% w/w] |
| Form D | 101.4 | 74.7 | 74% | Form A | 2.5% w/w | 7.7% w/w | EtOH n.d, TBME <0.1% w/w [0.005% w/w] |
| Amorphous | 64 | Dissolved | *** | *** | *** | *** | *** |

Example 8

Inter-Conversion of Forms and Conversion to Form D

A sample of Form A was dried for 48 h under vacuum at 60° C. and reweighed. The material decreased in weight by 9.30% w/w.

Re-analysis of the material by XRPD showed the dried material to be of Form D. HPLC and $^1$H NMR confirmed the material was still Compound 1, and that decomposition had not occurred. Analysis by KF showed 2.1% w/w water.

Accurately weighed samples of Form D were placed in humidity chambers at 45%, 60% and 75% R.H. and monitored for weight changes over 48 h. The results are summarised in the table below.

TABLE 2

Comparative hygroscopicity study of Form D

| Time (hrs) | | 45% R.H. (Input: 16.68 mg) Form D | 60% R.H. (Input: 10.38 mg) Form D | 75% R.H. (Input: 11.09 mg) Form D |
|---|---|---|---|---|
| 4 | Wgt increase (cumulative) Comments | 0.60 mg 3.6% w/w No change in appearance, still mobile | 0.81 mg 7.8% w/w Slightly darker, slightly sticky, not mobile | 0.88 mg 7.9% w/w Slightly darker, slightly sticky, not mobile |
| 24 | Wgt increase (cumulative) Comments | 0.78 mg 4.7% w/w Very slightly darker in colour but still mobile | 1.03 mg 9.9% w/w Slightly darker, slightly sticky, not mobile | 1.48 mg 13.3% w/w A little darker, slightly sticky, not mobile |
| 48 | Wgt increase (cumulative) Comments | 1.61 mg 9.6% w/w Slightly darker in colour but | 1.20 mg 11.6% w/w Slightly darker, slightly | 1.73 mg 15.6% w/w Mid yellow, slightly sticky, |

TABLE 2-continued

Comparative hygroscopicity study of Form D

| Time (hrs) | 45% R.H. (Input: 16.68 mg) Form D | 60% R.H. (Input: 10.38 mg) Form D | 75% R.H. (Input: 11.09 mg) Form D |
|---|---|---|---|
| | still mobile XRPD - Form A | sticky, not mobile XRPD - Form A | not mobile XRPD - Form A |

XRPD analysis of all three solids after 48 hours in the humidity chambers showed that they had reverted to Form A.

The reactions conditions were repeated on a 1.0 g scale: a sample of Form A was dried for 24 hr under vacuum at 60° C. and reweighed. The material decreased in weight by 7.30% w/w. A sample of the material showed the material to have converted into Form D after 24 h. The material was allowed to cool to ambient temperature under vacuum before releasing the vacuum with nitrogen and transferring the Form D into a poly-tub under nitrogen. Analysis of the bulk of the material by XRPD showed the dried material to be Form D. Analysis by KF showed 1.0% w/w water.

Example 9

Equilibration Screens

Portions of Compound 1 (100 mg, 1.0 wt.) were charged to the vessels, solvents (10 vol) were added and reaction bank 1 (×10, A0333-122-A2 to J2) was stirred for 12 days at 18 to 23° C., whilst reaction bank 2 (×10, A0333-122-K2 to T2) was stirred for 12 d at 40 to 45° C. Products were isolated by filtration, washed with recycled mother liquors and dried on the filter under a stream of nitrogen (Table A).

TABLE A

Isolated products from the anhydrous equilibration screens.

| Solvent (10 vol) | Temperature | Yield (th.) | Appearance | Form (XRPD) |
|---|---|---|---|---|
| Anisole | 18-23° C. | 85% | White solid | A |
| sec-Butanol (2-Butanol) | 18-23° C. | 60% | Yellow solid | Amorphous (trace A) |
| t-Butyl methyl ether | 18-23° C. | 80% | Pale yellow solid | A |
| Cumene (isopropylbenzene) | 18-23° C. | 80% | Pale yellow solid | A |
| Ethyl acetate | 18-23° C. | 74% | Yellow solid | A |
| Isopropyl acetate | 18-23° C. | 81% | Yellow solid | A |
| Methylisobutyl ketone | 18-23° C. | 91% | Pale green solid | A |
| Isobutanol (2-Methyl-1-propanol) | 18-23° C. | 21% | Yellow solid | Amorphous |
| Isopropanol (2-Propanol) | 18-23° C. | 46% | Dark yellow solid | Amorphous (trace A) |
| Toluene | 18-23° C. | 83% | Pale yellow powder | A |
| Anisole | 40-45° C. | 74% | Green solid | Amorphous |
| sec-Butanol (2-Butanol) | 40-45° C. | 28% | Brown solid | Amorphous |
| t-Butyl methyl ether | 40-45° C. | 88% | Yellow solid | A |
| Cumene (isopropylbenzene) | 40-45° C. | 69% | Yellow solid | A |
| Ethyl acetate | 40-45° C. | 80% | Pale yellow solid | A + B |
| Isopropyl acetate | 40-45° C. | 86% | Pale yellow solid | A + B |
| Methylisobutyl ketone | 40-45° C. | *** | Vial cracked | *** |
| Isobutanol (2-Methyl-1-propanol) | 40-45° C. | *** | Deliquesced | *** |
| Isopropanol (2-Propanol) | 40-45° C. | 35% | Brown solid | Amorphous |
| Toluene | 40-45° C. | 90% | Green solid | Amorphous (trace A) |

Aqueous Equilibration Screens

Portions of Compound 1 (100 mg, 1.0 wt.) were charged to the vessels, aqueous solvents (solvent/water, 50/1, 10 vol) were added and reaction bank 1 (×10, A0333-130-A2 to J2) was stirred for 12 days at 18 to 23° C., while reaction bank 2 (×10, A0333-130-K2 to T2) was stirred for 12 d at 40 to 45° C. Products were isolated by filtration, washed with recycled mother liquors and dried on the filter under a stream of nitrogen (Table B).

TABLE B

Isolated products from the aqueous equilibration screens.

| Solvent (10 vol)/water (0.2 vol, 5 eq.) | Temperature | Yield (th.) | Appearance | Form (XRPD) |
|---|---|---|---|---|
| Anisole | 18-23° C. | 41% | Pale green solid | A |
| sec-Butanol (2-Butanol) | 18-23° C. | 80% | Off-white powder | A |
| t-Butyl methyl ether | 18-23° C. | 64% | Pale green solid | A |
| Cumene (isopropylbenzene) | 18-23° C. | *** | Yellow gum, not filtered | *** |
| Ethyl acetate | 18-23° C. | 56% | Yellow solid | A |
| Isopropyl acetate | 18-23° C. | 76% | Yellow solid | A |
| Methylisobutyl ketone | 18-23° C. | 81% | Green solid | A |
| Isobutanol (2-Methyl-1-propanol) | 18-23° C. | 74% | Pale yellow solid | A |
| Isopropanol (2-Propanol) | 18-23° C. | 77% | Off-white solid | A |
| Toluene | 18-23° C. | 48% | Pale yellow solid | A |
| Anisole | 40-45° C. | 62% | Yellow solid | A |
| sec-Butanol (2-Butanol) | 40-45° C. | 83% | Off-white solid | A |
| t-Butyl methyl ether | 40-45° C. | 53% | Pale green solid | A |
| Cumene (isopropylbenzene) | 40-45° C. | 45% | Yellow solid | A |
| Ethyl acetate | 40-45° C. | *** | Brown oily residue | *** |
| Isopropyl acetate | 40-45° C. | 80% | Yellow solid | A |
| Methylisobutyl ketone | 40-45° C. | 82% | Off white solid | A |
| Isobutanol (2-Methyl-1-propanol) | 40-45° C. | 13% | Pale yellow solid | A (highly crystalline) |
| Isopropanol (2-Propanol) | 40-45° C. | 75% | Off-white powder | B |
| Toluene | 40-45° C. | 74% | Pale yellow solid | A |

Form B was obtained after stirring in IPA/water (50/1, v/v, 40-45° C.), and contained <0.1% w/w IPA (by $^1$H NMR), 7% water (by KF titre) and was 99.98% by HPLC area (at 222 nm). Mixtures of Form A+B were obtained after stirring in ethyl acetate and isopropyl acetate (40-45° C.). Both products above exhibited markedly different dehydration characteristics from starting material by DSC. Form A+B (which consisted of mostly Form B) was generated from anhydrous ethyl acetate (40-45° C.), while stirring Compound 1 in ethyl acetate/water (50/1, v/v) at the same temperature gave a brown oily residue. Form B crystallised from isopropanol/water (50/1, v/v, 40-45° C.), and yet remained as Form A at 18-23° C. When water was not present amorphous solids were generated from isopropanol at both temperatures. Products isolated from isobutanol and isopropanol were particularly crystalline. Form A (isostructural with starting Form A) and one alternative polymorphic form (Form B) were generated during the equilibration screens.

Example 10

Form A Crystal Data and Structural Refinement

Diffractometer: Rigaku AFC12 goniometer equipped with an enhanced sensitivity (HG) Saturn724+ detector mounted at the window of an FR-E+ SuperBright molybdenum rotating anode generator with HF Varimax optics (100 μm focus).

Cell determination, Data collection, Data reduction and cell refinement & Absorption correction: CrystalClear-SM Expert 2.0 r7 (Rigaku, 2011).

Structure solution: SHELXS97 (Sheldrick, G. M. (2008). *Acta Cryst.* A64, 112-122). Structure refinement: SHELXL2012 (G. M. Sheldrick (2012), University of Göttingen, Germany).

Graphics: CrystalMaker: a crystal and molecular structures program for Mac and Windows. CrystalMaker Software Ltd, Oxford, England (www.crystalmaker.com).

Special details: All non-water hydrogens were located in the difference map and then placed in calculated positions and refined using a riding model. The water hydrogens were treated as partially riding on the oxygen atoms with close contacts restricted and their final positions should be treated with some caution.

Empirical formula $C_{18}H_{27}NNa_2O_9S$
Formula weight 479.44
Temperature 100(2) K
Wavelength 0.71073 Å
Crystal system Monoclinic
Space group $P2_1$
Unit cell dimensions a=16.073(4) Å
b=5.7900(13) Å β=108.095(5)°
c=25.467(6) Å
Volume 2252.8(9) Å$^3$
Z 4 (Z-=2)
Density (calculated) 1.414 Mg/m$^3$
Absorption coefficient 0.231 mm$^{-1}$
F(000) 1008
Crystal Lath; Pale Green
Crystal size 0.240×0.030×0.010 mm$^3$
Orange for data collection 3.035-27.481°
Index ranges −20≤h≤20, −6≤k≤7, −32≤l≤33
Reflections collected 19014
Independent reflections 9066 [$R_{int}$=0.0294]
Completeness to θ=25.242° 99.6%
Absorption correction Semi-empirical from equivalents
Max. and min. transmission 1.000 and 0.872
Refinement method Full-matrix least-squares on $F^2$
Data/restraints/parameters 9066/19/587
Goodness-of-fit on $F^2$ 1.051
Final R indices [$F^2$>2σ($F^2$)] R1=0.0420, wR2=0.0811
R indices (all data) R1=0.0468, wR2=0.0837
Absolute structure parameter 0.08(3)
Hooft parameter 0.06(4)
Largest diff. peak and hole 0.436 and −0.288 e Å$^{-3}$

TABLE 3

Atomic coordinates [×10$^4$], equivalent isotropic displacement parameters [Å$^2$ × 10$^3$] and site occupancy factors. $U_{eq}$ is defined as one third of the trace of the orthogonalized $U^{ij}$ tensor.

| Atom | x | y | z | $U_{eq}$ | S.o.f. |
|---|---|---|---|---|---|
| Na1 | 5625(1) | 9569(2) | 7863(1) | 17(1) | 1 |
| Na2 | 7141(1) | 12706(2) | 7404(1) | 20(1) | 1 |
| S101 | 7301(1) | 4546(1) | 9446(1) | 21(1) | 1 |
| N101 | 6336(2) | 7116(4) | 8638(1) | 16(1) | 1 |
| O101 | 4911(1) | 2528(4) | 8143(1) | 22(1) | 1 |
| O102 | 4723(1) | 6186(4) | 7840(1) | 17(1) | 1 |
| O103 | 7135(1) | 10197(4) | 8098(1) | 6(1) | 1 |
| O104 | 8433(1) | 13106(4) | 8208(1) | 20(1) | 1 |
| O105 | 8596(1) | 15084(4) | 7239(1) | 24(1) | 1 |
| O106 | 8494(2) | 12019(4) | 6287(1) | 25(1) | 1 |
| O107 | 7797(1) | 7845(4) | 5826(1) | 27(1) | 1 |
| C101 | 5062(2) | 4658(6) | 8196(1) | 15(1) | 1 |
| C102 | 5708(2) | 5476(5) | 8754(1) | 17(1) | 1 |
| C103 | 5177(2) | 6836(6) | 9061(1) | 23(1) | 1 |
| C104 | 6223(2) | 3451(6) | 9098(1) | 24(1) | 1 |
| C105 | 7120(2) | 6875(5) | 8961(1) | 15(1) | 1 |
| C106 | 7859(2) | 8372(6) | 8976(1) | 16(1) | 1 |
| C107 | 8633(2) | 8220(6) | 9431(1) | 22(1) | 1 |
| C108 | 9332(2) | 9668(7) | 9486(1) | 27(1) | 1 |
| C109 | 9286(2) | 11342(6) | 9080(1) | 23(1) | 1 |
| C110 | 8549(2) | 11506(6) | 8629(1) | 18(1) | 1 |
| C111 | 7800(2) | 10005(5) | 8546(1) | 15(1) | 1 |
| C112 | 9130(2) | 14693(6) | 8251(1) | 21(1) | 1 |
| C113 | 8859(2) | 16278(6) | 7756(1) | 23(1) | 1 |
| C114 | 9299(2) | 13916(6) | 7134(1) | 24(1) | 1 |
| C115 | 9148(2) | 13720(6) | 6514(1) | 25(1) | 1 |
| C116 | 8421(2) | 11446(6) | 5728(1) | 27(1) | 1 |
| C117 | 7648(2) | 9908(6) | 5511(1) | 26(1) | 1 |
| C118 | 7043(2) | 6434(7) | 5724(2) | 34(1) | 1 |
| Na3 | 4471(1) | 4756(2) | 6919(1) | 17(1) | 1 |
| Na4 | 3121(1) | 7142(2) | 7482(1) | 19(1) | 1 |
| S201 | 3077(1) | −1481(2) | 5707(1) | 24(1) | 1 |
| N201 | 3909(2) | 2367(4) | 6088(1) | 15(1) | 1 |
| O201 | 5181(1) | −2039(4) | 6773(1) | 24(1) | 1 |
| O202 | 5449(2) | 1666(4) | 6993(1) | 21(1) | 1 |
| O203 | 3035(1) | 4434(4) | 6830(1) | 16(1) | 1 |
| O204 | 1645(1) | 6970(4) | 6764(1) | 21(1) | 1 |
| O205 | 1051(2) | 8649(4) | 7668(1) | 27(1) | 1 |
| O206 | 1860(2) | 6852(4) | 8804(1) | 31(1) | 1 |
| O207 | 2664(2) | 2437(5) | 9153(1) | 36(1) | 1 |
| C201 | 5126(2) | 69(5) | 6656(1) | 17(1) | 1 |
| C202 | 4611(2) | 787(5) | 6051(1) | 17(1) | 1 |
| C203 | 5231(2) | 2089(6) | 5806(1) | 25(1) | 1 |
| C204 | 4192(2) | −1311(6) | 5688(1) | 22(1) | 1 |
| C205 | 3147(2) | 1426(5) | 5944(1) | 15(1) | 1 |
| C206 | 2336(2) | 2593(5) | 5955(1) | 16(1) | 1 |
| C207 | 1559(2) | 2257(6) | 5511(1) | 22(1) | 1 |
| C208 | 816(2) | 3524(7) | 5473(1) | 24(1) | 1 |
| C209 | 830(2) | 5168(6) | 5880(1) | 21(1) | 1 |
| C210 | 1571(2) | 5447(6) | 6330(1) | 18(1) | 1 |
| C211 | 2356(2) | 4145(5) | 6390(1) | 15(1) | 1 |
| C212 | 940(2) | 8568(6) | 6706(1) | 23(1) | 1 |
| C213 | 1155(2) | 10003(6) | 7222(1) | 26(1) | 1 |
| C214 | 1300(2) | 9951(7) | 8164(1) | 27(1) | 1 |
| C215 | 1192(2) | 8545(7) | 8638(1) | 30(1) | 1 |
| C216 | 1873(2) | 5694(6) | 9305(1) | 30(1) | 1 |
| C217 | 2700(2) | 4363(7) | 9511(1) | 33(1) | 1 |
| C218 | 3456(3) | 1173(8) | 9277(2) | 39(1) | 1 |
| O1W | 6763(2) | 16440(5) | 7395(1) | 22(1) | 1 |
| O2W | 7342(2) | 10062(4) | 6794(1) | 29(1) | 1 |
| O3W | 3308(2) | 11032(4) | 7588(1) | 33(1) | 1 |
| O4W | 2946(2) | 5210(5) | 8203(1) | 40(1) | 1 |

TABLE 4

Bond lengths [Å] and angles [°].

| | | | |
|---|---|---|---|
| Na1—O101$^i$ | 2.295(2) | C114—C115 | 1.525(4) |
| Na1—O103 | 2.341(2) | C116—C117 | 1.488(5) |
| Na1—N101 | 2.412(3) | Na3—O203 | 2.256(2) |
| Na1—O102 | 2.427(2) | Na3—O201$^i$ | 2.268(3) |
| Na1—O202$^i$ | 2.465(2) | Na3—O202 | 2.350(3) |
| Na1—O201$^i$ | 2.802(3) | Na3—N201 | 2.453(3) |
| Na1—C201$^i$ | 2.940(3) | Na3—C201 | 3.059(3) |
| Na2—O1W | 2.244(3) | Na3—Na4 | 3.2566(16) |
| Na2—O2W | 2.273(3) | Na4—O4W | 2.243(3) |
| Na2—O103 | 2.291(2) | Na4—O203 | 2.256(2) |
| Na2—O104 | 2.433(2) | Na4—O3W | 2.277(3) |
| Na2—O202$^i$ | 2.663(3) | Na4—O204 | 2.507(2) |

TABLE 4-continued

Bond lengths [Å] and angles [°].

| | | | |
|---|---|---|---|
| Na2—O105 | 2.854(3) | S201—C205 | 1.779(3) |
| S101—C105 | 1.791(3) | S201—C204 | 1.811(3) |
| S101—C104 | 1.799(3) | N201—C205 | 1.284(4) |
| N101—C105 | 1.280(4) | N201—C202 | 1.479(4) |
| N101—C102 | 1.481(4) | O201—C201 | 1.253(4) |
| O101—C101 | 1.256(4) | O201—Na3$^{ii}$ | 2.268(2) |
| O101—Na1$^{ii}$ | 2.295(2) | O201—Na1$^{ii}$ | 2.802(3) |
| O102—C101 | 1.263(4) | O202—C201 | 1.258(4) |
| O102—Na3 | 2.400(2) | O202—Na1$^{ii}$ | 2.465(2) |
| O102—Na4 | 2.512(2) | O202—Na2$^{ii}$ | 2.663(3) |
| O103—C111 | 1.303(3) | O203—C211 | 1.309(3) |
| O104—C110 | 1.385(4) | O204—C210 | 1.390(4) |
| O104—C112 | 1.427(4) | O204—C212 | 1.435(4) |
| O105—C114 | 1.412(4) | O205—C214 | 1.419(4) |
| O105—C113 | 1.431(4) | O205—C213 | 1.432(4) |
| O106—C115 | 1.425(4) | O206—C215 | 1.419(4) |
| O106—C116 | 1.431(3) | O206—C216 | 1.436(4) |
| O107—C117 | 1.418(4) | O207—C218 | 1.416(4) |
| O107—C118 | 1.417(4) | O207—C217 | 1.429(4) |
| C101—C102 | 1.551(4) | C201—C202 | 1.562(4) |
| C101—Na3 | 3.092(3) | C201—Na1$^{ii}$ | 2.940(3) |
| C102—C103 | 1.539(4) | C202—C203 | 1.528(4) |
| C102—C104 | 1.542(4) | C202—C204 | 1.548(4) |
| C105—C106 | 1.462(4) | C205—C206 | 1.477(4) |
| C106—C107 | 1.415(4) | C206—C207 | 1.413(4) |
| C106—C111 | 1.427(4) | C206—C211 | 1.420(4) |
| C107—C108 | 1.373(5) | C207—C208 | 1.379(5) |
| C108—C109 | 1.403(5) | C208—C209 | 1.404(5) |
| C109—C110 | 1.373(4) | C209—C210 | 1.381(4) |
| C110—C111 | 1.445(4) | C210—C211 | 1.437(4) |
| C112—C113 | 1.510(4) | C212—C213 | 1.501(4) |
| C214—C215 | 1.510(5) | C216—C217 | 1.485(5) |
| O101$^{i}$—Na1—O103 | 112.53(9) | C201$^{i}$—Na1—Na3$^{i}$ | 50.36(7) |
| O101$^{i}$—Na1—N101 | 109.95(9) | Na2—Na1—Na3$^{i}$ | 69.29(4) |
| O103—Na1—N101 | 72.08(8) | Na3—Na1—Na3$^{i}$ | 97.42(4) |
| O101$^{i}$—Na1—O102 | 104.93(8) | O101$^{i}$—Na1—Na4 | 77.29(7) |
| O103—Na1—O102 | 134.11(9) | O103—Na1—Na4 | 168.82(7) |
| N101—Na1—O102 | 70.88(8) | N101—Na1—Na4 | 99.98(7) |
| O101$^{i}$—Na1—O202$^{i}$ | 88.97(9) | O102—Na1—Na4 | 34.86(5) |
| O103—Na1—O202$^{i}$ | 88.50(8) | O202$^{i}$—Na1—Na4 | 97.23(7) |
| N101—Na1—O202$^{i}$ | 156.76(9) | O201$^{i}$—Na1—Na4 | 73.80(5) |
| O102—Na1—O202$^{i}$ | 118.33(8) | C201$^{i}$—Na1—Na4 | 81.76(6) |
| O101$^{i}$—Na1—O201$^{i}$ | 123.86(8) | Na2—Na1—Na4 | 146.25(4) |
| O103—Na1—O201$^{i}$ | 103.29(7) | Na3—Na1—Na4 | 48.77(3) |
| N101—Na1—O201$^{i}$ | 121.70(9) | Na3$^{i}$—Na1—Na4 | 82.79(3) |
| O102—Na1—O201$^{i}$ | 74.99(7) | O1W—Na2—O2W | 137.54(10) |
| O202$^{i}$—Na1—O201$^{i}$ | 49.47(7) | O1W—Na2—O103 | 123.51(9) |
| O101$^{i}$—Na1—C201$^{i}$ | 104.50(9) | O2W—Na2—O103 | 97.80(9) |
| O103—Na1—C201$^{i}$ | 100.16(8) | O1W—Na2—O104 | 94.25(9) |
| N101—Na1—C201$^{1}$ | 145.05(10) | O2W—Na2—O104 | 111.97(10) |
| O102—Na1—C201$^{1}$ | 94.99(8) | O103—Na2—O104 | 67.51(8) |
| O202$^{i}$—Na1—C201$^{i}$ | 24.99(8) | O1W—Na2—O202$^{i}$ | 88.48(9) |
| O201$^{i}$—Na1—C201$^{i}$ | 25.06(8) | O2W—Na2—O202$^{i}$ | 85.62(9) |
| O101$^{i}$—Na1—Na2 | 100.50(7) | O103—Na2—O202$^{i}$ | 84.90(8) |
| O103—Na1—Na2 | 40.05(5) | O104—Na2—O202$^{i}$ | 148.53(8) |
| N101—Na1—Na2 | 112.04(7) | O1W—Na2—O105 | 76.45(8) |
| O102—Na1—Na2 | 151.51(6) | O2W—Na2—O105 | 85.87(8) |
| O202$^{i}$—Na1—Na2 | 49.06(6) | O103—Na2—O105 | 128.30(8) |
| O201$^{i}$—Na1—Na2 | 80.31(6) | O104—Na2—O105 | 63.55(7) |
| C201$^{i}$—Na1—Na2 | 66.02(7) | O202$^{i}$—Na2—O105 | 146.58(8) |
| O101$^{i}$—Na1—Na3 | 123.73(7) | O1W—Na2—Na1 | 106.68(7) |
| O103—Na1—Na3 | 122.93(7) | O2W—Na2—Na1 | 97.99(7) |
| N101—Na1—Na3 | 95.80(8) | O103—Na2—Na1 | 41.10(6) |
| O102—Na1—Na3 | 38.38(5) | O104—Na2—Na1 | 105.49(6) |
| O202$^{i}$—Na1—Na3 | 83.93(7) | O202$^{i}$—Na2—Na1 | 44.38(5) |
| O201$^{i}$—Na1—Na3 | 36.78(5) | O105—Na2—Na1 | 168.99(6) |
| C201$^{i}$—Na1—Na3 | 59.04(7) | C105—S101—C104 | 89.94(15) |
| Na2—Na1—Na3 | 115.07(4) | C105—N101—C102 | 113.5(2) |
| O101$^{i}$—Na1—Na3$^{i}$ | 55.47(6) | C105—N101—Na1 | 135.3(2) |
| O103—Na1—Na3$^{i}$ | 106.99(6) | C102—N101—Na1 | 111.20(18) |
| N101—Na1—Na3$^{i}$ | 164.45(8) | C101—O101—Na1$^{ii}$ | 131.9(2) |
| O102—Na1—Na3$^{i}$ | 115.88(6) | C101—O102—Na3 | 111.35(18) |
| O202$^{i}$—Na1—Na3$^{i}$ | 34.26(5) | C101—O102—Na1 | 115.21(19) |
| O201$^{i}$—Na1—Na3$^{i}$ | 73.82(5) | Na3—O102—Na1 | 102.73(8) |
| C101—O102—Na4 | 125.51(18) | O105—C114—C115 | 110.6(3) |
| Na3—O102—Na4 | 83.03(7) | O106—C115—C114 | 109.3(2) |
| Na1—O102—Na4 | 111.62(9) | O106—C116—C117 | 108.0(2) |
| C111—O103—Na2 | 122.04(18) | O107—C117—C116 | 108.6(3) |

TABLE 4-continued

Bond lengths [Å] and angles [°].

| | | | |
|---|---|---|---|
| C111—O103—Na1 | 135.57(17) | O203—Na3—O201$^i$ | 127.03(10) |
| Na2—O103—Na1 | 98.85(8) | O203—Na3—O202 | 125.65(10) |
| C110—O104—C112 | 117.3(2) | O201$^i$—Na3—O202 | 106.15(9) |
| C110—O104—Na2 | 117.55(18) | O203—Na3—O102 | 89.05(8) |
| C112—O104—Na2 | 124.75(17) | O201$^i$—Na3—O102 | 86.39(9) |
| C114—O105—C113 | 112.3(2) | O202—Na3—O102 | 106.19(8) |
| C114—O105—Na2 | 122.5(2) | O203—Na3—N201 | 77.00(8) |
| C113—O105—Na2 | 96.85(16) | O201$^i$—Na3—N201 | 112.94(9) |
| C115—O106—C116 | 112.7(2) | O202—Na3—N201 | 72.42(9) |
| C117—O107—C118 | 113.5(3) | O102—Na3—N201 | 160.43(9) |
| O101—C101—O102 | 125.8(3) | O203—Na3—C201 | 108.39(8) |
| O101—C101—C102 | 116.8(3) | O201$^i$—Na3—C201 | 117.72(9) |
| O102—C101—C102 | 117.5(3) | O202—Na3—C201 | 22.34(8) |
| O101—C101—Na3 | 85.33(18) | O102—Na3—C201 | 123.69(9) |
| O102—C101—Na3 | 46.29(13) | N201—Na3—C201 | 51.02(8) |
| C102—C101—Na3 | 149.08(19) | O203—Na3—C101 | 94.29(8) |
| N101—C102—C103 | 107.0(2) | O201$^i$—Na3—C101 | 100.43(9) |
| N101—C102—C104 | 108.7(3) | O202—Na3—C101 | 85.54(8) |
| C103—C102—C104 | 112.7(2) | O102—Na3—C101 | 22.36(8) |
| N101—C102—C101 | 108.5(2) | N201—Na3—C101 | 143.81(10) |
| C103—C102—C101 | 107.6(2) | C201—Na3—C101 | 101.51(9) |
| C104—C102—C101 | 112.2(3) | O203—Na3—Na4 | 43.81(6) |
| C102—C104—S101 | 106.1(2) | O201$^i$—Na3—Na4 | 99.37(7) |
| N101—C105—C106 | 125.6(3) | O202—Na3—Na4 | 143.92(7) |
| N101—C105—S101 | 116.2(2) | O102—Na3—Na4 | 49.96(6) |
| C106—C105—S101 | 118.1(2) | N201—Na3—Na4 | 120.07(7) |
| C107—C106—C111 | 120.1(3) | C201—Na3—Na4 | 142.59(7) |
| C107—C106—C105 | 119.0(3) | C101—Na3—Na4 | 64.80(6) |
| C111—C106—C105 | 120.9(3) | O203—Na3—Na1 | 114.25(7) |
| C108—C107—C106 | 121.9(3) | O201$^i$—Na3—Na1 | 47.69(6) |
| C107—C108—C109 | 119.5(3) | O202—Na3—Na1 | 109.10(7) |
| C110—C109—C108 | 119.9(3) | O102—Na3—Na1 | 38.89(6) |
| C109—C110—O104 | 124.5(3) | N201—Na3—Na1 | 160.60(7) |
| C109—C110—C111 | 122.9(3) | C201—Na3—Na1 | 131.34(7) |
| O104—C110—C111 | 112.5(3) | C101—Na3—Na1 | 54.07(7) |
| O103—C111—C106 | 124.7(3) | Na4—Na3—Na1 | 70.67(4) |
| O103—C111—C110 | 119.7(3) | O203—Na3—Na1$^{ii}$ | 105.77(7) |
| C106—C111—C110 | 115.6(3) | O201$^i$—Na3—Na1$^{ii}$ | 123.98(7) |
| O104—C112—C113 | 108.1(2) | O202—Na3—Na1$^{ii}$ | 36.20(5) |
| O105—C113—C112 | 113.7(3) | O102—Na3—Na1$^{ii}$ | 76.21(6) |
| N201—Na3—Na1$^{ii}$ | 94.25(7) | C212—O204—Na4 | 125.99(18) |
| C201—Na3—Na1$^{ii}$ | 47.73(6) | C214—O205—C213 | 110.2(3) |
| C101—Na3—Na1$^{ii}$ | 53.88(6) | C215—O206—C216 | 112.8(2) |
| Na4—Na3—Na1$^{ii}$ | 107.88(4) | C218—O207—C217 | 113.9(3) |
| Na1—Na3—Na1$^{ii}$ | 97.42(4) | O201—C201—O202 | 124.8(3) |
| O4W—Na4—O203 | 105.17(10) | O201—C201—C202 | 118.1(3) |
| O4W—Na4—O3W | 116.16(11) | O202—C201—C202 | 117.2(3) |
| O203—Na4—O3W | 138.66(10) | O201—C201—Na1$^{ii}$ | 71.28(17) |
| O4W—Na4—O204 | 104.29(10) | O202—C201—Na1$^{ii}$ | 55.88(15) |
| O203—Na4—O204 | 66.93(8) | C202—C201—Na1$^{ii}$ | 161.15(19) |
| O3W—Na4—O204 | 100.75(9) | O201—C201—Na3 | 144.6(2) |
| O4W—Na4—O102 | 88.16(9) | O202—C201—Na3 | 45.24(15) |
| O203—Na4—O102 | 86.29(8) | C202—C201—Na3 | 82.34(16) |
| O3W—Na4—O102 | 95.28(9) | Na1$^{ii}$—C201—Na3 | 81.91(8) |
| O204—Na4—O102 | 152.50(8) | N201—C202—C203 | 109.2(3) |
| O4W—Na4—Na3 | 114.80(9) | N201—C202—C204 | 108.9(2) |
| O203—Na4—Na3 | 43.80(6) | C203—C202—C204 | 111.2(2) |
| O3W—Na4—Na3 | 112.99(8) | N201—C202—C201 | 106.4(2) |
| O204—Na4—Na3 | 105.73(6) | C203—C202—C201 | 108.7(3) |
| O102—Na4—Na3 | 47.01(5) | C204—C202—C201 | 112.3(3) |
| O4W—Na4—Na1 | 109.98(9) | C202—C204—S201 | 106.2(3) |
| O203—Na4—Na1 | 104.15(6) | N201—C205—C206 | 124.7(3) |
| O3W—Na4—Na1 | 63.10(7) | N201—C205—S201 | 116.9(2) |
| O204—Na4—Na1 | 145.71(6) | C206—C205—S201 | 118.4(2) |
| O102—Na4—Na1 | 33.52(6) | C207—C206—C211 | 120.8(3) |
| Na3—Na4—Na1 | 60.56(4) | C207—C206—C205 | 119.2(3) |
| C205—S201—C204 | 89.88(15) | C211—C206—C205 | 119.9(3) |
| C205—N201—C202 | 113.4(3) | C208—C207—C206 | 120.9(3) |
| C205—N201—Na3 | 123.33(18) | C207—C208—C209 | 119.6(3) |
| C202—N201—Na3 | 108.64(18) | C210—C209—C208 | 120.2(3) |
| C201—O201—Na3$^{ii}$ | 146.5(2) | C209—C210—O204 | 124.9(3) |
| C201—O201—Na1$^{ii}$ | 83.67(18) | C209—C210—C211 | 122.1(3) |
| Na3$^{ii}$—O201—Na1$^{ii}$ | 95.52(8) | O204—C210—C211 | 113.1(3) |
| C201—O202—Na3 | 112.4(2) | O203—C211—C206 | 124.0(3) |
| C201—O202—Na1$^{ii}$ | 99.13(18) | O203—C211—C210 | 119.8(3) |
| Na3—O202—Na1$^{ii}$ | 109.54(9) | C206—C211—C210 | 116.2(3) |
| C201—O202—Na2$^{ii}$ | 126.03(19) | O204—C212—C213 | 107.9(3) |
| Na3—O202—Na2$^{ii}$ | 115.82(10) | O205—C213—C212 | 109.8(3) |

TABLE 4-continued

Bond lengths [Å] and angles [°].

| | | | |
|---|---|---|---|
| Na1^(ii)—O202—Na2^(ii) | 86.56(8) | O205—C214—C215 | 110.8(3) |
| C211—O203—Na4 | 124.20(18) | O206—C215—C214 | 110.2(3) |
| C211—O203—Na3 | 130.67(16) | O206—C216—C217 | 108.7(3) |
| Na4—O203—Na3 | 92.39(8) | O207—C217—C216 | 109.0(3) |
| C210—O204—C212 | 117.2(2) | | |
| C210—O204—Na4 | 115.69(17) | | |

Symmetry transformations used to generate equivalent atoms:
^(i)x, y + 1, z
^(ii)x, y − 1, z

TABLE 5

Anisotropic displacement parameters [Å² × 10³].
The anisotropic displacement factor exponent takes the form: $-2\pi^2[h^2 a^{*2} U^{11} + \ldots + 2 h k a^* b^* U^{12}]$.

| Atom | $U^{11}$ | $U^{22}$ | $U^{33}$ | $U^{23}$ | $U^{13}$ | $U^{12}$ |
|---|---|---|---|---|---|---|
| Na1 | 18(1) | 16(1) | 16(1) | 2(1) | 3(1) | 2(1) |
| Na2 | 26(1) | 15(1) | 18(1) | 0(1) | 4(1) | 2(1) |
| S101 | 22(1) | 20(1) | 18(1) | 5(1) | 0(1) | 1(1) |
| N101 | 18(1) | 15(1) | 14(1) | 0(1) | 3(1) | −1(1) |
| O101 | 18(1) | 16(1) | 30(1) | −5(1) | 1(1) | 1(1) |
| O102 | 17(1) | 20(1) | 12(1) | 1(1) | 2(1) | 1(1) |
| O103 | 14(1) | 17(1) | 13(1) | 1(1) | −1(1) | −1(1) |
| O104 | 16(1) | 24(1) | 20(1) | 3(1) | 4(1) | −4(1) |
| O105 | 22(1) | 28(1) | 23(1) | 0(1) | 7(1) | −1(1) |
| O106 | 31(1) | 30(1) | 18(1) | −2(1) | 14(1) | −6(1) |
| O107 | 29(1) | 24(1) | 27(1) | 1(1) | 8(1) | 7(1) |
| C101 | 13(1) | 18(2) | 16(1) | −4(1) | 7(1) | −1(1) |
| C102 | 19(2) | 15(2) | 16(1) | 3(1) | 4(1) | −3(1) |
| C103 | 28(2) | 24(2) | 18(2) | −2(1) | 9(2) | −4(2) |
| C104 | 28(2) | 19(2) | 21(2) | 2(1) | 1(1) | −3(2) |
| C105 | 18(2) | 17(2) | 9(1) | −1(1) | 2(1) | 2(1) |
| C106 | 15(2) | 18(2) | 14(1) | −2(1) | 4(1) | 2(1) |
| C107 | 18(2) | 30(2) | 16(2) | 5(1) | 2(1) | 3(2) |
| C108 | 16(2) | 39(2) | 19(2) | 4(2) | −3(1) | −5(2) |
| C109 | 17(2) | 29(2) | 19(2) | −2(1) | 1(1) | −8(2) |
| C110 | 17(2) | 24(2) | 16(2) | −1(1) | 7(1) | 1(1) |
| C111 | 15(2) | 17(2) | 14(1) | −2(1) | 5(1) | 1(1) |
| C112 | 16(2) | 25(2) | 21(2) | −3(1) | 7(1) | −7(2) |
| C113 | 23(2) | 23(2) | 23(2) | −1(1) | 6(1) | −4(2) |
| C114 | 20(2) | 27(2) | 26(2) | 5(1) | 6(1) | 2(2) |
| C115 | 21(2) | 30(2) | 25(2) | 7(1) | 11(2) | 2(2) |
| C116 | 34(2) | 34(2) | 17(2) | 6(1) | 13(2) | 9(2) |
| C117 | 34(2) | 27(2) | 17(2) | 3(1) | 9(2) | 10(2) |
| C118 | 32(2) | 28(2) | 40(2) | −10(2) | 6(2) | 0(2) |
| Na3 | 17(1) | 16(1) | 18(1) | −3(1) | 5(1) | −2(1) |
| Na4 | 23(1) | 16(1) | 16(1) | −2(1) | 5(1) | −1(1) |
| S201 | 33(1) | 16(1) | 22(1) | −6(1) | 8(1) | −5(1) |
| N201 | 16(1) | 16(1) | 14(1) | 3(1) | 5(1) | 2(1) |
| O201 | 20(1) | 18(1) | 27(1) | 8(1) | −1(1) | 0(1) |
| O202 | 26(1) | 20(1) | 16(1) | −1(1) | 4(1) | 4(1) |
| O203 | 14(1) | 19(1) | 12(1) | −2(1) | 2(1) | 0(1) |
| O204 | 16(1) | 25(1) | 18(1) | −4(1) | 3(1) | 4(1) |
| O205 | 28(1) | 33(1) | 18(1) | −3(1) | 7(1) | −1(1) |
| O206 | 38(2) | 36(2) | 22(1) | 7(1) | 13(1) | 3(1) |
| O207 | 37(2) | 42(2) | 22(1) | −4(1) | 1(1) | −1(1) |
| C201 | 14(2) | 20(2) | 19(2) | 4(1) | 9(1) | 3(1) |
| C202 | 19(2) | 17(2) | 15(2) | −2(1) | 5(1) | 4(1) |
| C203 | 28(2) | 27(2) | 22(2) | 7(1) | 12(2) | 9(2) |
| C204 | 29(2) | 17(2) | 18(2) | −1(1) | 5(1) | 7(2) |
| C205 | 22(2) | 16(2) | 7(1) | 0(1) | 3(1) | −3(1) |
| C206 | 18(2) | 19(2) | 11(1) | 0(1) | 5(1) | −4(1) |
| C207 | 23(2) | 28(2) | 15(2) | −6(1) | 7(1) | −9(2) |
| C208 | 15(2) | 40(2) | 16(2) | 0(2) | 2(1) | −8(2) |
| C209 | 16(2) | 32(2) | 15(2) | 2(1) | 5(1) | 1(2) |
| C210 | 16(2) | 24(2) | 14(1) | 1(1) | 4(1) | −3(2) |
| C211 | 17(2) | 16(2) | 12(1) | 3(1) | 6(1) | −4(1) |
| C212 | 17(2) | 28(2) | 25(2) | 0(1) | 8(1) | 7(2) |
| C213 | 26(2) | 25(2) | 28(2) | 2(1) | 10(2) | 6(2) |
| C214 | 24(2) | 30(2) | 24(2) | −5(1) | 2(1) | 2(2) |
| C215 | 24(2) | 44(2) | 22(2) | −6(1) | 7(2) | −5(2) |
| C216 | 44(2) | 32(2) | 16(2) | −4(1) | 13(2) | −13(2) |
| C217 | 48(2) | 33(2) | 17(2) | −3(2) | 8(2) | −15(2) |
| C218 | 38(2) | 47(3) | 29(2) | 4(2) | 7(2) | −1(2) |
| O1W | 20(1) | 16(1) | 23(1) | −4(1) | −2(1) | 4(1) |
| O2W | 40(2) | 26(1) | 28(1) | −2(1) | 22(1) | −5(1) |
| O3W | 26(1) | 22(1) | 39(2) | 7(1) | −5(1) | −7(1) |
| O4W | 52(2) | 34(2) | 43(2) | 7(1) | 29(2) | 4(1) |

TABLE 6

Hydrogen coordinates [×10⁴] and isotropic displacement parameters [Å² × 10³].

| Atom | x | y | z | $U_{eq}$ | S.o.f. |
|---|---|---|---|---|---|
| H10X | 5554 | 7276 | 9419 | 34 | 1 |
| H10Y | 4712 | 5884 | 9101 | 34 | 1 |
| H10Z | 4936 | 8195 | 8854 | 34 | 1 |
| H10A | 6254 | 2168 | 8860 | 29 | 1 |
| H10B | 5944 | 2926 | 9364 | 29 | 1 |
| H107 | 8669 | 7106 | 9700 | 27 | 1 |
| H108 | 9832 | 9539 | 9791 | 32 | 1 |
| H109 | 9754 | 12340 | 9116 | 27 | 1 |
| H11X | 9658 | 13862 | 8259 | 25 | 1 |
| H11Y | 9249 | 15584 | 8589 | 25 | 1 |
| H11A | 8378 | 17237 | 7781 | 28 | 1 |
| H11B | 9345 | 17289 | 7766 | 28 | 1 |
| H11C | 9356 | 12384 | 7296 | 29 | 1 |
| H11D | 9839 | 14749 | 7305 | 29 | 1 |
| H11E | 8961 | 15192 | 6339 | 30 | 1 |
| H11F | 9689 | 13287 | 6447 | 30 | 1 |
| H11G | 8947 | 10664 | 5714 | 33 | 1 |
| H11H | 8347 | 12838 | 5506 | 33 | 1 |
| H11I | 7126 | 10673 | 5538 | 31 | 1 |
| H11J | 7563 | 9555 | 5126 | 31 | 1 |
| H11K | 6857 | 5952 | 5345 | 51 | 1 |
| H11L | 6582 | 7295 | 5799 | 51 | 1 |
| H11M | 7179 | 5101 | 5959 | 51 | 1 |
| H20X | 4916 | 2597 | 5440 | 37 | 1 |
| H20Y | 5699 | 1084 | 5793 | 37 | 1 |
| H20Z | 5468 | 3404 | 6033 | 37 | 1 |
| H20A | 4509 | −2715 | 5834 | 26 | 1 |
| H20B | 4200 | −1093 | 5312 | 26 | 1 |
| H207 | 1549 | 1167 | 5241 | 26 | 1 |
| H208 | 309 | 3290 | 5179 | 29 | 1 |
| H209 | 338 | 6072 | 5848 | 25 | 1 |
| H21A | 396 | 7737 | 6655 | 28 | 1 |
| H21B | 872 | 9550 | 6387 | 28 | 1 |
| H21C | 1753 | 10555 | 7314 | 31 | 1 |
| H21D | 770 | 11334 | 7160 | 31 | 1 |
| H21N | 943 | 11331 | 8116 | 33 | 1 |
| H21O | 1907 | 10425 | 8248 | 33 | 1 |
| H21E | 1219 | 9555 | 8947 | 36 | 1 |
| H21F | 624 | 7797 | 8525 | 36 | 1 |
| H21G | 1375 | 4659 | 9235 | 36 | 1 |
| H21H | 1836 | 6815 | 9580 | 36 | 1 |
| H21I | 3193 | 5343 | 9518 | 40 | 1 |

TABLE 6-continued

Hydrogen coordinates [×10$^4$] and isotropic displacement parameters [Å$^2$ × 10$^3$].

| Atom | x | y | z | U$_{eq}$ | S.o.f. |
|---|---|---|---|---|---|
| H21J | 2777 | 3825 | 9883 | 40 | 1 |
| H21X | 3916 | 2168 | 9245 | 58 | 1 |
| H21Y | 3385 | −91 | 9023 | 58 | 1 |
| H21Z | 3604 | 586 | 9647 | 58 | 1 |
| H901 | 6242(11) | 16730(60) | 7201(10) | 32 | 1 |
| H902 | 6915(18) | 17270(50) | 7680(9) | 32 | 1 |
| H903 | 7390(20) | 8950(20) | 6978(9) | 43 | 1 |
| H904 | 7735(18) | 10400(60) | 6640(13) | 43 | 1 |
| H905 | 3852(11) | 11330(40) | 7778(11) | 49 | 1 |
| H906 | 3260(20) | 11580(40) | 7261(6) | 49 | 1 |
| H907 | 2405(12) | 5420(60) | 8200(13) | 59 | 1 |
| H908 | 2980(20) | 3810(30) | 8113(17) | 59 | 1 |

TABLE 7

Hydrogen bonds [Å and °].

| D—H...A | d(D—H) | d(H...A) | d(D...A) | ∠ (DHA) |
|---|---|---|---|---|
| O1W—H901...O201$^{iii}$ | 0.848(12) | 1.856(15) | 2.693(3) | 169(4) |
| O1W—H902...O103$^i$ | 0.842(12) | 1.97(2) | 2.762(3) | 156(3) |
| O2W—H903...O1W$^{ii}$ | 0.787(12) | 2.216(18) | 2.913(3) | 148(3) |
| O2W—H904...O106 | 0.864(11) | 1.964(12) | 2.805(3) | 164(3) |
| O2W—H904...O107 | 0.864(11) | 2.57(3) | 3.063(3) | 117(3) |
| O3W—H906...O203$^i$ | 0.874(12) | 1.954(18) | 2.698(3) | 142(3) |
| O4W—H907...O206 | 0.875(12) | 2.16(3) | 2.819(3) | 132(3) |
| O4W—H908...O3W$^{ii}$ | 0.851(13) | 2.25(2) | 3.035(4) | 153(4) |

Symmetry transformations used to generate equivalent atoms:
(i) x, y + 1, z
(ii) x, y − 1, z
(iii) x, y + 2, z

Example 11

Form B Crystal Data and Structural Refinement

Diffractometer: Rigaku AFC12 goniometer equipped with an enhanced sensitivity (HG) Saturn724+ detector mounted at the window of an FR-E+ SuperBright molybdenum rotating anode generator with HF Varimax optics (100 μm focus).

Cell determination, Data collection, Data reduction and cell refinement & Absorption correction: CrystalClear-SM Expert 2.0 r7 (Rigaku, 2011).

Structure solution: SHELXS97 (Sheldrick, G. M. (2008). *Acta Cryst.* A64, 112-122). Structure refinement: SHELXL2012 (G. M. Sheldrick (2012), University of Göttingen, Germany).

Graphics: CrystalMaker: a crystal and molecular structures program for Mac and Windows. CrystalMaker Software Ltd, Oxford, England (www.crystalmaker.com)

Formula weight 940.87
Temperature 100(2) K
Wavelength 0.71073 Å
Crystal system Monoclinic
Space group P2$_1$
Unit cell dimensions a=5.795(3) Å
b=17.155(10) Å β=92.589(8)°
c=43.89(3) Å
Volume 4358(4) Å$^3$
Z 4 (Z'=2)
Density (calculated) 1.434 Mg/m$^3$
Absorption coefficient 0.236 mm$^{-1}$
F(000) 1976
Crystal Lath; Green
Crystal size 0.120×0.080×0.050 mm$^3$
Orange for data collection 3.016-25.026°
Index ranges −6≤h≤6, −20≤k≤20, −52≤l≤52
Reflections collected 47789
Independent reflections 14973 [R$_{int}$=0.0950]
Completeness to θ=25.242° 97.5%
Absorption correction Semi-empirical from equivalents
Max. and min. transmission 0.988 and 0.972
Refinement method Full-matrix least-squares on F$^2$
Data/restraint/parameters 14973/19/1143
Goodness-of-fit on F$^2$ 1.077
Final R indices [F$^2$>2σ(F$^2$)] R1=0.0670, wR2=0.1131
R indices (all data) R1=0.0837, wR2=0.1204
Absolute structure parameter 0.10(6)
Largest diff. peak and hole 0.445 and −0.311 e Å$^{-3}$

TABLE 8

Atomic coordinates [× 10$^4$], equivalent isotropic displacement parameters [Å$^2$ × 10$^3$] and site occupancy factors. U$_{eq}$ is defined as one third of the trace of the orthogonalized Uij tensor.

| Atom | x | y | z | U$_{eq}$ | S.o.f |
|---|---|---|---|---|---|
| Na1 | 4052(4) | 13751(2) | 882(1) | 22(1) | 1 |
| Na2 | 7616(4) | 15409(2) | 1000(1) | 20(1) | 1 |
| Na3 | 11938(4) | 15275(2) | 1584(1) | 20(1) | 1 |
| Na4 | 9705(5) | 17122(2) | 1750(1) | 27(1) | 1 |
| Na5 | 5794(5) | 9003(2) | 4076(1) | 22(1) | 1 |
| Na6 | 2408(4) | 10615(2) | 4013(1) | 19(1) | 1 |
| Na7 | 7880(4) | 10559(2) | 3445(1) | 20(1) | 1 |
| Na8 | 10712(5) | 12377(2) | 3275(1) | 23(1) | 1 |
| S101 | 12416(3) | 15700(1) | 69(1) | 23(1) | 1 |
| O101 | 14736(8) | 16354(3) | 1021(1) | 20(1) | 1 |
| O102 | 11130(8) | 16109(3) | 1164(1) | 20(1) | 1 |
| O103 | 6721(8) | 14417(3) | 623(1) | 19(1) | 1 |
| O104 | 3815(8) | 13444(3) | 336(1) | 22(1) | 1 |
| O105 | 2529(8) | 11985(3) | 612(1) | 21(1) | 1 |
| O106 | 6668(8) | 11240(3) | 847(1) | 26(1) | 1 |
| O107 | 11429(9) | 10733(3) | 1360(1) | 37(1) | 1 |
| N101 | 10090(9) | 15578(3) | 571(1) | 19(1) | 1 |
| C101 | 12626(12) | 16226(4) | 966(2) | 18(2) | 1 |
| C102 | 11717(11) | 16233(4) | 626(2) | 18(2) | 1 |
| C103 | 10369(13) | 16994(4) | 570(2) | 24(2) | 1 |
| C104 | 13715(12) | 16162(5) | 408(2) | 25(2) | 1 |
| C105 | 10199(12) | 15298(4) | 297(2) | 21(2) | 1 |
| C106 | 8620(11) | 14717(4) | 155(2) | 18(2) | 1 |
| C107 | 8803(12) | 14566(4) | −164(2) | 22(2) | 1 |
| C108 | 7269(13) | 14074(4) | −311(2) | 24(2) | 1 |
| C109 | 5580(13) | 13701(4) | −154(2) | 24(2) | 1 |
| C110 | 5430(12) | 13805(4) | 156(2) | 20(2) | 1 |
| C111 | 6943(11) | 14335(4) | 327(2) | 16(2) | 1 |
| C112 | 2258(12) | 12910(4) | 181(2) | 22(2) | 1 |
| C113 | 1028(12) | 12442(4) | 419(2) | 25(2) | 1 |
| C114 | 3756(12) | 11400(4) | 449(2) | 25(2) | 1 |
| C115 | 4880(12) | 10837(4) | 678(2) | 27(2) | 1 |
| C116 | 8150(13) | 10723(4) | 1024(2) | 30(2) | 1 |
| C117 | 9771(12) | 11238(4) | 1214(2) | 27(2) | 1 |
| C118 | 13195(14) | 11168(5) | 1526(2) | 39(2) | 1 |
| S201 | 18440(3) | 14752(1) | 2288(1) | 29(1) | 1 |
| O201 | 18760(8) | 14542(3) | 1464(1) | 19(1) | 1 |
| O202 | 14997(8) | 14590(3) | 1328(1) | 20(1) | 1 |
| O203 | 12378(8) | 16224(3) | 1942(1) | 20(1) | 1 |
| O204 | 9682(9) | 17017(3) | 2298(1) | 29(1) | 1 |
| O205 | 7290(9) | 18145(3) | 1998(1) | 28(1) | 1 |
| O206 | 10967(10) | 18551(4) | 1651(1) | 44(2) | 1 |
| O207 | 15312(10) | 18780(4) | 1092(1) | 48(2) | 1 |
| N201 | 14489(9) | 14651(3) | 1969(1) | 19(1) | 1 |
| C201 | 16656(12) | 14433(4) | 1515(2) | 20(2) | 1 |
| C202 | 16019(12) | 14065(4) | 1829(2) | 20(2) | 1 |
| C203 | 14663(13) | 13307(4) | 1763(2) | 25(2) | 1 |
| C204 | 18159(12) | 13903(4) | 2039(2) | 24(2) | 1 |
| C205 | 15507(12) | 15018(4) | 2194(2) | 20(2) | 1 |
| C206 | 14441(12) | 15616(4) | 2376(2) | 22(2) | 1 |
| C207 | 14921(14) | 15652(4) | 2693(2) | 28(2) | 1 |
| C208 | 13725(14) | 16128(4) | 2880(2) | 28(2) | 1 |
| C209 | 11913(13) | 16596(4) | 2758(2) | 28(2) | 1 |

TABLE 8-continued

Atomic coordinates [× 10⁴], equivalent isotropic displacement parameters [Å² × 10³] and site occupancy factors. $U_{eq}$ is defined as one third of the trace of the orthogonalized $U_{ij}$ tensor.

| Atom | x | y | z | $U_{eq}$ | S.o.f |
|---|---|---|---|---|---|
| C210 | 11461(13) | 16581(4) | 2445(2) | 25(2) | 1 |
| C211 | 12735(12) | 16142(4) | 2242(2) | 22(2) | 1 |
| C212 | 8137(14) | 17447(4) | 2479(2) | 31(2) | 1 |
| C213 | 6322(14) | 17792(5) | 2259(2) | 37(2) | 1 |
| C214 | 8693(15) | 18814(5) | 2071(2) | 40(2) | 1 |
| C215 | 9550(16) | 19127(5) | 1789(2) | 48(2) | 1 |
| C216 | 12360(17) | 18924(6) | 1431(2) | 57(3) | 1 |
| C217 | 13848(16) | 18345(6) | 1300(2) | 49(3) | 1 |
| C218 | 16863(15) | 18253(5) | 953(2) | 40(2) | 1 |
| S301 | −2291(3) | 10845(1) | 4948(1) | 22(1) | 1 |
| O301 | −4621(8) | 11549(3) | 4001(1) | 20(1) | 1 |
| O302 | −983(7) | 11360(3) | 3857(1) | 18(1) | 1 |
| O303 | 3325(7) | 9621(3) | 4369(1) | 18(1) | 1 |
| O304 | 6146(8) | 8568(3) | 4624(1) | 21(1) | 1 |
| O305 | 7261(8) | 7082(3) | 4341(1) | 22(1) | 1 |
| O306 | 3185(9) | 6342(3) | 4118(1) | 28(1) | 1 |
| O307 | 1146(9) | 6963(3) | 3556(1) | 31(1) | 1 |
| N301 | 38(9) | 10791(3) | 4446(1) | 17(1) | 1 |
| C301 | −2469(12) | 11441(4) | 4056(2) | 19(2) | 1 |
| C302 | −1621(11) | 11433(4) | 4400(2) | 19(2) | 1 |
| C303 | −309(13) | 12199(4) | 4462(2) | 24(2) | 1 |
| C304 | −3612(11) | 11328(4) | 4616(1) | 19(2) | 1 |
| C305 | −68(11) | 10478(4) | 4714(2) | 16(2) | 1 |
| C306 | 1505(12) | 9877(4) | 4845(2) | 19(2) | 1 |
| C307 | 1406(12) | 9700(4) | 5157(2) | 22(2) | 1 |
| C308 | 2921(13) | 9188(4) | 5297(2) | 22(2) | 1 |
| C309 | 4586(12) | 8803(4) | 5125(2) | 24(2) | 1 |
| C310 | 4631(12) | 8940(4) | 4815(2) | 18(2) | 1 |
| C311 | 3124(12) | 9497(4) | 4662(2) | 20(2) | 1 |
| C312 | 7748(12) | 8019(4) | 4766(2) | 22(2) | 1 |
| C313 | 8847(12) | 7544(4) | 4520(2) | 22(2) | 1 |
| C314 | 6087(13) | 6500(4) | 4513(2) | 28(2) | 1 |
| C315 | 4944(13) | 5932(4) | 4291(2) | 28(2) | 1 |
| C316 | 2124(14) | 5881(5) | 3879(2) | 35(2) | 1 |
| C317 | 186(13) | 6341(5) | 3728(2) | 34(2) | 1 |
| C318 | −639(14) | 7491(5) | 3440(2) | 37(2) | 1 |
| S401 | 2769(3) | 9872(1) | 2540(1) | 24(1) | 1 |
| O401 | 963(8) | 9753(3) | 3512(1) | 25(1) | 1 |
| O402 | 4702(8) | 9842(3) | 3653(1) | 21(1) | 1 |
| O403 | 8221(7) | 11481(3) | 3052(1) | 19(1) | 1 |
| O404 | 11381(8) | 12233(3) | 2745(1) | 24(1) | 1 |
| O405 | 13239(8) | 13439(3) | 3053(1) | 22(1) | 1 |
| O406 | 9169(8) | 13803(3) | 3360(1) | 25(1) | 1 |
| O407 | 4824(9) | 13971(3) | 3918(1) | 34(1) | 1 |
| N401 | 5370(9) | 10139(3) | 3032(1) | 17(1) | 1 |
| C401 | 3074(12) | 9724(4) | 3457(2) | 20(2) | 1 |
| C402 | 3758(11) | 9534(4) | 3128(2) | 20(2) | 1 |
| C403 | 5063(13) | 8756(4) | 3133(2) | 26(2) | 1 |
| C404 | 1664(12) | 9529(5) | 2894(2) | 27(2) | 1 |
| C405 | 5100(11) | 10342(4) | 2752(2) | 16(2) | 1 |
| C406 | 6612(12) | 10876(4) | 2593(2) | 21(2) | 1 |
| C407 | 6520(13) | 10870(4) | 2267(2) | 26(2) | 1 |
| C408 | 8002(13) | 11310(5) | 2105(2) | 28(2) | 1 |
| C409 | 9684(12) | 11773(4) | 2259(2) | 24(2) | 1 |
| C410 | 9736(12) | 11799(4) | 2574(2) | 19(2) | 1 |
| C411 | 8161(12) | 11381(4) | 2760(2) | 18(2) | 1 |
| C412 | 13020(12) | 12676(4) | 2582(2) | 21(2) | 1 |
| C413 | 14520(12) | 13093(4) | 2822(2) | 24(2) | 1 |
| C414 | 11592(12) | 14007(4) | 2938(2) | 24(2) | 1 |
| C415 | 10503(13) | 14371(4) | 3207(2) | 28(2) | 1 |
| C416 | 7742(14) | 14167(4) | 3574(2) | 29(2) | 1 |
| C417 | 6299(13) | 13555(4) | 3727(2) | 27(2) | 1 |
| C418 | 3246(13) | 13469(5) | 4060(2) | 33(2) | 1 |
| O1W | 6356(9) | 12768(3) | 1074(2) | 29(1) | 1 |
| O2W | 210(8) | 13761(3) | 964(1) | 24(1) | 1 |
| O3W | 6360(9) | 16513(3) | 1614(1) | 31(1) | 1 |
| O4W | 4709(10) | 7867(3) | 3863(1) | 35(1) | 1 |
| O5W | 9631(8) | 9009(3) | 4032(1) | 26(1) | 1 |
| O6W | 14070(8) | 11773(3) | 3403(1) | 26(1) | 1 |

TABLE 9

Bond lengths [Å] and angles [°].

| | | | |
|---|---|---|---|
| Na1—O103 | 2.268(5) | Na6—O303 | 2.356(5) |
| Na1—O2W | 2.272(6) | Na6—N301 | 2.414(6) |
| Na1—O1W | 2.288(6) | Na6—O302 | 2.417(5) |
| Na1—O104 | 2.452(5) | Na6—O402 | 2.492(5) |
| Na1—O202$^i$ | 2.470(5) | Na6—O401 | 2.748(6) |
| Na2—O101$^i$ | 2.332(5) | Na6—C401 | 2.918(7) |
| Na2—O103 | 2.412(6) | Na7—O401$^{ii}$ | 2.268(6) |
| Na2—N101 | 2.435(6) | Na7—O302$^{ii}$ | 2.343(5) |
| Na2—O102 | 2.445(5) | Na1—O403 | 2.354(5) |
| Na2—O202$^i$ | 2.558(5) | Na1—N401 | 2.381(6) |
| Na2—O201$^i$ | 2.583(5) | Na1—O402 | 2.426(5) |
| Na2—C201$^i$ | 2.887(8) | Na7—C301$^{ii}$ | 3.096(8) |
| Na3—O203 | 2.271(5) | Na1—Na6$^{ii}$ | 3.539(4) |
| Na3—O201$^i$ | 2.272(5) | Na7—Na8 | 3.618(4) |
| Na3—O102 | 2.362(5) | Na8—O6W | 2.253(6) |
| Na3—O202 | 2.443(5) | Na8—O403 | 2.297(5) |
| Na3—N201 | 2.444(6) | Na8—O404 | 2.390(6) |
| Na3—C201 | 3.119(8) | Na8—O405 | 2.558(6) |
| Na3—Na4 | 3.511(4) | Na8—O406 | 2.636(6) |
| Na4—O3W | 2.258(6) | S101—C105 | 1.801(7) |
| Na4—O203 | 2.316(6) | S101—C104 | 1.815(7) |
| Na4—O204 | 2.410(6) | O101—C101 | 1.254(8) |
| Na4—O205 | 2.522(6) | O101—Na2$^{ii}$ | 2.332(5) |
| Na4—O206 | 2.601(7) | O102—C101 | 1.269(8) |
| Na5—O303 | 2.234(5) | O103—C111 | 1.318(7) |
| Na5—O4W | 2.240(6) | O104—C110 | 1.395(8) |
| Na5—O5W | 2.241(6) | O104—C112 | 1.434(8) |
| Na5—O402 | 2.414(5) | O105—C113 | 1.423(8) |
| Na5—O304 | 2.516(5) | O105—C114 | 1.439(8) |
| Na5—Na6 | 3.395(4) | O106—C115 | 1.427(8) |
| Na6—O301$^{ii}$ | 2.355(5) | O106—C116 | 1.435(8) |
| O107—C117 | 1.424(8) | C208—C209 | 1.409(11) |
| O107—C118 | 1.439(9) | C209—C210 | 1.386(10) |
| N101—C105 | 1.296(8) | C210—C211 | 1.403(10) |
| N101—C102 | 1.480(9) | C212—C213 | 1.516(11) |
| C101—C102 | 1.560(9) | C214—C215 | 1.458(11) |
| C102—C103 | 1.536(9) | C216—C217 | 1.450(12) |
| C102—C104 | 1.542(9) | S301—C305 | 1.795(7) |
| C105—C106 | 1.473(10) | S301—C304 | 1.814(7) |
| C106—C111 | 1.420(8) | O301—C301 | 1.273(8) |
| C106—C107 | 1.430(9) | O301—Na6$^i$ | 2.355(5) |
| C107—C108 | 1.367(10) | O302—C301 | 1.263(8) |
| C108—C109 | 1.382(9) | O302—Na7$^i$ | 2.343(5) |
| C109—C110 | 1.378(9) | O303—C311 | 1.312(8) |
| C110—C111 | 1.448(9) | O304—C310 | 1.396(8) |
| C112—C113 | 1.520(10) | O304—C312 | 1.444(8) |
| C114—C115 | 1.520(10) | O305—C313 | 1.423(8) |
| C116—C117 | 1.514(10) | O305—C314 | 1.440(8) |
| S201—C205 | 1.790(7) | O306—C315 | 1.427(8) |
| S201—C204 | 1.823(8) | O306—C316 | 1.431(9) |
| O201—C201 | 1.263(8) | O307—C317 | 1.433(9) |
| O201—Na3$^{ii}$ | 2.272(5) | O307—C318 | 1.449(9) |
| O201—Na2$^{ii}$ | 2.583(5) | N301—C305 | 1.297(8) |
| O202—C201 | 1.265(8) | N301—C302 | 1.470(8) |
| O202—Na1$^{ii}$ | 2.470(5) | C301—C302 | 1.563(9) |
| O202—Na2$^{ii}$ | 2.558(5) | C301—Na7$^i$ | 3.096(7) |
| O203—C211 | 1.327(8) | C302—C303 | 1.537(10) |
| O204—C210 | 1.406(9) | C302—C304 | 1.538(10) |
| O204—C212 | 1.429(8) | C305—C306 | 1.476(9) |
| O205—C213 | 1.430(9) | C306—C307 | 1.406(9) |
| O205—C214 | 1.434(9) | C306—C311 | 1.423(9) |
| O206—C215 | 1.437(10) | C307—C308 | 1.368(10) |
| O206—C216 | 1.437(10) | C308—C309 | 1.415(9) |
| O207—C218 | 1.432(10) | C309—C310 | 1.382(9) |
| O207—C217 | 1.475(9) | C310—C311 | 1.442(9) |
| N201—C205 | 1.289(9) | C312—C313 | 1.515(9) |
| N201—C202 | 1.492(9) | C314—C315 | 1.508(10) |
| C201—C202 | 1.574(9) | C316—C317 | 1.503(10) |
| C201—Na2$^{ii}$ | 2.887(9) | S401—C405 | 1.795(7) |
| C202—C204 | 1.537(9) | S401—C404 | 1.804(7) |
| C202—C203 | 1.540(10) | O401—C401 | 1.258(8) |
| C205—C206 | 1.454(10) | O401—Na7$^i$ | 2.268(6) |
| C206—C207 | 1.411(9) | O402—C401 | 1.262(8) |
| C206—C211 | 1.445(10) | O403—C411 | 1.291(8) |
| C207—C208 | 1.368(10) | O404—C410 | 1.401(8) |
| O404—C412 | 1.434(8) | C402—C404 | 1.554(10) |
| O405—C413 | 1.413(8) | C405—C406 | 1.467(9) |
| O405—C414 | 1.439(8) | C406—C407 | 1.427(9) |

TABLE 9-continued

Bond lengths [Å] and angles [°].

| | | | | | |
|---|---|---|---|---|---|
| O406—C416 | 1.424(8) | C406—C411 | 1.428(9) | O5W—Na5—O304 | 92.67(19) | O302—Na6—Na7$^i$ | 41.18(12) |
| O406—C415 | 1.429(8) | C407—C408 | 1.368(10) | O402—Na5—O304 | 156.9(2) | O402—Na6—Na7$^i$ | 86.45(14) |
| O407—C417 | 1.417(8) | C408—C409 | 1.406(10) | O303—Na5—Na6 | 43.71(13) | O401—Na6—Na7$^i$ | 39.85(12) |
| O407—C418 | 1.421(9) | C409—C410 | 1.380(9) | O4W—Na5—Na6 | 121.61(19) | C401—Na6—Na7$^i$ | 61.24(16) |
| N401—C405 | 1.282(8) | C410—C411 | 1.444(9) | O5W—Na5—Na6 | 124.14(18) | Na5—Na6—Na7$^i$ | 116.29(10) |
| N401—C402 | 1.469(8) | C412—C413 | 1.516(10) | O402—Na5—Na6 | 47.18(13) | O301$^{ii}$—Na6—Na7 | 54.46(13) |
| C401—C402 | 1.551(9) | C414—C415 | 1.500(10) | O303—Na6—Na7 | 103.16(14) | O401$^{ii}$—Na7-Na6 | 123.92(15) |
| C402—C403 | 1.534(10) | C416—C417 | 1.517(10) | N301—Na6—Na7 | 163.70(17) | O302$^{ii}$—Na7—Na6 | 73.53(13) |
| O103—Na1—O2W | 140.4(2) | N101—Na2—C201$^i$ | 144.6(2) | O302—Na6—Na7 | 118.58(14) | O403—Na7—Na6 | 121.28(15) |
| O103—Na1—O1W | 99.0(2) | O102—Na2—C201$^i$ | 104.0(2) | O402—Na6—Na7 | 32.55(12) | N401—Na7—Na6 | 90.38(16) |
| O2W—Na1—O1W | 120.5(2) | O202$^i$—Na2—C201$^i$ | 25.99(17) | O401—Na6—Na7 | 73.65(12) | O402—Na7—Na6 | 33.55(12) |
| O103—Na1—O104 | 68.19(17) | O201$^i$—Na2—C201$^i$ | 25.95(16) | C401—Na6—Na7 | 49.30(15) | C301$^{ii}$—Na7—Na6 | 51.83(14) |
| O2W—Na1—O104 | 98.36(19) | O101$^i$—Na2—Na3 | 120.31(15) | Na5—Na6—Na7 | 64.72(7) | Na6$^{ii}$—Na7—Na6 | 97.99(9) |
| O1W—Na1—O104 | 102.0(2) | O103—Na2—Na3 | 125.36(15) | Na7$^i$—Na6—Na7 | 97.99(9) | Na8—Na7—Na6 | 118.21(9) |
| O103—Na1—O202$^i$ | 88.32(18) | N101—Na2—Na3 | 98.44(16) | O401$^{ii}$—Na7—O302$^{ii}$ | 93.69(19) | Na5—Na7—Na6 | 48.95(6) |
| O2W—Na1—O202$^i$ | 93.04(19) | O102—Na2—Na3 | 42.20(12) | O401$^{ii}$—Na7—O403 | 114.44(19) | O6W—Na8—O403 | 108.5(2) |
| O1W—Na1—O202$^i$ | 91.85(19) | O202$^i$—Na2—Na3 | 88.61(14) | O302$^{ii}$—Na7—O403 | 98.07(19) | O6W—Na8—O404 | 91.0(2) |
| O104—Na1—O202$^i$ | 154.1(2) | O201$^i$—Na2—Na3 | 40.33(12) | O401$^{ii}$—Na7—N401 | 111.4(2) | O403—Na8—O404 | 69.03(17) |
| O103—Na1—Na2 | 42.40(13) | C201$^i$—Na2—Na3 | 63.06(16) | O302$^{ii}$—Na7—N401 | 154.8(2) | O6W—Na8—O405 | 85.4(2) |
| O2W—Na1—Na2 | 122.68(17) | O101$^i$—Na2—Na1 | 98.67(15) | O403—Na7—N401 | 73.50(19) | O403—Na8—O405 | 132.32(19) |
| O1W—Na1—Na2 | 102.18(17) | O103—Na2—Na1 | 39.37(12) | O401$^{ii}$—Na7—O402 | 104.4(2) | O404—Na8—O405 | 65.22(17) |
| O104—Na1—Na2 | 108.78(14) | N101—Na2—Na1 | 110.03(17) | O302$^{ii}$—Na7—O402 | 101.45(18) | O6W—Na8—O406 | 133.4(2) |
| O202$^i$—Na1—Na2 | 46.27(12) | O102—Na2—Na1 | 155.62(19) | O403—Na7—O402 | 134.91(19) | O403—Na8—O406 | 118.04(19) |
| O101$^i$—Na2—O103 | 112.69(19) | O202$^i$—Na2—Na1 | 44.25(12) | N401—Na7—O402 | 71.63(18) | O404—Na8—O406 | 107.71(19) |
| O101$^i$—Na2—N101 | 113.3(2) | O201$^i$—Na2—Na1 | 77.28(13) | O401$^{ii}$—Na7—C301$^{ii}$ | 105.5(2) | O405—Na8—O406 | 66.25(17) |
| O103—Na2—N101 | 70.73(19) | C201$^i$—Na2—Na1 | 61.10(16) | O302$^{ii}$—Na7—C301$^{ii}$ | 21.70(17) | O6W—Na8—Na7 | 86.94(17) |
| O101$^i$—Na2—O102 | 103.56(19) | Na3—Na2—Na1 | 116.55(10) | O403—Na7—C301$^{ii}$ | 108.5(2) | O403—Na8—Na7 | 39.51(13) |
| O103—Na2—O102 | 134.36(19) | O203—Na3—O201$^i$ | 128.4(2) | N401—Na7—C301$^{ii}$ | 138.2(2) | O404—Na8—Na7 | 101.90(15) |
| N101—Na2—O102 | 69.99(19) | O203—Na3—O102 | 96.8(2) | O402—Na7—C301$^{ii}$ | 80.84(19) | O405—Na8—Na7 | 164.83(15) |
| O101$^i$—Na2—O202$^i$ | 85.15(18) | O201$^i$—Na3—O102 | 91.42(19) | O401$^{ii}$—Na7—Na6$^{ii}$ | 50.94(14) | O406—Na8—Na7 | 127.66(15) |
| O103—Na2—O202$^i$ | 83.29(17) | O203—Na3—O202 | 127.1(2) | O302$^{ii}$—Na7—Na6$^{ii}$ | 42.79(12) | C105—S101—C104 | 89.6(3) |
| N101—Na2—O202$^i$ | 152.3(2) | O201$^i$—Na3—O202 | 102.96(19) | O403—Na7—Na6$^{ii}$ | 114.42(15) | C101—O101—Na2$^{ii}$ | 124.3(4) |
| O102—Na2—O202$^i$ | 127.71(18) | O102—Na3—O202 | 93.19(18) | N401—Na7—Na6$^{ii}$ | 162.12(17) | C101—O102—Na3 | 120.7(4) |
| O101$^i$—Na2—O201$^i$ | 121.83(18) | O203—Na3—N201 | 77.8(2) | O402—Na7—Na6$^{ii}$ | 107.44(14) | C101—O102—Na2 | 117.5(4) |
| O103—Na2—O201$^i$ | 99.99(18) | O201$^i$—Na3—N201 | 112.1(2) | C301$^{ii}$—Na7—Na6$^{ii}$ | 56.71(14) | Na3—O102—Na2 | 93.74(19) |
| N101—Na2—O201$^i$ | 122.6(2) | O102—Na3—N201 | 153.9(2) | O401$^{ii}$—Na7—Na8 | 100.98(16) | C111—O103—Na1 | 122.5(4) |
| O102—Na2—O201$^i$ | 82.53(17) | O202—Na3—N201 | 71.27(18) | O302$^{ii}$—Na7—Na8 | 62.50(14) | C111—O103—Na2 | 136.3(4) |
| O202$^i$—Na2—O201$^i$ | 51.57(15) | O203—Na3—C201 | 109.1(2) | O403—Na7—Na8 | 38.37(12) | Na1—O103—Na2 | 98.23(18) |
| O101$^i$—Na2—C201$^i$ | 102.0(2) | O201$^i$—Na3—C201 | 115.2(2) | N401—Na7—Na8 | 111.83(16) | C110—O104—C112 | 116.2(5) |
| O103—Na2—C201$^i$ | 94.8(2) | O102—Na3—C201 | 110.4(2) | O402—Na7—Na8 | 150.82(15) | C110—O104—Na1 | 116.5(4) |
| O202—Na3—C201 | 22.34(16) | O304—Na5—Na6 | 109.93(14) | C301$^{ii}$—Na7—Na8 | 78.74(16) | C112—O104—Na1 | 127.2(4) |
| N201—Na3—C201 | 50.09(19) | O303—Na5—Na7 | 107.32(16) | Na6$^{ii}$—Na7—Na8 | 78.04(8) | C113—O105—C114 | 113.0(5) |
| O203—Na3—Na2 | 120.90(16) | O4W—Na5—Na7 | 111.83(17) | O401$^{ii}$—Na7—Na5 | 76.57(14) | C115—O106—C116 | 112.6(5) |
| O201$^i$—Na3—Na2 | 47.36(15) | O5W—Na5—Na7 | 67.13(15) | O302$^{ii}$—Na7—Na5 | 86.62(15) | C117—O107—C118 | 115.6(6) |
| O102—Na3—Na2 | 44.06(13) | O402—Na5—Na7 | 32.84(12) | O403—Na7—Na5 | 167.52(15) | C105—N101—C102 | 112.1(6) |
| O202—Na3—Na2 | 101.80(14) | O304—Na5—Na7 | 146.19(16) | N401—Na7—Na5 | 97.41(16) | C105—N101—Na2 | 136.6(5) |
| N201—Na3—Na2 | 157.51(18) | Na6—Na5—Na7 | 66.33(8) | O402—Na7—Na5 | 32.64(12) | C102—N101—Na2 | 110.8(4) |
| C201—Na3—Na2 | 124.03(16) | O301$^{ii}$—Na6—O303 | 111.39(19) | C301$^{ii}$—Na7—Na5 | 72.37(15) | O101—C101—O102 | 125.9(6) |
| O203—Na3—Na4 | 40.52(13) | O301$^{ii}$—Na6—N301 | 112.1(2) | Na6$^{ii}$—Na7—Na5 | 76.79(8) | O101—C101—C102 | 117.8(6) |
| O201$^i$—Na3—Na4 | 104.19(16) | O303—Na6—N301 | 71.82(18) | Na8—Na7—Na5 | 148.96(9) | O102—C101—C102 | 116.3(6) |
| O102—Na3—Na4 | 63.51(14) | O301$^{ii}$—Na6—O302 | 102.65(19) | N101—C102—C103 | 107.7(5) | C213—O205—C214 | 113.6(6) |
| O202—Na3—Na4 | 144.30(16) | 303—Na6—O302 | 136.60(19) | N101—C102—C104 | 109.1(6) | C213—O205—Na4 | 107.2(4) |
| N201—Na3—Na4 | 117.92(16) | N301—Na6—O302 | 70.89(18) | C103—C102—C104 | 110.9(6) | C214—O205—Na4 | 109.5(4) |
| C201—Na3—Na4 | 140.45(16) | O301$^{ii}$—Na6—O402 | 86.31(18) | N101—C102—C101 | 109.7(5) | C215—O206—C216 | 109.0(7) |
| Na2—Na3—Na4 | 80.54(9) | O303—Na6—O402 | 85.72(17) | C103—C102—C101 | 107.9(6) | C215—O206—Na4 | 114.1(5) |
| O3W—Na4—O203 | 109.9(2) | N301—Na6—O402 | 154.8(2) | C104—C102—C101 | 111.4(6) | C216—O206—Na4 | 134.7(6) |
| O3W—Na4—O204 | 100.8(2) | O302—Na6—O402 | 123.46(18) | C102—C104—S101 | 104.4(5) | C218—O207—C217 | 109.6(6) |
| O203—Na4—O204 | 67.74(18) | O301$^{ii}$—Na6—O401 | 122.98(18) | N101—C105—C106 | 126.1(6) | C205—N201—C202 | 112.6(6) |
| O3W—Na4—O205 | 87.1(2) | O303—Na6—O401 | 101.10(19) | N101—C105—S101 | 116.0(5) | C205—N201—Na3 | 123.8(5) |
| O203—Na4—O205 | 132.9(2) | N301—Na6—O401 | 122.3(2) | C106—C105—S101 | 117.9(5) | C202—N201—Na3 | 111.1(4) |
| O204—Na4—O205 | 66.01(18) | O302—Na6—O401 | 81.01(17) | C111—C106—C107 | 121.4(6) | O201—C201—O202 | 124.3(6) |
| O3W—Na4—O206 | 129.5(2) | O402—Na6—O401 | 50.10(15) | C111—C106—C105 | 120.8(6) | O201—C201—C202 | 118.6(6) |
| O203—Na4—O206 | 119.9(2) | O301$^{ii}$—Na6—C401 | 102.3(2) | C107—C106—C105 | 117.8(6) | O202—C201—C202 | 116.9(6) |
| O204—Na4—O206 | 104.6(2) | O303—Na6—C401 | 98.1(2) | C108—C107—C106 | 119.9(6) | O201—C201—Na2$^{ii}$ | 63.5(4) |
| O205—Na4—O206 | 65.31(19) | N301—Na6—C401 | 145.6(2) | C107—C108—C109 | 120.6(7) | O202—C201—Na2$^{ii}$ | 62.3(4) |
| O3W—Na4—Na3 | 81.24(18) | O302—Na6—C401 | 100.19(19) | C110—C109—C108 | 120.8(7) | C202—C201—Na2$^{ii}$ | 168.1(5) |
| O203—Na4—Na3 | 39.58(13) | O402—Na6—C401 | 25.45(16) | C109—C110—O104 | 124.9(6) | O201—C201—Na3 | 143.7(5) |
| O204—Na4—Na3 | 99.17(15) | O401—Na6—C401 | 25.43(16) | C109—C110—C111 | 121.9(6) | O202—C201—Na3 | 47.2(3) |
| O205—Na4—Na3 | 159.17(18) | O301$^{ii}$—Na6—Na5 | 97.81(15) | O104—C110—C111 | 113.1(6) | C202—C201—Na3 | 81.9(4) |
| O206—Na4—Na3 | 134.92(17) | O303—Na6—Na5 | 40.93(12) | O103—C111—C106 | 125.1(6) | Na2$^{ii}$—C201—Na3 | 90.4(2) |
| O303—Na5—O4W | 118.6(2) | N301—Na6—Na5 | 112.65(16) | O103—C111—C110 | 119.6(6) | N201—C202—C204 | 110.6(6) |
| O303—Na5—O5W | 135.4(2) | O302—Na6—Na5 | 156.00(16) | C106—C111—C110 | 115.2(6) | N201—C202—C203 | 109.8(6) |
| O4W—Na5—O5W | 103.2(2) | O402—Na6—Na5 | 45.26(12) | O104—C112—C113 | 108.5(6) | C204—C202—C203 | 110.5(6) |
| O303—Na5—O402 | 90.38(19) | O401—Na6—Na5 | 77.36(13) | O105—C113—C112 | 114.1(6) | N201—C202—C201 | 105(5) |
| O4W—Na5—O402 | 97.9(2) | C401—Na6—Na5 | 62.86(15) | O105—C114—C115 | 108.7(6) | C204—C202—C201 | 112.5(6) |
| O5W—Na5—O402 | 99.03(19) | O301$^{ii}$—Na6—Na7$^i$ | 121.45(15) | O106—C115—C114 | 108.4(6) | C203—C202—C201 | 108.3(6) |
| O303—Na5—O304 | 67.52(17) | O303—Na6—Na7$^i$ | 125.83(16) | O106—C116—C117 | 106.2(6) | C202—C204—S201 | 105.2(5) |
| O4W—Na5—O304 | 98.7(2) | N301—Na6—Na7$^i$ | 97.36(16) | O107—C117—C116 | 106.5(6) | N201—C205—C206 | 124.9(6) |

TABLE 9-continued

Bond lengths [Å] and angles [°].

| | | | | |
|---|---|---|---|---|
| C205—S201—C204 | 90.4(3) | N201—C205—S201 | 116.6(5) |
| C201—O201—Na3[ii] | 145.0(4) | C206—C205—S201 | 118.4(5) |
| C201—O201—Na2[ii] | 90.6(4) | C207—C206—C211 | 118.4(7) |
| Na3[ii]—O201—Na2[ii] | 92.30(18) | C207—C206—C205 | 120.3(7) |
| C201—O202—Na3 | 110.5(4) | C211—C206—C205 | 121.1(6) |
| C201—O202—Na1[ii] | 121.7(4) | C208—C207—C206 | 122.4(7) |
| Na3—O202—Na1[ii] | 120.3(2) | C210—C209—C208 | 120.1(7) |
| C201—O202—Na2[ii] | 91.7(4) | C210—C209—C208 | 118.1(7) |
| Na3—O202—Na2[ii] | 117.1(2) | C209—C210—C211 | 124.0(7) |
| Na1[ii]—O202—Na2[ii] | 89.48(17) | C209—C210—O204 | 123.1(6) |
| C211—O203—Na3 | 128.2(4) | C211—C210—O204 | 112.9(6) |
| C211—O203—Na4 | 120.2(4) | O203—C211—C210 | 120.6(7) |
| Na3—O203—Na4 | 99.9(2) | O203—C211—C206 | 122.8(6) |
| C210—O204—C212 | 118.9(6) | C210—C211—C206 | 116.6(6) |
| C210—O204—Na4 | 117.4(4) | O204—C212—C213 | 106.3(6) |
| C212—O204—Na4 | 123.2(5) | O205—C213—C212 | 112.9(7) |
| O205—C214—C215 | 108.5(7) | C309—C310—C311 | 122.3(6) |
| O206—C215—C214 | 109.1(7) | O304—C310—C311 | 113.9(6) |
| O206—C216—C217 | 108.8(8) | O303—C311—C306 | 124.7(6) |
| C216—C217—O207 | 105.5(7) | O303—C311—C310 | 119.1(6) |
| C305—S301—C304 | 89.4(3) | C306—C311—C310 | 116.1(6) |
| C301—O301—Na6[i] | 127.4(4) | O304—C312—C313 | 109.1(5) |
| C301—O302—Na7[i] | 115.0(4) | O305—C313—C312 | 114.3(6) |
| C301—O302—Na6 | 115.6(4) | O305—C314—C315 | 108.3(6) |
| Na7[i]—O302—Na6 | 96.02(19) | O306—C315—C314 | 107.9(6) |
| C311—O303—Na5 | 125.0(4) | O306—C316—C317 | 108.8(6) |
| C311—O303—Na6 | 137.6(4) | O307—C317—C316 | 108.9(6) |
| Na5—O303—Na6 | 95.37(18) | C405—S401—C404 | 89.4(3) |
| C310—O304—C312 | 116.6(5) | C401—O401—Na7[i] | 140.0(5) |
| C310—O304—Na5 | 114.4(4) | C401—O401—Na6 | 84.9(4) |
| C312—O304—Na5 | 128.9(4) | Na7[i]—O401—Na6 | 89.21(19) |
| C313—O305—C314 | 113.9(5) | C401—O402—Na5 | 126.1(5) |
| C315—O306—C316 | 113.0(5) | C401—O402—Na7 | 112.5(4) |
| C317—O307—C318 | 111.2(6) | Na5—O402—Na7 | 114.5(2) |
| C305—N301—C302 | 112.3(5) | C401—O402—Na6 | 96.5(4) |
| C305—N301—Na6 | 135.6(5) | Na5—O402—Na6 | 87.57(17) |
| C302—N301—Na6 | 112.1(4) | Na7—O402—Na6 | 113.9(2) |
| O302—C301—O301 | 125.1(6) | C411—O403—Na8 | 120.0(4) |
| O302—C301—C302 | 118.2(6) | C411—O403—Na7 | 129.6(4) |
| O301—C301—C302 | 116.7(6) | Na8—O403—Na7 | 102.11(19) |
| O302—C301—Na7[i] | 43.3(3) | C410—O404—C412 | 117.7(5) |
| O301—C301—Na7[i] | 90.4(4) | C410—O404—Na8 | 116.2(4) |
| C302—C301—Na7[i] | 143.2(4) | C412—O404—Na8 | 124.9(4) |
| N301—C302—C303 | 107.5(5) | C413—O405—C414 | 113.3(5) |
| N301—C302—C304 | 109.3(6) | C413—O405—Na8 | 107.7(4) |
| C303—C302—C304 | 111.6(6) | C414—O405—Na8 | 103.5(4) |
| N301—C302—C301 | 108.4(5) | C416—O406—C415 | 110.6(5) |
| C303—C302—C301 | 107.3(6) | C416—O406—Na8 | 135.3(4) |
| C304—C302—C301 | 112.6(6) | C415—O406—Na8 | 111.9(4) |
| C302—C304—S301 | 104.4(5) | C417—O407—C418 | 111.9(6) |
| N301—C305—C306 | 126.1(6) | C405—N401—C402 | 114.4(6) |
| N301—C305—S301 | 115.9(5) | C405—N401—Na7 | 133.7(5) |
| C306—C305—S301 | 118.0(5) | C402—N401—Na7 | 111.8(4) |
| C307—C306—C311 | 120.6(6) | O401—C401—O402 | 124.5(6) |
| C307—C306—C305 | 118.6(6) | O401—C401—O402 | 118.6(6) |
| C311—C306—C305 | 120.7(6) | O402—C401—O402 | 116.9(6) |
| C308—C307—C306 | 121.5(7) | O401—C401—Na6 | 69.7(4) |
| C307—C308—C309 | 120.0(6) | O402—C401—Na6 | 58.1(3) |
| C310—C309—C308 | 119.3(7) | C402—C401—Na6 | 159.7(5) |
| C309—C310—O304 | 123.7(6) | N401—C402—C403 | 107.4(5) |
| N401—C402—C401 | 108.1(5) | | |
| C403—C402—C401 | 108.4(6) | | |
| N401—C402—C404 | 107.6(6) | | |
| C403—C402—C404 | 112.0(6) | | |
| C401—C402—C404 | 113.1(6) | | |
| C402—C404—S401 | 105.6(5) | | |
| N401—C405—C406 | 125.3(6) | | |
| N401—C405—S401 | 115.6(5) | | |
| C406—C405—S401 | 119.0(5) | | |
| C407—C406—C411 | 121.0(6) | | |
| C407—C406—C405 | 118.4(6) | | |
| C411—C406—C405 | 120.6(6) | | |
| C408—C407—C406 | 121.4(7) | | |
| C407—C408—C409 | 120.0(7) | | |
| C410—C409—C408 | 118.8(6) | | |
| C409—C410—O404 | 122.5(6) | | |
| C409—C410—C411 | 124.4(7) | | |
| O404—C410—C411 | 113.1(6) | | |
| O403—C411—C406 | 125.5(6) | | |
| O403—C411—C410 | 120.5(6) | | |
| C406—C411—C410 | 114.1(6) | | |
| O404—C412—C413 | 105.9(6) | | |
| O405—C413—C412 | 113.2(6) | | |
| O405—C414—C415 | 107.6(6) | | |
| O406—C415—C414 | 109.9(6) | | |
| O406—C416—C417 | 109.7(6) | | |
| O407—C417—C416 | 105.9(6) | | |

Symmetry transformations used to generate equivalent atoms:
(i) x − 1, y, z
(ii) x + 1, y, z

TABLE 10

Anisotropic displacement parameters [Å$^2$ × 10$^3$].
The anisotropic displacement factor exponent takes the form: $-2\pi^2[h^2 a^{*2} U^{11} + \ldots + 2 h k a^* b^* U^{12}]$.

| Atom | U$^{11}$ | U$^{22}$ | U$^{33}$ | U$^{23}$ | U$^{13}$ | U$^{12}$ |
|---|---|---|---|---|---|---|
| Na1 | 14(2) | 32(2) | 20(2) | 2(1) | 1(1) | −2(1) |
| Na2 | 14(2) | 26(2) | 18(2) | 0(1) | 0(1) | −1(1) |
| Na3 | 16(2) | 26(2) | 18(2) | −1(1) | 0(1) | −1(1) |
| Na4 | 20(2) | 31(2) | 29(2) | 3(1) | 0(1) | 3(1) |
| Na5 | 16(2) | 28(2) | 21(2) | −1(1) | 1(1) | 3(1) |
| Na6 | 18(2) | 22(2) | 16(1) | 0(1) | 0(1) | 3(1) |
| Na7 | 17(2) | 26(2) | 17(1) | 1(1) | −2(1) | 0(1) |
| Na8 | 18(2) | 27(2) | 25(2) | 0(1) | −3(1) | 0(1) |
| S101 | 18(1) | 35(1) | 16(1) | 4(1) | 2(1) | −4(1) |
| O101 | 14(3) | 27(3) | 18(3) | 1(2) | 0(2) | −4(2) |
| O102 | 16(3) | 30(3) | 15(3) | 3(2) | −1(2) | −1(2) |
| O103 | 20(3) | 25(3) | 11(3) | −2(2) | 0(2) | −5(2) |
| O104 | 15(3) | 28(3) | 21(3) | −5(2) | −1(2) | −7(2) |
| O105 | 18(3) | 26(3) | 18(3) | −3(2) | 3(2) | −2(2) |
| O106 | 22(3) | 28(3) | 27(3) | 2(2) | −4(2) | −2(2) |
| O107 | 35(3) | 36(3) | 40(3) | 7(3) | −10(3) | −5(3) |
| N101 | 15(3) | 23(3) | 20(3) | 1(3) | −1(2) | 1(3) |
| C101 | 14(4) | 17(4) | 23(4) | 3(3) | 2(3) | 1(3) |
| C102 | 15(4) | 23(4) | 17(4) | 3(3) | −3(3) | −1(3) |
| C103 | 29(4) | 21(4) | 22(4) | 1(3) | −1(3) | 0(3) |
| C104 | 18(4) | 37(5) | 19(4) | 3(3) | −2(3) | −7(3) |
| C105 | 20(4) | 25(4) | 18(4) | 9(3) | −1(3) | −1(3) |
| C106 | 15(4) | 21(4) | 19(4) | 7(3) | 1(3) | 4(3) |
| C107 | 20(4) | 27(4) | 20(4) | 5(3) | 4(3) | −4(3) |
| C108 | 30(5) | 28(4) | 14(4) | 4(3) | 6(3) | −1(4) |
| C109 | 28(4) | 23(4) | 21(4) | 0(3) | −1(3) | −2(3) |
| C110 | 19(4) | 24(4) | 17(4) | 2(3) | 2(3) | −5(3) |
| C111 | 14(4) | 17(4) | 18(4) | 1(3) | −2(3) | 1(3) |
| C112 | 22(4) | 25(4) | 17(4) | −6(3) | −9(3) | −3(3) |
| C113 | 19(4) | 27(4) | 28(4) | −8(3) | −1(3) | −2(3) |
| C114 | 24(4) | 30(4) | 21(4) | −2(3) | 0(3) | 4(4) |
| C115 | 21(4) | 28(4) | 31(4) | −8(4) | 0(3) | 2(4) |
| C116 | 29(5) | 24(4) | 36(5) | 0(4) | −2(4) | 1(4) |
| C117 | 27(4) | 30(4) | 24(4) | 4(3) | 1(3) | 0(4) |
| C118 | 35(5) | 47(6) | 34(5) | −2(4) | −4(4) | −7(4) |
| S201 | 19(1) | 31(1) | 36(1) | 2(1) | −8(1) | 2(1) |
| O201 | 16(3) | 25(3) | 17(3) | −4(2) | 1(2) | −3(2) |
| O202 | 19(3) | 26(3) | 16(3) | 2(2) | −2(2) | 2(2) |
| O203 | 18(3) | 29(3) | 14(3) | −2(2) | 1(2) | 0(2) |
| O204 | 34(3) | 28(3) | 26(3) | −5(2) | 14(2) | 5(3) |
| O205 | 20(3) | 25(3) | 39(3) | −5(2) | 2(2) | −4(2) |
| O206 | 35(4) | 53(4) | 46(4) | 19(3) | 12(3) | 2(3) |
| O207 | 46(4) | 58(4) | 41(4) | 7(3) | 16(3) | 15(3) |
| N201 | 18(3) | 25(3) | 15(3) | −1(3) | 2(2) | 1(3) |
| C201 | 18(4) | 19(4) | 24(4) | −3(3) | 4(3) | −1(3) |
| C202 | 19(4) | 24(4) | 18(4) | 2(3) | 2(3) | 2(3) |
| C203 | 26(5) | 24(4) | 25(4) | 2(3) | 3(3) | −4(3) |
| C204 | 17(4) | 35(5) | 19(4) | 5(3) | 2(3) | 6(3) |
| C205 | 19(4) | 21(4) | 20(4) | 5(3) | 3(3) | 0(3) |
| C206 | 22(4) | 27(4) | 18(4) | 0(3) | 2(3) | −10(3) |
| C207 | 40(5) | 22(4) | 21(4) | 3(3) | −7(3) | −8(4) |
| C208 | 41(5) | 28(4) | 15(4) | −1(3) | −2(4) | −5(4) |
| C209 | 39(5) | 24(4) | 24(5) | −7(3) | 11(4) | −6(4) |
| C210 | 24(4) | 21(4) | 31(5) | −3(3) | 12(3) | −6(3) |

TABLE 10-continued

Anisotropic displacement parameters [Å² × 10³].
The anisotropic displacement factor exponent takes the
form: −2π[h²a*²U¹¹ + ... + 2 h k a* b* U¹²].

| Atom | U¹¹ | U²² | U³³ | U²³ | U¹³ | U¹² |
|---|---|---|---|---|---|---|
| C211 | 21(4) | 22(4) | 23(4) | 2(3) | 4(3) | −6(3) |
| C212 | 34(5) | 24(4) | 37(5) | −13(4) | 15(4) | 1(4) |
| C213 | 36(5) | 32(5) | 44(6) | −10(4) | 15(4) | 0(4) |
| C214 | 41(6) | 22(4) | 57(6) | −5(4) | 4(4) | −7(4) |
| C215 | 38(6) | 36(5) | 70(7) | 7(5) | 3(5) | 6(4) |
| C216 | 53(7) | 63(7) | 55(7) | 3(6) | 11(5) | −5(6) |
| C217 | 50(6) | 56(6) | 43(6) | 4(5) | 8(5) | 11(5) |
| C218 | 39(6) | 48(6) | 34(5) | 7(4) | 5(4) | 9(4) |
| S301 | 20(1) | 32(1) | 16(1) | −1(1) | 2(1) | 5(1) |
| O301 | 14(3) | 22(3) | 24(3) | 2(2) | 0(2) | 2(2) |
| O302 | 15(3) | 25(3) | 13(3) | −4(2) | 1(2) | 5(2) |
| O303 | 15(3) | 25(3) | 15(3) | 3(2) | 2(2) | 5(2) |
| O304 | 23(3) | 24(3) | 16(3) | 3(2) | 0(2) | 9(2) |
| O305 | 22(3) | 25(3) | 21(3) | 3(2) | 2(2) | −2(2) |
| O306 | 35(3) | 23(3) | 26(3) | −4(2) | −3(2) | 1(2) |
| O307 | 28(3) | 31(3) | 33(3) | 0(3) | 1(2) | −3(2) |
| N301 | 12(3) | 22(3) | 16(3) | −2(3) | 3(2) | 2(3) |
| C301 | 19(4) | 19(4) | 19(4) | 1(3) | −5(3) | 3(3) |
| C302 | 14(4) | 19(4) | 24(4) | −4(3) | −2(3) | 2(3) |
| C303 | 26(4) | 24(4) | 22(4) | −1(3) | −2(3) | 0(3) |
| C304 | 15(4) | 28(4) | 13(4) | −4(3) | 1(3) | 2(3) |
| C305 | 10(4) | 18(4) | 19(4) | −6(3) | 2(3) | −7(3) |
| C306 | 21(4) | 18(4) | 17(4) | −2(3) | −1(3) | −3(3) |
| C307 | 19(4) | 28(4) | 21(4) | −1(3) | 4(3) | −6(3) |
| C308 | 31(5) | 22(4) | 12(4) | −2(3) | −2(3) | −6(3) |
| C309 | 25(4) | 24(4) | 22(4) | 5(3) | −2(3) | 4(3) |
| C310 | 23(4) | 19(4) | 14(4) | −3(3) | −4(3) | 1(3) |
| C311 | 18(4) | 22(4) | 19(4) | 0(3) | −3(3) | −4(3) |
| C312 | 19(4) | 23(4) | 23(4) | 6(3) | −2(3) | 3(3) |
| C313 | 16(4) | 24(4) | 26(4) | 9(3) | 1(3) | 3(3) |
| C314 | 31(5) | 25(4) | 28(5) | 1(3) | 5(3) | −1(4) |
| C315 | 33(5) | 22(4) | 29(4) | 0(3) | 9(3) | −2(4) |
| C316 | 38(5) | 27(5) | 39(5) | −4(4) | −5(4) | −6(4) |
| C317 | 33(5) | 30(5) | 39(5) | −1(4) | −1(4) | −1(4) |
| C318 | 31(5) | 37(5) | 42(5) | 1(4) | −2(4) | 6(4) |
| S401 | 21(1) | 30(1) | 21(1) | −1(1) | −3(1) | −7(1) |
| O401 | 14(3) | 38(3) | 22(3) | 4(2) | 3(2) | −1(2) |
| O402 | 17(3) | 26(3) | 18(3) | 3(2) | −1(2) | −2(2) |
| O403 | 15(3) | 26(3) | 16(3) | 0(2) | 0(2) | −5(2) |
| O404 | 23(3) | 27(3) | 23(3) | 4(2) | 2(2) | −6(2) |
| O405 | 20(3) | 21(3) | 26(3) | 3(2) | −2(2) | −1(2) |
| O406 | 22(3) | 27(3) | 26(3) | −1(2) | 4(2) | −2(2) |
| O407 | 38(4) | 31(3) | 35(3) | −4(3) | 15(3) | −6(3) |
| N401 | 14(3) | 20(3) | 18(3) | −1(2) | 1(2) | −2(2) |
| C401 | 22(4) | 13(4) | 23(4) | 0(3) | 4(3) | 5(3) |
| C402 | 14(4) | 22(4) | 22(4) | −1(3) | 1(3) | −3(3) |
| C403 | 27(4) | 32(5) | 18(4) | −5(3) | 3(3) | −1(4) |
| C404 | 14(4) | 33(5) | 35(5) | −8(3) | 4(3) | −2(3) |
| C405 | 13(4) | 15(4) | 19(4) | −4(3) | −4(3) | 2(3) |
| C406 | 20(4) | 17(4) | 26(4) | −2(3) | 0(3) | 3(3) |
| C407 | 33(5) | 27(4) | 19(4) | −5(3) | 1(3) | −3(4) |
| C408 | 30(5) | 41(5) | 13(4) | 1(4) | 0(3) | 0(4) |
| C409 | 21(4) | 27(4) | 25(4) | 9(3) | 9(3) | −3(3) |
| C410 | 20(4) | 14(4) | 24(4) | 2(3) | 4(3) | 2(3) |
| C411 | 20(4) | 17(4) | 17(4) | −1(3) | −4(3) | 6(3) |
| C412 | 18(4) | 19(4) | 27(4) | 5(3) | 8(3) | 0(3) |
| C413 | 11(4) | 30(4) | 32(5) | 6(3) | 7(3) | −2(3) |
| C414 | 20(4) | 21(4) | 30(4) | 7(3) | −2(3) | 4(3) |
| C415 | 20(4) | 28(4) | 36(5) | 3(4) | 4(3) | −5(4) |
| C416 | 33(5) | 27(4) | 28(5) | 2(3) | 5(4) | 1(4) |
| C417 | 30(5) | 27(4) | 24(4) | −2(3) | 3(3) | −3(4) |
| C418 | 28(5) | 43(5) | 29(5) | 1(4) | 2(4) | 0(4) |
| O1W | 30(4) | 27(4) | 31(4) | −7(3) | −3(3) | −3(3) |
| O2W | 19(3) | 32(3) | 22(3) | −6(2) | −1(2) | 5(2) |
| O3W | 28(3) | 49(4) | 16(3) | −1(3) | 3(3) | −8(3) |
| O4W | 33(4) | 34(3) | 37(3) | 9(3) | −11(3) | −6(3) |
| O5W | 21(3) | 42(3) | 16(3) | 7(2) | −3(2) | −6(2) |
| O6W | 26(3) | 36(3) | 17(3) | 4(2) | 2(2) | 11(3) |

TABLE 11

Hydrogen coordinates [× 10⁴] and isotropic
displacement parameters [Å² × 10³].

| Atom | x | y | z | U$_{eq}$ | S.o.f. |
|---|---|---|---|---|---|
| H10A | 9865 | 17028 | 354 | 36 | 1 |
| H10B | 11367 | 17439 | 624 | 36 | 1 |
| H10C | 9016 | 17001 | 696 | 36 | 1 |
| H10D | 14980 | 15837 | 498 | 30 | 1 |
| H10E | 14337 | 16682 | 358 | 30 | 1 |
| H107 | 9989 | 14808 | −273 | 26 | 1 |
| H108 | 7365 | 13989 | −524 | 29 | 1 |
| H109 | 4511 | 13367 | −260 | 29 | 1 |
| H11A | 3126 | 12556 | 50 | 26 | 1 |
| H11B | 1117 | 13201 | 51 | 26 | 1 |
| H11C | 164 | 12806 | 547 | 30 | 1 |
| H11D | −110 | 12093 | 314 | 30 | 1 |
| H11E | 4952 | 11650 | 328 | 30 | 1 |
| H11F | 2674 | 11117 | 308 | 30 | 1 |
| H11G | 3717 | 10639 | 817 | 32 | 1 |
| H11H | 5536 | 10387 | 570 | 32 | 1 |
| H11I | 9031 | 10385 | 888 | 36 | 1 |
| H11J | 7231 | 10388 | 1156 | 36 | 1 |
| H11K | 10543 | 11618 | 1083 | 32 | 1 |
| H11L | 8910 | 11527 | 1368 | 32 | 1 |
| H11M | 13929 | 11531 | 1388 | 58 | 1 |
| H11N | 14358 | 10809 | 1614 | 58 | 1 |
| H11O | 12499 | 11462 | 1690 | 58 | 1 |
| H20A | 14287 | 13062 | 1957 | 37 | 1 |
| H20B | 15606 | 12950 | 1647 | 37 | 1 |
| H20C | 13232 | 13427 | 1645 | 37 | 1 |
| H20X | 19551 | 13841 | 1918 | 29 | 1 |
| H20Y | 17944 | 13423 | 2159 | 29/ | 1 |
| H207 | 16118 | 15333 | 2781 | 34 | 1 |
| H208 | 14116 | 16144 | 3093 | 34 | 1 |
| H209 | 11026 | 16913 | 2886 | 34 | 1 |
| H21A | 8975 | 17866 | 2593 | 37 | 1 |
| H21B | 7410 | 17099 | 2627 | 37 | 1 |
| H21C | 5242 | 17374 | 2189 | 44 | 1 |
| H21D | 5425 | 18188 | 2367 | 44 | 1 |
| H21E | 10005 | 18664 | 2211 | 48 | 1 |
| H21F | 7768 | 19214 | 2173 | 48 | 1 |
| H21G | 8235 | 19266 | 1647 | 58 | 1 |
| H21H | 10466 | 19605 | 1833 | 58 | 1 |
| H21I | 13308 | 19340 | 1530 | 68 | 1 |
| H21J | 11357 | 19164 | 1268 | 68 | 1 |
| H21K | 12920 | 17947 | 1187 | 59 | 1 |
| H21L | 14807 | 18083 | 1462 | 59 | 1 |
| H21M | 17930 | 18031 | 1109 | 60 | 1 |
| H21N | 17743 | 18534 | 802 | 60 | 1 |
| H21O | 15978 | 17832 | 851 | 60 | 1 |
| H30A | 182 | 12226 | 4679 | 36 | 1 |
| H3OB | −1323 | 12641 | 4410 | 36 | 1 |
| H30C | 1052 | 12219 | 4338 | 36 | 1 |
| H30X | −4856 | 11003 | 4520 | 23 | 1 |
| H30Y | −4265 | 11838 | 4672 | 23 | 1 |
| H307 | 261 | 9942 | 5273 | 27 | 1 |
| H308 | 2854 | 9091 | 5510 | 26 | 1 |
| H309 | 5661 | 8454 | 5222 | 28 | 1 |
| H31A | 6923 | 7670 | 4904 | 26 | 1 |
| H31B | 8956 | 8302 | 4888 | 26 | 1 |
| H31C | 9649 | 7903 | 4384 | 26 | 1 |
| H31D | 10027 | 7197 | 4618 | 26 | 1 |
| H31E | 4912 | 6749 | 4638 | 34 | 1 |
| H31F | 7206 | 6223 | 4651 | 34 | 1 |
| H31G | 6095 | 5718 | 4154 | 34 | 1 |
| H31H | 4260 | 5494 | 4403 | 34 | 1 |
| H31I | 1516 | 5391 | 3964 | 42 | 1 |
| H31J | 3276 | 5745 | 3728 | 42 | 1 |
| H31K | −764 | 5999 | 3591 | 41 | 1 |
| H31L | −817 | 6557 | 3884 | 41 | 1 |
| H31X | −1738 | 7206 | 3306 | 55 | 1 |
| H31Y | 66 | 7912 | 3326 | 55 | 1 |
| H31Z | −1450 | 7712 | 3611 | 55 | 1 |
| H40A | 5447 | 8615 | 2925 | 39 | 1 |
| H40B | 4088 | 8349 | 3216 | 39 | 1 |
| H40C | 6487 | 8806 | 3260 | 39 | 1 |
| H40D | 427 | 9878 | 2962 | 33 | 1 |
| H40E | 1031 | 8996 | 2869 | 33 | 1 |
| H407 | 5406 | 10553 | 2161 | 32 | 1 |

TABLE 11-continued

Hydrogen coordinates [× 10⁴] and isotropic displacement parameters [Å² × 10³].

| Atom | x | y | z | $U_{eq}$ | S.o.f. |
|---|---|---|---|---|---|
| H408 | 7895 | 11304 | 1889 | 34 | 1 |
| H409 | 10766 | 12062 | 2149 | 29 | 1 |
| H41A | 12220 | 13057 | 2444 | 26 | 1 |
| H41B | 13969 | 12328 | 2458 | 26 | 1 |
| H41C | 15628 | 12716 | 2917 | 29 | 1 |
| H41D | 15423 | 13503 | 2722 | 29 | 1 |
| H41E | 10397 | 13753 | 2804 | 28 | 1 |
| H41F | 12375 | 14410 | 2819 | 28 | 1 |
| H41G | 11720 | 14581 | 3350 | 33 | 1 |
| H41H | 9495 | 14808 | 3138 | 33 | 1 |
| H41I | 6716 | 14552 | 3468 | 35 | 1 |
| H41J | 8716 | 14446 | 3730 | 35 | 1 |
| H41K | 5382 | 13251 | 3573 | 32 | 1 |
| H41L | 7301 | 13193 | 3848 | 32 | 1 |
| H41M | 2240 | 13218 | 3904 | 50 | 1 |
| H41N | 2305 | 13773 | 4197 | 50 | 1 |
| H41O | 4104 | 13069 | 4178 | 50 | 1 |
| H901 | 6240(110) | 12330(20) | 993(16) | 35 | 1 |
| H902 | 7720(70) | 12940(40) | 1091(17) | 35 | 1 |
| H903 | −620(110) | 13930(40) | 818(9) | 29 | 1 |
| H904 | −50(120) | 14000(40) | 1127(9) | 29 | 1 |
| H905 | 5920(110) | 16410(50) | 1432(7) | 37 | 1 |
| H906 | 5360(100) | 16390(50) | 1737(11) | 37 | 1 |
| H907 | 3400(70) | 7640(40) | 3832(16) | 42 | 1 |
| H908 | 5460(100) | 7590(40) | 3999(14) | 42 | 1 |
| H909 | 10600(100) | 9170(40) | 4170(10) | 32 | 1 |
| H910 | 9990(110) | 9200(40) | 3862(8) | 32 | 1 |
| H911 | 14620(100) | 11740(50) | 3580(7) | 32 | 1 |
| H912 | 15040(90) | 11700(40) | 3269(10) | 32 | 1 |

TABLE 12

Hydrogen bonds [Å and °].

| D—H...A | d(D—H) | d(H...A) | d(D...A) | ∠ (DHA) |
|---|---|---|---|---|
| O1W—H901...O106 | 0.83(3) | 2.00(3) | 2.813(7) | 167(7) |
| O1W—H902...O2W[ii] | 0.84(3) | 2.11(4) | 2.867(8) | 149(7) |
| O2W—H903...O103[i] | 0.84(3) | 1.92(4) | 2.706(7) | 157(6) |
| O2W—H904...O201[iii] | 0.85(3) | 1.90(3) | 2.733(6) | 169(7) |
| O3W—H905...O101[i] | 0.85(3) | 1.90(3) | 2.740(7) | 170(8) |
| O3W—H906...O203[i] | 0.84(3) | 2.00(4) | 2.820(7) | 164(7) |
| O4W—H907...O306 | 0.86(3) | 2.56(7) | 2.996(7) | 113(5) |
| O4W—H907...O307 | 0.86(3) | 2.09(4) | 2.869(8) | 150(7) |
| O4W—H908...O305 | 0.86(3) | 1.99(3) | 2.851(7) | 173(7) |
| O4W—H907...O306 | 0.86(3) | 2.56(7) | 2.996(7) | 113(5) |
| O5W—H909...O303[ii] | 0.85(3) | 1.93(4) | 2.754(7) | 161(6) |
| O5W—H910...O401[ii] | 0.85(3) | 1.91(3) | 2.754(7) | 171(7) |
| O6W—H911...O301[iv] | 0.83(3) | 1.90(3) | 2.726(7) | 169(7) |
| O6W—H912...O403[ii] | 0.84(3) | 2.15(4) | 2.955(7) | 162(6) |

Symmetry transformations used to generate equivalent atoms:
(i) x − 1, y, z
(ii) x + 1, y, z
(iii) x − 2, y, z
(iv) x + 2, y, z

Example 12

Human Pharmacokinetics

The purpose of this Example is to characterize the pharmacokinetic profiles of Compound 1 (disodium salt) and its magnesium hydroxide salt counterpart, Compound 3:

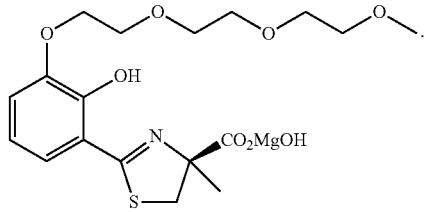

The synthesis of Compound 3 is described in International Patent Publication No. WO 2013/086312, the entire contents of which are incorporated by reference herein.

This human study is part of an open-label, randomized, single dose, 3-period, relative bioavailability study in up to 28 healthy adults 18-65 years of age inclusive, investigating the pharmacokinetics, safety, and tolerability of Compounds 1 and 3. In this study, each study compound is administered as a single dose of 36.2 mg/kg/day or 18.1 mg/kg/day, respectively (as free acid), and as 2 doses of 36.2 mg/kg or 18.1 mg/kg, respectively (as free acid), given 12 hours apart. Table 13 provides dosages relative to free acid content.

TABLE 13

Comparable dosages of Magnesium Salt and Disodium Salt Relative to Free Acid Content

| Free Acid | Magnesium Salt | Disodium Salt |
|---|---|---|
| 36.2 mg/kg | 40 mg/kg | 43.6 mg/kg |
| 18.1 mg/kg | 20 mg/kg | 21.8 mg/kg |

Investigational Product, Dose, and Mode of Administration:

The magnesium hydroxide salt (Compound 3) is administered as oral capsules in the following strengths: 50, 100, 200, 375 and 500 mg. The disodium salt (Compound 1) is administered as oral capsules in the following strengths: 54.1, 272.8 and 408.7 mg. The table below shows comparable dosages of the magnesium salt and disodium salt relative to free acid content.

| Magnesium Salt | Free Acid of Magnesium Salt Capsules | Disodium Salt | Free Acid of Disodium Salt Capsules |
|---|---|---|---|
| 50 mg | 45.3 mg | 54.1 mg | 45 mg |
| 250 mg | 226.5 mg | 272.8 mg | 227 mg |
| 375 mg | 339.8 mg | 408.7 mg | 340 mg |

There will be 3 treatment periods in this study and 4 possible treatments. The treatments to be given during these treatment periods are:

Treatment A: Compound 3: 40 mg/kg (the same as 36.2 mg/kg free acid dose) administered as a single dose in a fasted state in the morning.

Treatment B: Compound 1: 21.8 mg/kg (the same as 18.1 mg/kg free acid dose) administered as a single dose in a fasted state in the morning.

Treatment C: Compound 3: 40 mg/kg (the same as 36.2 mg/kg free acid dose) administered in the morning and 40 mg/kg administered 12 hours later.

Treatment D: Compound 1: 21.8 mg/kg (the same as 18.1 mg/kg free acid dose) administered in the morning and 21.8 mg/kg 12 hours later.

Each subject will be randomized into 1 of 4 different treatment sequences listed below. Each treatment sequence will consist of 3 treatment periods. The 4 possible treatment sequences subjects may be randomized to are: ABC, BAC, ABD, or BAD. Treatment Periods 1, 2, and 3 will be 6 days in length to collect pharmacokinetic and safety assessments.

Pharmacokinetic Procedures

Actual pharmacokinetic blood sample collection times versus time of dosing will be monitored. The following blood will be taken for analysis: 6 mL of blood collected in a 6 mL lithium heparin collection tube for plasma measurement of i) total Compound 2 ("total"), ii) unbound Compound 2 ("free"), and iii) iron bound Compound 2. The blood samples will be used to determine these plasma concentrations.

The pharmacokinetic parameters will include, but not be limited to:

| | |
|---|---|
| $C_{max}$ | Maximum concentration occurring at tmax |
| $t_{max}$ | Time of maximum observed concentration sampled during a dosing interval |
| $AUC_{inf}$ | Area under the curve extrapolated to infinity, calculated using the observed value of the last non-zero concentration |
| $AUC_{last}$ | Area under the curve from the time of dosing to the last measurable concentration |
| $AUC_{0-12}$ | Area under the curve from the time of dosing to 12 hours post-dose |
| $AUC_{0-24}$ | Area under the curve from the time of dosing to 24 hours post-dose |
| $\lambda_z$ | First order rate constant associated with the terminal (log-linear) portion of the curve |
| $t^{1}/_{2}$ | Terminal half-life |
| CL/F | Total body clearance for extravascular administration divided by the fraction of dose absorbed |
| Vz/F | Volume of distribution associated with the terminal slope following extravascular administration divided by the fraction of dose absorbed |

Results

The results showed that Compound 1 produces a Cmax~35% higher and an AUC~22% higher than Compound 3. See Table 14.

Figure 14:
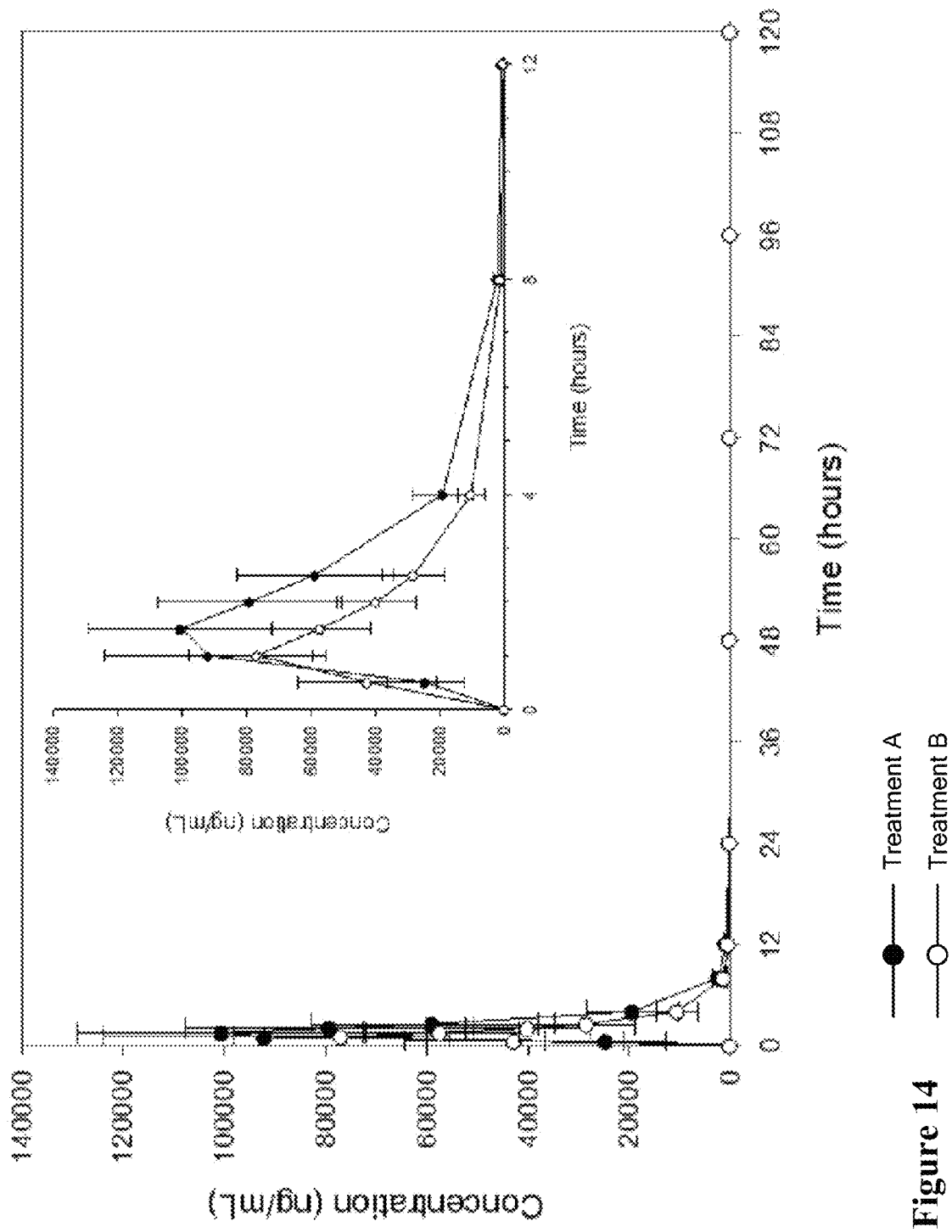
FIG. 14. Total plasma concentration (i.e., Compound 2) (mean±SD) in subjects following administration of Compound 1 or Compound 3 (linear scale); treatment A: Compound 3 40 mg/kg single dose, treatment B: Compound 1 21.8 mg/kg single dose.
Figure 15:
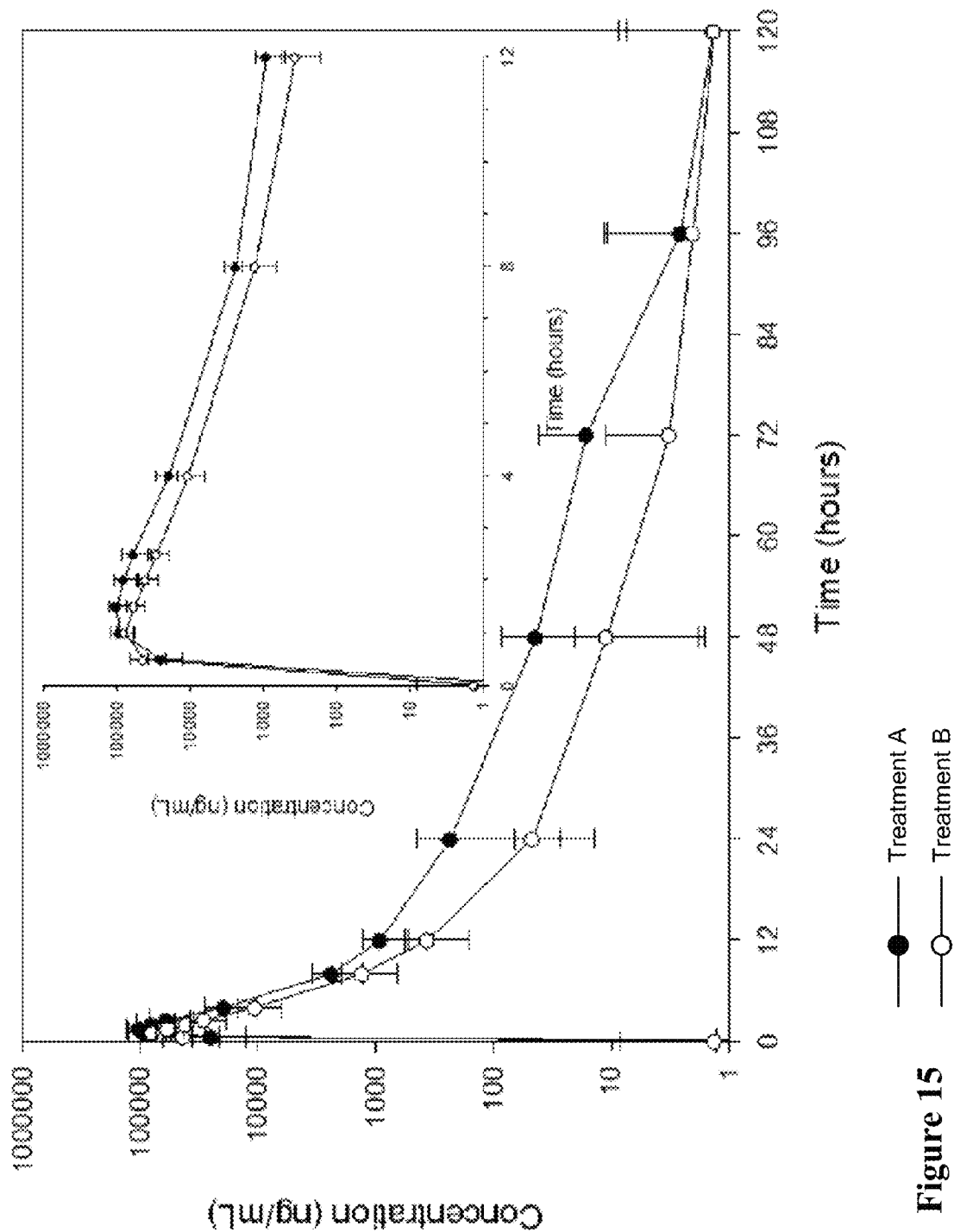
FIG. 15. Total plasma concentration (i.e., Compound 2) (mean±SD) in subjects following administration of Compound 1 or Compound 3 (log scale); treatment A: Compound 3 40 mg/kg single dose, treatment B: Compound 1 21.8 mg/kg single dose.
Figure 16:
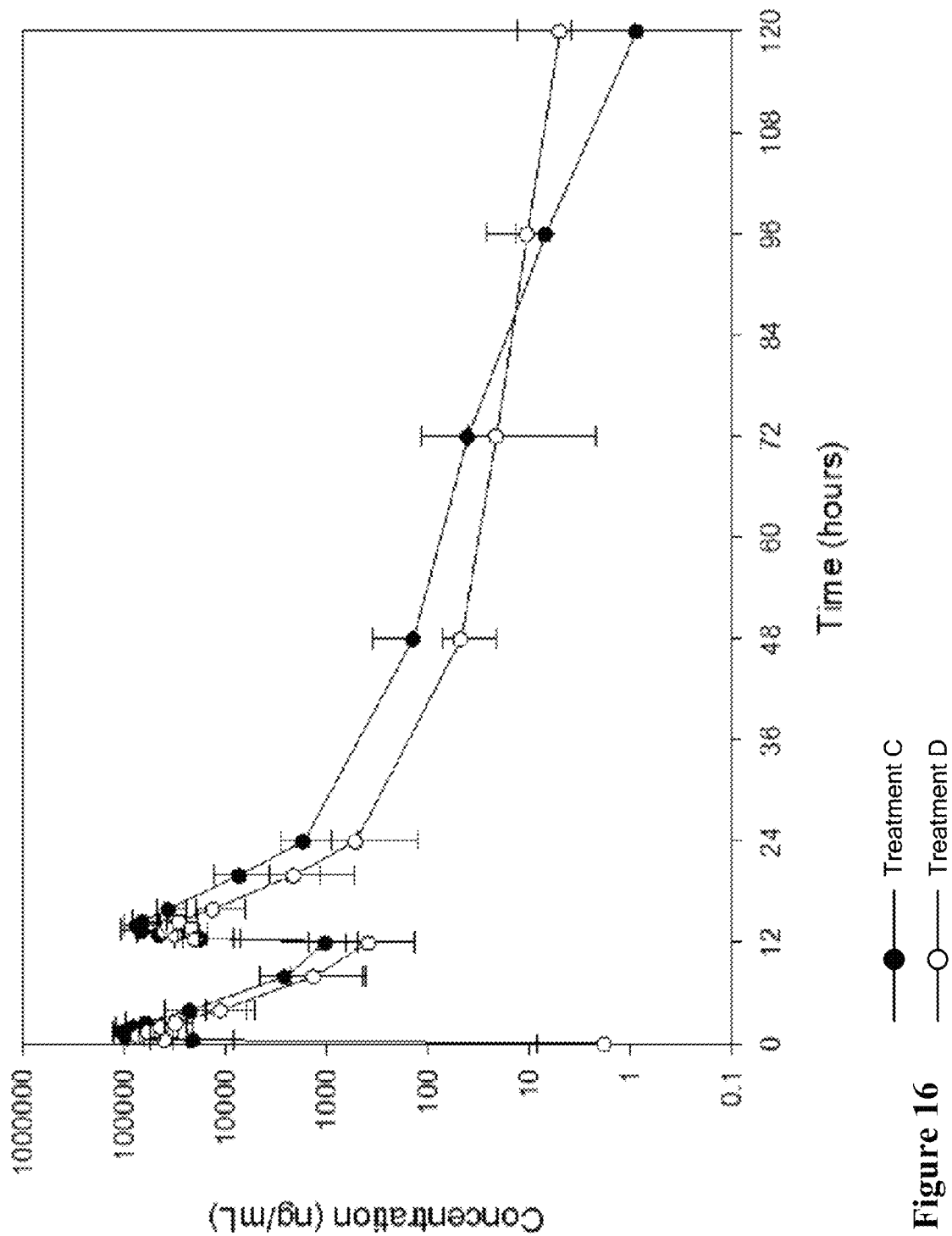
FIG. 16. Total plasma concentration (i.e., Compound 2) (mean±SD) in subjects following administration of Compound 1 or Compound 3 (log scale); treatment C: Compound 3 40 mg/kg morning and evening dose, treatment D: Compound 1 21.8 mg/kg morning and evening dose.

FIGS. 14-16 show additional data regarding plasma concentrations of Compound 2 following administration of Compound 1 or 3.

TABLE 14

| | | Geometric LS Means | | |
|---|---|---|---|---|
| Analyte | Parameter | A | B | B/A |
| Compound 2 (total) | AUCinf (ng · h/mL) | 252926.1 | 311981.0 | |
| | Ratio | | | 1.233 |
| | 90% CI of Ratio | | | (1.070, 1.422) |
| | AUClast (ng · h/mL) | 250422.0 | 311408.3 | |
| | Ratio | | | 1.244 |
| | 90% CI of Ratio | | | (1.081, 1.430) |
| | Cmax (ng/mL) | 106314.2 | 142905.1 | |
| | Ratio | | | 1.344 |
| | 90% CI of Ratio | | | (1.135, 1.592) |

Treatment A: Compound 3 40 mg/kg single dose
Treatment B: Compound 1 21.8 mg/kg single dose
Exponentiated LSMeans and CIs are from an ANOVA on natural log transformed data
Doses are normalized to the Compound 3 (40 mg/kg) dose prior to the ANOVA From the foregoing description, one skilled in the art can easily ascertain the essential characteristics of this invention, and without departing from the spirit and scope thereof, can make various changes and modifications of the invention to adapt it to various usages and conditions.

All references, patents or applications, U.S. or foreign, cited in the application are hereby incorporated by reference as if written herein in their entireties. Where any inconsistencies arise, material literally disclosed herein controls.

The invention claimed is:

1. Crystalline form of Compound 1 having a water content in the range of about 1-9 wt %:

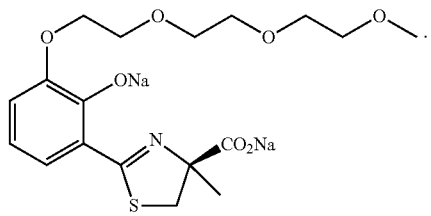

2. The crystalline form according to claim 1, wherein the crystalline form is Form A having one or more peaks in its powder X-ray diffraction pattern selected from those at about 5.8°, about 7.3°, about 7.6°, about 10.7°, about 11.3°, about 11.6°, about 14.6°, about 16.4°, about 16.8°, about 17.3°, about 18.4°, about 18.9°, about 20.4°, about 20.9°, about 21.4°, about 21.8°, about 23.8°, about 25.8°, about 26.4°, about 27.5°, about 29.1°, about 30.3°, about 31.4°, and about 32.4° 2-theta.

3. The crystalline form according to claim 1, wherein the crystalline form is Form B having one or more peaks in its powder X-ray diffraction pattern selected from those at about 6.6°, about 9.5°, about 10.3°, about 13.1°, about 15.8°, about 16.0°, about 17.4°, about 18.2°, about 18.9°, about 19.8°, about 20.3°, about 20.7°, about 21.1°, about 21.7°, about 22.2°, about 23.0°, about 23.3°, about 24.6°, about 25.2°, about 26.2°, about 26.8°, about 27.2°, about 28.7°, and about 30.0° 2-theta.

4. The crystalline form according to claim 1, wherein the crystalline form is Form C having one or more peaks in its powder X-ray diffraction pattern selected from those at about 6.6°, about 6.8°, about 9.5°, about 9.8°, about 10.3°, about 10.7°, about 13.4°, about 16.3°, about 18.2°, about 19.5°, about 19.9°, about 22.0°, about 23.0°, about 23.4°, about 24.9°, about 25.8°, about 26.5°, about 27.4°, and about 29.5° 2-theta.

5. The crystalline form according to claim 1, wherein the crystalline form is Form D having one or more peaks in its powder X-ray diffraction pattern selected from those at about 6.8°, about 9.4°, about 11.5°, about 13.6°, about 15.3°, about 17.0°, about 19.3°, about 20.2°, about 21.5°, about 22.3°, about 23.0°, about 25.2°, and about 29.4° 2-theta.

6. A composition comprising a crystalline form according to claim 1.

7. The composition according to claim 6, wherein the composition further comprises a pharmaceutically acceptable carrier.

8. An oral formulation comprising the composition of claim 7.

9. A method of producing a polymorph according to claim 2, comprising the steps of:

(a) reacting Compound 2

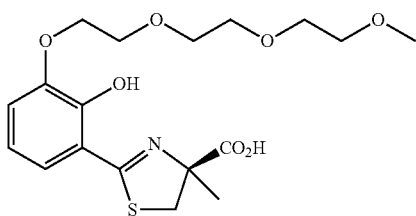

with NaOH in the presence of one or more solvents; and
(b) inducing crystallization;
wherein crystallization provides Form A of Compound 1.

10. A method of producing a polymorph according to claim 3, comprising the steps of:
(a) mixing Form A of Compound 1 with one or more solvents;
(b) heating up the mixture to about 30-50° C.; and
(c) inducing crystallization;
wherein crystallization provides polymorph Form B of Compound 1.

11. A method of producing a polymorph according to claim 4, comprising the steps of:
(a) dissolving Form A of Compound 1 in a first solvent;
(b) adding a second solvent; and
(c) inducing crystallization;
wherein crystallization provides polymorph Form C of Compound 1.

12. A method of producing a polymorph according to claim 5, comprising the step of drying Form A of Compound 1 under reduced pressure at elevated temperature, to provide polymorph Form D of Compound 1.

13. A method for treating metal overload, comprising a step of administering to a subject in need of treatment a therapeutically effective amount of a crystalline form of Compound 1 according to claim 1.

* * * * *